United States Patent
Mackay et al.

(10) Patent No.: US 12,259,392 B2
(45) Date of Patent: Mar. 25, 2025

(54) SYSTEM AND METHODS FOR MULTIPLEXED ANALYSIS OF CELLULAR AND OTHER IMMUNOTHERAPEUTICS

(71) Applicant: IsoPlexis Corporation, Branford, CT (US)

(72) Inventors: Sean Mackay, New Haven, CT (US); Colin Ng, Branford, CT (US); Emily Bettini, Waterbury, CT (US)

(73) Assignee: IsoPlexis Corporation, Branford, CT (US)

( * ) Notice: Subject to any disclaimer, the term of this patent is extended or adjusted under 35 U.S.C. 154(b) by 0 days.

(21) Appl. No.: 18/119,339

(22) Filed: Mar. 9, 2023

(65) Prior Publication Data
US 2023/0221328 A1   Jul. 13, 2023

Related U.S. Application Data

(63) Continuation of application No. 16/332,627, filed as application No. PCT/US2017/051223 on Sep. 12, 2017, now abandoned.

(60) Provisional application No. 62/480,752, filed on Apr. 3, 2017, provisional application No. 62/480,147, filed on Mar. 31, 2017, provisional application No. 62/431,318, filed on Dec. 7, 2016, provisional application No. 62/393,612, filed on Sep. 12, 2016.

(51) Int. Cl.
*G01N 33/68* (2006.01)
*G01N 33/50* (2006.01)

(52) U.S. Cl.
CPC ......... *G01N 33/68* (2013.01); *G01N 33/5014* (2013.01); *G01N 33/505* (2013.01); *G01N 33/5091* (2013.01); *G01N 2800/7095* (2013.01)

(58) Field of Classification Search
None
See application file for complete search history.

(56) References Cited

U.S. PATENT DOCUMENTS

| | | |
|---|---|---|
| 5,020,123 A | 5/1991 | Thompson |
| 5,858,801 A | 1/1999 | Brizzolara |
| 6,039,897 A | 3/2000 | Lochhead et al. |
| 6,165,739 A | 12/2000 | Clatch |
| 6,377,721 B1 | 4/2002 | Walt et al. |
| 6,429,027 B1 | 8/2002 | Chee et al. |
| 6,524,790 B1 | 2/2003 | Kopf-Sill et al. |
| 6,699,665 B1 | 3/2004 | Kim et al. |
| 6,924,153 B1 | 8/2005 | Boehringer et al. |
| 7,312,197 B2 | 12/2007 | Gong et al. |
| 7,381,375 B2 | 6/2008 | Ravkin et al. |
| 7,491,498 B2 | 2/2009 | Lapidus et al. |
| 7,541,444 B2 | 6/2009 | Milton et al. |
| 7,666,593 B2 | 2/2010 | Lapidus |
| 7,776,553 B2 | 8/2010 | Love et al. |
| 7,785,796 B2 | 8/2010 | Balasubramanian et al. |
| 8,105,845 B2 | 1/2012 | Notcovich et al. |
| 8,236,532 B2 | 8/2012 | Ronaghi et al. |
| 8,394,590 B2 | 3/2013 | Kwong et al. |
| 8,460,878 B2 | 6/2013 | Walt et al. |
| 8,492,165 B2 | 7/2013 | Van et al. |
| 8,753,816 B2 | 6/2014 | Rigatti et al. |
| 8,802,368 B2 | 8/2014 | Lapidus |
| 8,865,479 B2 | 10/2014 | Love et al. |
| 9,005,929 B2 | 4/2015 | Ronaghi et al. |
| 9,051,612 B2 | 6/2015 | Zhao et al. |
| 9,121,060 B2 | 9/2015 | Milton et al. |
| 9,188,586 B2 | 11/2015 | Fan et al. |
| 9,388,464 B2 | 7/2016 | Milton et al. |
| 9,409,987 B2 | 8/2016 | Toporik et al. |
| 9,453,258 B2 | 9/2016 | Kain et al. |
| 9,506,917 B2 | 11/2016 | Fan et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,701,998 B2 | 7/2017 | Hindson et al. |
| 9,727,810 B2 | 8/2017 | Fodor et al. |
| 9,765,391 B2 | 9/2017 | Swerdlow |
| 9,824,870 B1 | 11/2017 | Straume et al. |
| 9,845,502 B2 | 12/2017 | Fodor et al. |
| 9,952,126 B2 | 4/2018 | Fowler et al. |
| 9,953,209 B2 | 4/2018 | Adalsteinsson et al. |
| 10,002,316 B2 | 6/2018 | Fodor et al. |
| 10,131,958 B1 | 11/2018 | Fan et al. |
| 10,137,426 B2 | 11/2018 | Love et al. |
| 10,151,003 B2 | 12/2018 | Fan et al. |

(Continued)

FOREIGN PATENT DOCUMENTS

| | | |
|---|---|---|
| AU | 2013240127 A1 | 10/2014 |
| CN | 1419597 A | 5/2003 |

(Continued)

OTHER PUBLICATIONS

Adams, J. D., et al., "Multitarget magnetic activated cell sorter", Proceedings of the National Academy of Sciences (2008); 105(47): 18165-18170.

Adler, M., et al., "Detection of femtogram amounts of biogenic amines using self-assembled DNA-protein nanostructures", Nature Methods (2005); 2(2):147-149.

Altschul, S. F., et al., "Basic local alignment search tool", Journal of Molecular Biology (1990); 215(3): 403-410.

Altschul, S. F., et al., "Gapped BLAST and PSI-BLAST: a new generation of protein database search programs", Nucleic Acids Research (1997); 25(17): 3389-3402.

Amir, E. D., et al., "viSNE enables visualization of high dimensional single-cell data and reveals phenotypic heterogeneity of leukemia", Nature Biotechnology (Jun. 2013); 31(6): 545-552.

(Continued)

*Primary Examiner* — Robert J Yamasaki

(74) *Attorney, Agent, or Firm* — COOLEY LLP; Matthew Pavao; Brian P. Hopkins

(57) ABSTRACT

Disclosed are methods of identifying a secretome from a subject cell within a heterogeneous cell population when the subject cell contacts a target cell (e.g. a subject immune cell contacts a target cancer cell) or a stimulatory agent and methods of using the identified secretome to identify cells that are safe and efficacious for cellular therapies, including adoptive CAR T-cell therapies.

16 Claims, 46 Drawing Sheets

(56) References Cited

U.S. PATENT DOCUMENTS

| | | |
|---|---|---|
| 10,190,965 B2 | 1/2019 | Handique et al. |
| 10,208,356 B1 | 2/2019 | Fan et al. |
| 10,253,375 B1 | 4/2019 | Fan et al. |
| 10,273,541 B2 | 4/2019 | Hindson et al. |
| 10,274,486 B2 | 4/2019 | Fan et al. |
| 10,337,063 B1 | 7/2019 | Brenner et al. |
| 10,378,051 B2 | 8/2019 | Meuleman et al. |
| 10,391,492 B2 | 8/2019 | Handique et al. |
| 10,391,493 B2 | 8/2019 | Handique et al. |
| 10,400,280 B2 | 9/2019 | Hindson et al. |
| 10,436,700 B1 | 10/2019 | Handique et al. |
| 10,513,731 B2 | 12/2019 | Milton et al. |
| 10,584,366 B2 | 3/2020 | Paczkowski et al. |
| 10,619,196 B1 | 4/2020 | Chee |
| 10,633,702 B2 | 4/2020 | Brenner et al. |
| 10,641,700 B2 | 5/2020 | Handique |
| 10,676,789 B2 | 6/2020 | Hindson et al. |
| 10,718,007 B2 | 7/2020 | Handique et al. |
| 10,746,648 B2 | 8/2020 | Handique |
| 10,752,950 B2 | 8/2020 | Hindson et al. |
| 10,774,374 B2 | 9/2020 | Frisen et al. |
| 10,793,904 B2 | 10/2020 | Swerdlow |
| 10,821,440 B2 | 11/2020 | Handique et al. |
| 10,921,237 B2 | 2/2021 | Handique |
| 10,927,419 B2 | 2/2021 | Fan et al. |
| 10,928,389 B2 | 2/2021 | Fan et al. |
| 10,941,396 B2 | 3/2021 | Fu et al. |
| 10,954,570 B2 | 3/2021 | Fan et al. |
| 10,983,116 B2 | 4/2021 | Fan et al. |
| 11,021,749 B2 | 6/2021 | Hindson et al. |
| 11,066,689 B2 | 7/2021 | Paczkowski et al. |
| 11,353,448 B2 | 6/2022 | Xue et al. |
| 11,493,508 B2 | 11/2022 | Ng et al. |
| 11,525,783 B2 | 12/2022 | Tsiomplikas et al. |
| 11,661,619 B2 | 5/2023 | Paczkowski et al. |
| 11,702,687 B2 | 7/2023 | Fan et al. |
| 11,753,743 B2 | 9/2023 | Fan et al. |
| 2001/0016320 A1 | 8/2001 | He et al. |
| 2002/0090649 A1 | 7/2002 | Chan et al. |
| 2002/0100714 A1 | 8/2002 | Staats |
| 2002/0131974 A1 | 9/2002 | Segal |
| 2002/0146745 A1 | 10/2002 | Natan et al. |
| 2003/0013091 A1 | 1/2003 | Dimitrov |
| 2003/0027342 A1 | 2/2003 | Sheridan et al. |
| 2003/0068637 A1 | 4/2003 | Duffy et al. |
| 2003/0082601 A1 | 5/2003 | Dill |
| 2003/0087289 A1 | 5/2003 | Zuzan et al. |
| 2003/0096232 A1 | 5/2003 | Kris et al. |
| 2003/0104486 A1 | 6/2003 | Selvan |
| 2003/0127610 A1 | 7/2003 | Gallagher |
| 2003/0153023 A1 | 8/2003 | Starzl et al. |
| 2003/0190608 A1 | 10/2003 | Blackburn |
| 2003/0190689 A1 | 10/2003 | Crosby et al. |
| 2004/0092032 A1 | 5/2004 | Winkler et al. |
| 2004/0191124 A1 | 9/2004 | Noetzel et al. |
| 2004/0224321 A1 | 11/2004 | Nicolau et al. |
| 2004/0265889 A1 | 12/2004 | Durham et al. |
| 2005/0032144 A1 | 2/2005 | Lombardi et al. |
| 2005/0142033 A1 | 6/2005 | Glezer et al. |
| 2005/0148023 A1 | 7/2005 | Thadhani et al. |
| 2005/0197311 A1 | 9/2005 | Cooper et al. |
| 2005/0226779 A1 | 10/2005 | Oldham et al. |
| 2006/0165739 A1 | 7/2006 | Komesvarakul et al. |
| 2006/0246475 A1 | 11/2006 | Peterson et al. |
| 2006/0263818 A1 | 11/2006 | Scherer et al. |
| 2006/0286549 A1 | 12/2006 | Sohn et al. |
| 2007/0065809 A1 | 3/2007 | Friedman |
| 2007/0074972 A1 | 4/2007 | Nassef et al. |
| 2007/0122819 A1 | 5/2007 | Wu et al. |
| 2007/0202538 A1 | 8/2007 | Glezer et al. |
| 2007/0243535 A1 | 10/2007 | Harris |
| 2008/0200343 A1 | 8/2008 | Clemens et al. |
| 2008/0207461 A1 | 8/2008 | Ermantraut et al. |
| 2008/0317627 A1 | 12/2008 | Shirai et al. |
| 2009/0017455 A1 | 1/2009 | Kwong et al. |
| 2009/0036324 A1 | 2/2009 | Fan et al. |
| 2009/0053732 A1 | 2/2009 | Vermesh et al. |
| 2009/0098541 A1 | 4/2009 | Southern et al. |
| 2009/0137413 A1 | 5/2009 | Mehta et al. |
| 2009/0227043 A1 | 9/2009 | Huang |
| 2010/0009335 A1 | 1/2010 | Joseph et al. |
| 2010/0086925 A1 | 4/2010 | Lee et al. |
| 2010/0152054 A1 | 6/2010 | Love et al. |
| 2010/0213063 A1 | 8/2010 | Zenhausern et al. |
| 2010/0279882 A1 | 11/2010 | Ronaghi et al. |
| 2010/0297145 A1 | 11/2010 | Tsujikawa et al. |
| 2011/0034908 A1 | 2/2011 | Hyde et al. |
| 2011/0048952 A1 | 3/2011 | Van Pelt et al. |
| 2011/0177537 A1 | 7/2011 | Nissum et al. |
| 2011/0224913 A1 | 9/2011 | Cui et al. |
| 2012/0015824 A1 | 1/2012 | Love et al. |
| 2012/0156675 A1 | 6/2012 | Lueerssen et al. |
| 2012/0316074 A1 | 12/2012 | Saxonov |
| 2013/0008144 A1 | 1/2013 | Gallagher et al. |
| 2013/0274117 A1 | 10/2013 | Church et al. |
| 2013/0338047 A1 | 12/2013 | Love et al. |
| 2014/0044641 A1 | 2/2014 | Toporik et al. |
| 2014/0128281 A1 | 5/2014 | Zhang et al. |
| 2014/0170642 A1 | 6/2014 | Huang et al. |
| 2014/0307931 A1 | 10/2014 | Gierahn et al. |
| 2014/0336072 A1 | 11/2014 | Krishnan et al. |
| 2015/0078999 A1 | 3/2015 | Heath et al. |
| 2015/0086424 A1 | 3/2015 | Putnam et al. |
| 2015/0131889 A1 | 5/2015 | Aragaki |
| 2015/0204862 A1 | 7/2015 | Fan et al. |
| 2015/0204864 A1 | 7/2015 | Fan et al. |
| 2016/0011189 A1 | 1/2016 | Fan et al. |
| 2016/0129445 A1 | 5/2016 | Corey et al. |
| 2016/0160169 A1 | 6/2016 | Paczkowski et al. |
| 2016/0167049 A1 | 6/2016 | Narahara et al. |
| 2016/0238594 A1 | 8/2016 | Xue et al. |
| 2016/0252495 A1 | 9/2016 | Ricicova et al. |
| 2017/0067887 A1 | 3/2017 | Fan et al. |
| 2017/0138942 A1 | 5/2017 | Fan et al. |
| 2018/0105855 A1 | 4/2018 | Paczkowski et al. |
| 2018/0335419 A1 | 11/2018 | Love et al. |
| 2019/0024153 A1 | 1/2019 | Frisen et al. |
| 2019/0144936 A1 | 5/2019 | Gierahn et al. |
| 2019/0195869 A1 | 6/2019 | Fan et al. |
| 2019/0285626 A1 | 9/2019 | Ng et al. |
| 2019/0324028 A1 | 10/2019 | Fan et al. |
| 2019/0376898 A1 | 12/2019 | Tsiomplikas et al. |
| 2020/0166518 A1 | 5/2020 | Mackay et al. |
| 2020/0239926 A1 | 7/2020 | Paczkowski et al. |
| 2021/0388446 A1 | 12/2021 | Abate et al. |
| 2022/0017858 A1 | 1/2022 | Zheng et al. |
| 2022/0057388 A1 | 2/2022 | Fan et al. |
| 2022/0136030 A1 | 5/2022 | Paczkowski et al. |
| 2022/0390446 A1 | 12/2022 | Ng et al. |
| 2023/0052346 A1 | 2/2023 | Tsiomplikas et al. |
| 2023/0138672 A1 | 5/2023 | Paczkowski et al. |
| 2023/0191409 A1 | 6/2023 | Ports et al. |
| 2024/0280573 A1 | 8/2024 | Rong et al. |

FOREIGN PATENT DOCUMENTS

| | | |
|---|---|---|
| CN | 2577283 Y | 10/2003 |
| CN | 1582327 A | 2/2005 |
| CN | 101329276 A | 12/2008 |
| CN | 101484806 A | 7/2009 |
| CN | 102177434 A | 9/2011 |
| CN | 102239149 A | 11/2011 |
| CN | 102690786 A | 9/2012 |
| CN | 103596974 A | 2/2014 |
| CN | 104884605 A | 9/2015 |
| DE | 10127221 A1 | 11/2002 |
| EP | 0404097 A2 | 12/1990 |
| EP | 1816476 A1 | 8/2007 |
| EP | 1907573 B1 | 1/2010 |
| EP | 2336348 A1 | 6/2011 |
| EP | 2427572 B1 | 8/2013 |
| EP | 2414548 B1 | 10/2015 |
| EP | 1451351 B1 | 2/2017 |
| EP | 3241913 A1 | 11/2017 |

(56) References Cited

FOREIGN PATENT DOCUMENTS

| EP | 2820158 | B1 | 1/2018 |
|---|---|---|---|
| EP | 3039158 | B1 | 11/2018 |
| EP | 3480321 | A1 | 5/2019 |
| EP | 3248018 | B1 | 1/2020 |
| EP | 2768972 | B2 | 7/2020 |
| EP | 3262192 | B1 | 9/2020 |
| JP | H1175812 | A | 3/1999 |
| JP | 2003057236 | A | 2/2003 |
| JP | 2005030927 | A | 2/2005 |
| JP | 2005517174 | A | 6/2005 |
| JP | 2007535669 | A | 12/2007 |
| JP | 2007536512 | A | 12/2007 |
| JP | 2010066146 | A | 3/2010 |
| JP | 2010533869 | A | 10/2010 |
| JP | 2012511155 | A | 5/2012 |
| JP | 2015533079 | A | 11/2015 |
| WO | WO-9311161 | A1 | 6/1993 |
| WO | WO-9628538 | A1 | 9/1996 |
| WO | WO-9911754 | A1 | 3/1999 |
| WO | WO-0124931 | A1 | 4/2001 |
| WO | WO-02077259 | A2 | 10/2002 |
| WO | WO-03048736 | A2 | 6/2003 |
| WO | WO-03067210 | A2 | 8/2003 |
| WO | WO-03073817 | A2 | 9/2003 |
| WO | WO-2005007892 | A1 | 1/2005 |
| WO | WO-2005081867 | A2 | 9/2005 |
| WO | WO-2005090972 | A1 | 9/2005 |
| WO | WO-2005106482 | A1 | 11/2005 |
| WO | WO-2006117541 | A1 | 11/2006 |
| WO | WO-2007014267 | A2 | 2/2007 |
| WO | WO-2007035633 | A2 | 3/2007 |
| WO | WO-2007136724 | A2 | 11/2007 |
| WO | WO-2008016680 | A1 | 2/2008 |
| WO | WO-2009012340 | A2 | 1/2009 |
| WO | WO-2009012343 | A2 | 1/2009 |
| WO | WO-2010042163 | A2 | 4/2010 |
| WO | WO-2010065929 | A2 | 6/2010 |
| WO | WO-2010085275 | A1 | 7/2010 |
| WO | WO-2010117620 | A2 | 10/2010 |
| WO | WO-2012022482 | A1 | 2/2012 |
| WO | WO-2012083225 | A2 | 6/2012 |
| WO | WO-2013033249 | A2 | 3/2013 |
| WO | WO-2013090404 | A2 | 6/2013 |
| WO | WO-2013130674 | A1 | 9/2013 |
| WO | WO-2013148448 | A1 | 10/2013 |
| WO | WO-2014031997 | A1 | 2/2014 |
| WO | WO-2014052989 | A2 | 4/2014 |
| WO | WO-2014201273 | A1 | 12/2014 |
| WO | WO-2015031691 | A1 | 3/2015 |
| WO | WO-2015166768 | A1 | 11/2015 |
| WO | WO-2015168161 | A2 | 11/2015 |
| WO | WO-2016009446 | A2 | 1/2016 |
| WO | WO-2016044227 | A1 | 3/2016 |
| WO | WO-2016057552 | A1 | 4/2016 |
| WO | WO-2016057705 | A1 | 4/2016 |
| WO | WO-2016090148 | A1 | 6/2016 |
| WO | WO-2016090320 | A1 | 6/2016 |
| WO | WO-2016118915 | A1 | 7/2016 |
| WO | WO-2016130704 | A2 | 8/2016 |
| WO | WO-2016138496 | A1 | 9/2016 |
| WO | WO-2016145409 | A1 | 9/2016 |
| WO | WO-2017087873 | A1 | 5/2017 |
| WO | WO-2018049418 | A1 | 3/2018 |
| WO | WO-2018098372 | A1 | 5/2018 |
| WO | WO-2018170412 | A1 | 9/2018 |
| WO | WO-2019213254 | A1 | 11/2019 |
| WO | WO-2020252384 | A1 | 12/2020 |
| WO | WO-2022256720 | A2 | 12/2022 |

OTHER PUBLICATIONS

Anderson, N. L., et al., "The Human Plasma Proteome", Molecular & Cellular Proteomics (Oct. 2002); 1(11): 845-867.

Andrade, J. D., et al., "Protein adsorption and materials biocompatibility: a tutorial review and suggested hypotheses", Biopolymers/Non-Exclusion HPLC (2005): 1-63.

[Author Unknown] "CodePlex", Isoplexis (2020) [online] URL: https://offers.thescientist.com/hubfs/downloads/TS/TS_Isoplexis_2020/IsoPiexis_CodePiex_eBook/IsoPlexisCodePiexEbookfinaljrck.pdf; 12 pages.

Arenkov, P., et al., "Protein microchips: use for immunoassays and enzymatic reactions", Analytical Biochemistry (2000); 278(2): 123-131.

Armstrong, B., et al., "Suspension arrays for high throughput, multiplexed single nucleotide polymorphism genotyping", Cytometry: The Journal of the International Society for Analytical Cytology (2000); 40(2): 102-108.

Ashton, H., et al., "Smoking and carboxhemoglobin", Lancet (1973); 302(7833): 857-858.

Bailey, R. C., et al., "DNA-Encoded Antibody Libraries: A Unified Platform for Multiplexed Cell Sorting and Detection of Genes and Proteins", Journal of the American Chemical Society (Feb. 2007); 129(7): 1959-1967.

Baines, A. T., et al., "Inhibition of RAS for cancer treatment: the search continues", Future Medicinal Chemistry (Oct. 2011); 3(14): 1787-1808.

Balaban, N. Q., et al., "Bacterial persistence as a phenotypic switch", Science (2004); 305(5690): 1622-1625.

BD Biosciences, "Purified Mouse Anti-Human IL-2", BD Pharmingen Technical Data Sheet (2007); [online] http://www.bdbiosciences.com/ptProduct.jsp?prodid=6725; 1 page.

BD Biosciences, "Technical data sheet: Purified mouse anti-human IL-2", BD Pharmingen (2003); [online] http://www.bdbiosciences.com/ds/pm/tds/555051.pdf; 2 pages.

Becker, C. F. W., et al., "Direct readout of protein-protein interactions by mass spectrometry from protein-DNA microarrays", Angewandte Chemie International Edition (2005); 44(46): 7635-7639.

Bendall, S. C., et al., "From single cells to deep phenotypes in cancer", Nature Biotechnology (2012); 30(7): 639-647. DOI: 10.1038/nbt.2283.

Bendall, S. C., et al., "Single-cell mass cytometry of differential immune and drug responses across a human hematopoietic continuum", Science (May 6, 2011); 332(6030): 687-696.

Bernard, A., et al., "Micromosaic immunoassays", Analytical Chemistry (2001); 73(1): 8-12.

Betensky, R. A., et al., "Influence of unrecognized molecular heterogeneity on randomized clinical trials", Journal of Clinical Oncology (2002); 20(10): 2495-2499.

Boozer, C., et al., "DNA directed protein immobilization on mixed ssDNA/oligo (ethylene glycol) self-assembled monolayers for sensitive biosensors", Analytical Chemistry (2004); 76(23): 6967-6972.

Boozer, C., et al., "DNA-Directed Protein Immobilization for Simultaneous Detection of Multiple Analytes by Surface Plasmon Resonance Biosensor," Analytical Chemistry (2006); 78(5): 1515-1519.

Bose, S., et al., "Scalable microfluidics for single-cell RNA printing and sequencing", Genome Biology (2015); 16(12): 1-16.

Brentjens, R. J., et al., "Safety and persistence of adoptively transferred autologous CD19-targeted T cells in patients with relapsed or chemotherapy refractory B-cell leukemias", Blood, The Journal of the American Society of Hematology (2011); 118(18): 4817-4828.

Breslauer, D. N., et al., "Microfluidic-based systems biology", Molecular Biosystems (2006); 2(2): 97-112.

Bunimovich, Y. L., et al., "Quantitative Real-Time Measurements of DNA Hybridization with Alkylated Nonoxidized Silicon Nanowires in Electrolyte Solution", Journal of the American Chemical Society (2006); 128(5): 16323-16331.

Campbell, R. E., et al., "A monomeric red fluorescent protein", Proceedings of the National Academy of Sciences (Jun. 2002); 99(12): 7877-7882.

Cardoso, A. A., et al., "An improved panning technique for the selection of CD34+ human bone marrow hematopoietic cells with high recovery of early progenitors", Experimental Hematology (1995); 23(5): 407-412.

(56) References Cited

OTHER PUBLICATIONS

Chattopadhyay, P., et al., "Single-cell technologies for monitoring immune systems", Nature Immunology (2014); 15(2): 128-135.
Chen, G., et al., "Discordant protein and mRNA expression in lung adenocarcinomas", Molecular & Cellular Proteomics (2002); 1(4): 304-313.
Chen, J., et al., "Plasma proteome of severe acute respiratory syndrome analyzed by two-dimensional gel electrophoresis and mass spectrometry", Proceedings of the National Academy of Sciences (2004); 101(49): 17039-17044.
Chen, D. S., et al., "Marked Differences in Human Melanoma Antigen-Specific T Cell Responsiveness after Vaccination Using a Functional Microarray," PLoS Medicine (2005); 2(10): 1018-1030.
Chen, S., et al., "Multiplexed analysis of glycan variation on native proteins captured by antibody microarrays", Nature Methods (2007); 4(5): 437-444.
Chen, X., et al., "Microfluidic Devices Targeting Blood Cell Lysis", On-Chip Pretreatment of Whole Blood by Using MEMS Technology (2012): 64-83.
Cheong, R., et al., "Using a microfluidic device for high-content analysis of cell signaling", Science Signaling (2009); 19 pages.
Choi, J., et al., "Immuno-hybridization chain reaction for enhancing detection of individual cytokine-secreting human peripheral mononuclear cells", Analytical Chemistry (Sep. 1, 2011); 83(17): 6890-6895.
Chou, C. F., et al., "Sorting biomolecules with microdevices", Electrophoresis (2000); 21(1): 81-90.
Coussens, L. M., et al., "Inflammation and cancer", Nature (2002); 420(6917): 860-867.
Crowley, T. A., et al., "Isolation of plasma from whole blood using planar microfilters for lab—On-a-chip applications", Lab on a Chip (2005); 5(9): 922-929.
Dandy, D. S., et al., "Array feature size influences nucleic acid surface capture in DNA microarrays," Proceedings of the National Academy of Sciences (2007); 104(20): 8223-8228.
Das, S., et al., "A General Synthetic Approach for Designing Epitope Targeted Macrocyclic Peptide Ligands", Angewandte Chemie International Edition (2015); 54(45): 13219-13224.
Dayhoff, M.O., et al., "22 a Model of Evolutionary Change in Proteins", Atlas of Protein Sequence and Structure, National Biomedical Research Foundation (1978); 5(3): 345-358.
De Marzo, A. M., et al., "Inflammation in prostate carcinogenesis", Nature Reviews Cancer (2007); 7(4): 256-269.
Degenaar, P., et al., "A method for micrometer resolution patterning of primary culture neurons for SPM analysis", The Journal of Biochemistry (2001); 130(3): 367-376.
Dehqanzada, Z. A., et al., "Assessing serum cytokine profiles in breast cancer patients receiving a HER2/neu vaccine using Luminex technology", SSO 58th Annual Cancer Symposium, Abstracts: Poster Presentations (2005); 12: S47-S49.
Delamarche, E., et al., "Patterned delivery of immunoglobulins to surfaces using microfluidic networks", Science (1997); 276(5313): 779-781.
Deyle, K. M., et al., "Protein-targeting strategy used to develop a selective inhibitor of the E17K point mutation in the PH domain of Akt1", Nature Chemistry (May 2015); 7(5): 455-462.
Dirks, R. M., et al., Paradigms for computational nucleic acid design, Nucleic Acids Research (2004); 32(4): 1392-1403.
Downward, J., "Targeting RAS Signalling Pathways in Cancer Therapy", Nature Reviews (Jan. 2003); 3(1): 11-22.
Elitas, M., et al., "A Microchip Platform for Interrogating Tumor-Macrophage Paracrine Signaling at the Single-cell Level", Lab on a Chip (2014); 11 pages.
Engvall, E., et al., "Enzyme-linked immunosorbent assay, Elisa. 3. Quantitation of specific antibodies by enzyme-labeled anti-immunoglobulin in antigen-coated tubes", The Journal of Immunology (1972); 109: 129-135.
Erickson, D., et al., "Modeling of DNA hybridization kinetics for spatially resolved biochips", Analytical Biochemistry (2003); 317(2): 186-200; 2 pages.

Eyer, K., et al., "Implementing Enzyme-Linked Immunosorbent Assays on a Microfluidic Chip to Quantify Intracellular Molecules in Single Cells", Analytical Chemistry (2013); 85(6): 3280-3287.
Fainerman, V. B., et al., "Adsorption of surfactants and proteins at fluid interfaces", Colloids and Surfaces (1998); 143: 141-165.
Fan, R., et al., "Integrated barcode chips for rapid, multiplexed analysis of proteins in microliter quantities of blood", Nature Biotechnology (2008); 26(12): 1373-1378.
Fujii, K., et al., "Clinical-scale high-throughput human plasma proteome analysis: lung adenocarcinoma", Proteomics (2005); 5(4): 1150-1159.
Fung, Y. C., "Stochastic flow in capillary blood vessels", Microvascular Research (1973); 5(1): 34-48.
Galbraith, W., et al., "Remapping disparate images for coincidence", Journal of Microscopy (1993); 172(2): 163-176.
Gao, Y., "A Fluorescent Probe Used in Detection of Tumor Marker and Targeted Photodynamic Therapy", Master Thesis, School of Chemistry, Chemical Engineering and Materials Science, Shandong Normal University (Apr. 2011); 63 pages with English Abstract.
Gavrieli, Y., et al., "Identification of programmed cell death in situ via specific labeling of nuclear DNA fragmentation", The Journal of Cell Biology (1992); 119(3): 493-501.
Gorelik, E., et al., "Multiplexed immunobead-based cytokine profiling for early detection of ovarian cancer", Cancer Epidemiology Biomarkers & Prevention (2005); 14(4): 981-987.
Green, B. D., et al., "Capturing the uncultivated majority", Current Opinion in Biotechnology (2006); 17(3): 236-240.
Groves, T., et al., "In vitro maturation of clonal CD4+CD8+ cell lines in response to TCR engagement", Journal of Immunology (1995); 154(10): 5011-5022.
Guan, M., et al., "Recombinant protein-based enzyme-linked immunosorbent assay and immunochromatographic tests for detection of immunoglobulin G antibodies to severe acute respiratory syndrome (SARS) coronavirus in SARS patients", Clinical and Diagnostics Laboratory Immunology (2004); 11(2): 287-291.
Hainfeld, J. F., et al., "Silver and Gold-Based Autometallography of Nanogold", Gold and Silver Staining, CRC Press, Washington, DC (2002); Ch. 3: 29-46.
Han, Q., et al., "Multidimensional analysis of the frequencies and rates of cytokine secretion from single cells by quantitative microengraving", Lab on a Chip (Jun. 7, 2010); 10(11): 1391-1400.
Han, Q., et al., "Polyfunctional responses by human T cells result from sequential release of cytokines", Proceedings of the National Academy of Sciences (Jan. 31, 2012); 109(5): 1607-1612.
Harju, S., et al., "Rapid isolation of yeast genomic DNA: Bust n' Grab", BMC Biotechnology (2004); 4: 1-6.
Heath, J. R., et al., "Nanotechnology and cancer", Annual Review of Medicine (2007); 59(1): 251-265.
Hein, J., "Unified Approach to Alignment and Phylogenes", Methods in Enzymology (1990); 183: 626-645.
Henderson, M. A., et al., "Chimeric antigen receptor-redirected T cells display multifunctional capacity and enhanced tumor-specific cytokine secretion upon secondary ligation of chimeric receptor", Immunotherapy (2013); 5(6): 577-590.
Henshall, M., et al., "Assay: Validating biomarkers with VeraCode", Genetic Engineering & Biotechnology News (2007); 27(17); 7 pages.
Higgins, D. G., et al., "Fast and sensitive multiple sequence alignments on a microcomputer", Bioinformatics (1989); 5(2): 151-153.
Holland, P. M., et al., "Detection of specific polymerase chain reaction product by utilizing the 5'→3' exonuclease activity of Thermus aquaticus DNA polymerase", Proceedings of the National Academy of Sciences (1991); 88(16): 7276-7280.
Holliger, P., et al., "Diabodies": small bivalent and bispecific antibody fragments, Proceedings of the National Academy of Sciences (Jul. 1993); 90(14): 6444-6448.
Hong, J. W., et al., "A nanoliter-scale nucleic acid processor with parallel architecture", Nature Biotechnology (2004); 22(4): 435-439.
Hong, J. W., et al., "Integrated nanoliter systems", Nature Biotechnology (2003); 21(10): 1179-1183.

(56) References Cited

OTHER PUBLICATIONS

Hsieh, S. Y., et al., "Systematical evaluation of the effects of sample collection procedures on low-molecular-weight serum/plasma proteome profiling", Proteomics (2006); 6(10): 3189-3198.
Huang, R. P., "Detection of Multiple Proteins in an Antibody-based Protein Microarray System", Journal of Immunological Methods (Sep. 2001); 255(1-2): 1-13.
Huang, B., et al., "Counting low-copy number proteins in a single cell", Science (2007); 315(5808): 81-84.
Huang, L. R., et al., "Continuous Particle Separation Through Deterministic Lateral Displacement", Science (2004); 304(5673): 987-990.
Huber, M., et al., "Comparison of proteomic and genomic analyses of the human breast cancer cell line T47D and the antiestrogen-resistant derivative T47D-r", Molecular & Cellular Proteomics (2004); 3(1): 43-55.
Hughes, A. J., et al., "Single-Cell Western Blotting", Nature Methods (Jul. 2014,); 11(7): 749-755.
Hughes, T., et al., "Molecular Monitoring of Chronic Myeloid Leukemia", Seminars in Hematology (2003); 40(2): 62-68.
Iannone, M. A., et al., "Multiplexed single nucleotide polymorphism genotyping by oligonucleotide ligation and flow cytometry", Cytometry (1999); 39(2): 131-140.
Inerowicz, H.D., et al., "Multiprotein immunoassay arrays fabricated by microcontact printing", Langmuir (2002); 18(13): 5263-5268.
Jeon, S. R., et al., "Protein-surface interactions in the presence of polyethylene oxide: II. Effect of protein size", Journal of Colloid and Interface Science (1991); 142(1): 159-166.
Jeon, S. I., et al., "Protein—surface interactions in the presence of polyethylene oxide: I. Simplified theory", Journal of Colloid and Interface Science (1991); 142(1): 149-158.
Kim, K. J., et al., "Establishment and characterization of BALB/c lymphoma lines with B cell properties", The Journal of Immunology (1979); 122(2): 549-554.
Kiyonaka, S., et al., "Semi-wet peptide/protein array using supramolecular hygrogel", Nature Materials (2004); 3(1): 58-64.
Kochenderfer, J., et al., "B-cell depletion and remissions of malignancy along with cytokine-associated toxicity in a clinical trial of anti-CD19 chimeric-antigen-receptor-transduced T cells", Blood (2012); 119(12): 2709-2720.
Kozlov, I. A., et al., "Efficient strategies for the conjugation of oligonucleotides to antibodies enabling highly sensitive protein detection", Biopolymers (2004); 73(5): 621-630.
Krzywinski, M., et al., "Circos: An information aesthetic for comparative genomics", Genome Research (2009); 19(9): 1639-1645.
Kwak, M., et al. "Single-cell protein secretomic signatures as potential correlates to tumor cell lineage evolution and cell-cell interaction", Frontiers in Oncology (Feb. 2013); 3(Article 10): 1-8.
Kwon, Y., et al., "Antibody arrays prepared by cutinase-mediated immobilization on self-assembled monolayers", Analytical Chemistry (2004); 76(19): 5713-5720.
Kwong, K. Y., et al., "Synchronous global assessment of gene and protein expression in colorectal cancer progression", Genomics (2005); 86(2): 142-158.
Kyte, J., et al., "A simple method for displaying the hydropathic character of a protein", Journal of Molecular Biology (1982); 157(1): 105-132.
Lamb, J., et al., "The Connectivity Map: using gene-expression signatures to connect small molecules, genes, and disease", Science (2006); 313(5795): 1929-1935.
Lambeck, A. J. A., et al., "Serum cytokine profiling as a diagnostic and prognostic tool in ovarian cancer: a potential role or interleukin 7", Clinical Cancer Research (2007); 13(8): 2385-2391.
Lange, S. A., et al., "Microcontact printing of DNA molecules", Analytical Chemistry (2004); 76(6): 1641-1647.
Lathrop, J. T., et al., "Therapeutic potential of the plasma proteome", Current Opinion in Molecular Therapeutics (2003); 5(3): 250-257.
Lecault, V., et al., "High-throughput analysis of single hematopoietic stem cell proliferation in microfluidic cell culture arrays", Nature Methods (2011); 8(7): 581-586.
Lee, S. S., et al., "Quantitative and dynamic assay of single cell chemotaxis", Integrative Biology (2012); 4(4): 381-390.
Lee, H. J., et al., "SPR Imaging Measurements of 1-D and 2-D DNA Microarrays Created from Microfluidic Channels on Gold Thin Films", Analytical Chemistry (2001); 73(22): 5525-5531.
Lin, B., et al., "Evidence for the Presence of Disease-Perturbed Networks in Prostate Cancer Cells by Genomic and Proteomic Analyses: A Systems Approach to Disease", Cancer Research (2005); 65(8): 3081-3091.
Lin, W., et al., "A cytokine-mediated link between innate immunity, inflammation, and cancer", Journal of Clinical Investigation (2007); 117(5): 1175-1183.
Liotta, A. A., et al., "Protein microarrays: meeting analytical challenges for clinical applications", Cancer Cell (2003); 3(4): 317-325.
Liu, X., et al., "Photopatterning of antibodies on biosensors", Bioconjugate Chemistry (2000); 11(6): 755-761.
Love, J. C., et al., "A microengraving method for rapid selection of single cells producing antigenspecific antibodies", Nature Biotechnology (2006); 24(6): 703-707.
Lu, Y., et al., "High-throughput Secretomic Analysis of Single Cells to Assess Functional Cellular Heterogeneity," Analytical Chemistry (2013); 85(4): 33 pages.
Ivanova, E. P., et al., "Polymer Microstructures Fabricated via Laser Ablatoin Used for Multianalyte Protein Microassay", Langmuir (2002); 18(24): 9539-9546.
Ma, C. et al., "A clinical microchip for evaluation of single immune cells reveals high functional heterogeneity in phenotypically similar T cells", Nature Medicine (2011); 17(6): 738-743.
Ma, C., et al., "Multifunctional T-cell analyses to study response and progression in adoptive cell transfer immunotherapy", Cancer Discovery (Apr. 2013); 3(4): 418-429.
Macbeath, G., et al., "Printing proteins as microarrays for high-throughput function determination", Science (2000); 289(5485): 1760-1763.
Madoz-Gurpide, J., et al., "Protein based microarrays: A tool for probing the proteome of cancer cells and issues", Proteomics (2001); 1(10): 1279-1287.
Maïno, N., et al., "A microfluidic platform towards automated multiplexed in situ sequencing", Scientific Reports (2019); 9(1): 3542; 10 pages.
Martin, M., et al., "Molecular biology of breast cancer", Clinical and Translational Medicine (2006); 8(1): 7-14.
Mellinghoff, I. K., et al., "Molecular determinants of the response of glioblastomas to EGFR kinase inhibitors", New England Journal of Medicine (2006); 353(19): 2012-2024.
Michel, B., et al., "Printing meets lithography: Soft approaches to high-resolution patterning", Chimia (2002); 56(10): 527-542.
Michor, F., et al., "The origins and implications of intratumor heterogeneity", Cancer Prevention Research (Nov. 2010); 3(11): 1361-1364.
Mischel, P. S., et al., "DNA-microarray analysis of brain cancer: molecular classification for therapy", Nature Reviews Neuroscience (Oct. 2004); 5(10): 782-792.
Murai, M., et al., "Vacuolar membrane lesions induced by a freeze-thaw cycle in protoplasts isolated from deacclimated tubers of Jerusalem artichoke (Helianthus tuberosus L.)", Plant and Cell Physiology (1998); 39(1): 87-96.
Myers, E. W., et al., "Optimal alignments in linear space", Bioinformatics (1988); 4(1): 11-17.
Nagrath, S., et al., "Isolation of Rare Circulating Tumour Cells in Cancer Patients by Microchip Technology", Nature (Dec. 20, 2007); 450(7173): 1235-1239.
Nam, J., et al., "Nanoparticle-based bio-bar codes for the ultrasensitive detection of proteins", Science (2003); 301(5641): 1884-1886.
Nam, J., et al., "Supporting Material—Nanoparticle-based bio-bar codes for the ultrasensitive detection of proteins", Science (2003); 301(5641): 1884-1886; 12 pages.
Nathanson, D. A., et al., "Co-targeting of convergent nucleotide biosynthetic pathways for leukemia eradication", Journal of Experimental Medicine (2014); 211(3): 473-486.

(56) References Cited

OTHER PUBLICATIONS

Needleman, S. B., et al., "A general method applicable to the search for similarities in the amino acid sequence of two proteins", Journal of Molecular Biology (1970); 48(3): 443-453.
Niemeyer, C. M., "Functional devices from DNA and proteins", Nano Today (2007); 2(2): 42-52.
Niemeyer, C. M., et al., "Immuno-PCR: high sensitivity detection of proteins by nucleic acid amplification", Trends in Biotechnology (2005); 23(4): 208-216.
Olanrewaju, A., et al., "Capillary microfluidics in microchannels: from microfluidic networks to capillaric circuits", Lab on a Chip (2018); 18(16): 2323-2347.
Ostrem, J. M., et al., "K-Ras(G12C) inhibitors allosterically control GTP affinity and effector interactions", Nature (Nov. 28, 2013); 14 pages.
Ottesen, E. A., et al., "Microfluidic digital PCR enables multigene analysis of individual environmental bacteria", Science (2006); 314(5804): 1464-1467.
Pal, M., et al., "Differential Phosphoprotein Mapping in Cancer Cells Using Protein Microarrays Produced from 2-D Liquid Fractionation", Analytical Chemistry (2006); 78(3): 702-710.
Park, S. J., et al., "Array-Based Electrical Detection of DNA with Nanoparticle Probes", Science (2002); 295(5559): 1503-1506.
Pearson, W. R., et al., "Improved tools for biological sequence comparison", Proceedings of the National Academy of Sciences (1988); 85(8): 2444-2448.
Peluso, P., et al., "Optimizing antibody immobilization strategies for the construction of protein arrays", Analytical Biochemistry (2003); 312(2): 113-124.
Petersen, K. F., et al., "Mechanism of troglitazone action in type 2 diabetes", Diabetes (2000); 49(5): 827-831.
Phillips, T. M., "Rapid analysis of inflammatory cytokines in cerebrospinal fluid using chip-based immunoaffinity electrophoresis", Electrophoresis (2004); 25(10-11): 1652-1659.
Picelli, S., et al., "Single-cell RIMA-sequencing: The future of genome biology is now", RNA Biology (2017); 14(5): 637-650.
Pirrung, M. C., "How to make a DNA chip", Angewandte Chemie International Edition (2002); 41(8): 1276-1289.
Pluckthun, A., "Antibodies from *Escherichia coli*", The Pharmacology of Monoclonal Antibodies, Springer-Verlag (1994); Chapter 11: pp. 269-315.
Prados, M., et al., "Temozolomide + OSI-774", University of California San Francisco, Brain Tumor Research Center (2003); 29 pages.
Prime, K. L., et al., "Self-assembled organic monolayers: model systems for studying adsorption of proteins at surfaces", Science (1991); 252(5009): 1164-1167.
Prime, K. L., et al., "Adsorption of proteins onto surfaces containing end-attached oligo(ethylene oxide): a model system using self-assembled monolayers", Journal of the American Chemical Society (1993); 115(23): 10714-10721.
Qiao, D., et al., "Applications of Barcode Microfluidic Technology in Detecting Secreted Proteins", Current Biotechnology (2012); 2(5): 323-327.
Quake, S. R., et al., (2000) "From Micro- to Nanofabrication with Soft Materials", Science (2000); 290(5496): 1536-1540.
Radich, J. P., et al., "Gene expression changes associated with progression and response in chronic myeloid leukemia", Proceedings of the National Academy of Sciences (2006); 103(8): 2794-2799.
Ramsden, J. J., "Puzzles and Paradox in Protein Adsorption", Chemical Society Reviews (1995); 24(1): 73-78.
Rich, J. N., et al., "Phase II trial of gefitinib in recurrent glioblastoma," Journal of Clinical Oncology (2004); 22(1): 133-142.
Robinson, D. F., "Comparison of Labeled Trees with Valency Three", Journal of Combinatorial Theory (1971); 11: 105-119.
Rodriques, S. G., et al., "Slide-seq: A scalable technology for measuring genome-wide expression at high spatial resolution", Science (2019); 363(6434): 1463-1467.
Rowat, A. C., et al., "Tracking lineages of single cells in lines using a microfluidic device", Proceedings of the National Academy of Sciences (2009); 106(43): 18149-18154.
Sachdeva, N., et al., "Cytokine quantitation: technologies and applications", Front Biosci (2007); 12: 4682-4695.
Saitou, N., et al., "The Neighbor-joining Method: A New Method for Reconstructing Phylogenetic Trees", Neighbor-joining Method, Molecular Biology and Evolution (1987); 4(4): 406-425.
Sano, T., et al., "Immuno-PCR: very sensitive antigen detection by means of specific antibody-DNA conjugates", Science (1992); 258(5079): 120-122.
Sarkar, A., et al., "Microfluidic Probe for Single-cell Analysis in Adherent Tissue Culture", Nature Communications (Mar. 5, 2014); 5: 1-8.
Scatchard, G., "The Attractions of Proteins for Small Molecules and Ions", Proteins and Small Molecules, Annals of the New York Academy of Sciences (1949); 51(4): 660-672.
Schena, M., et al., "Quantitative monitoring of gene expression patterns with a complementary DNA microarray", Science (1995); 270(5235): 467-470.
Schubbert, S., et al., "Hyperactive Ras in developmental disorders and cancer", Nature Reviews (Apr. 2007); 7(4); 14 pages.
Schweitzer, B., et al., "Multiplexed protein profiling on microarrays by rolling-circle amplification", Nature Biotechnology (2002); 20(4): 359-365.
Sedgwick, H., et al., "Lab-on-a-chip technologies for proteomic analysis from isolated cells", A Journal of the Royal Society (2008); 5(2): S123-S130.
Seigel, R. R., et al., "On-line detection of nonspecific protein adsorption at artificial surfaces", Analytical Chemistry (Aug. 1997); 69(16): 3321-3328.
Shehadul Islam, M., et al., "A review on macroscale and microscale cell lysis methods", Micromachines (2017); 8(3): 83; 27 pages.
Shi, Q., et al., "Single-cell Proteomic Chip for Profiling Intracellular Signaling Pathways in Single Tumor Cells", PNAS (Jan. 10, 2012); 109(2): 419-424.
Shin, Y. S., et al., "Protein signaling networks from single cell fluctuations and information theory profiling", Biophysical Journal (May 18, 2011); 100(10): 2378-2386.
Shin, Y., et al., "Chemistries for Patterning Robust DNA MicroBarcodes Enable Multiplex Assays of Cytoplasm Proteins from Single Cancer Cells", ChemPhysChem (2010); 11(14): 3063-3069.
Shin, Y., et al., "Supporting Information: Chemistries for Patterning Robust DNA MicroBarcodes Enable Multiplex Assays of Cytoplasm Proteins from Single Cancer Cells", ChemPhysChem (2010); 11(14): 3063-3069; 10 pages.
Sia, S. K., et al., "Microfluidic devices fabricated in poly(dimethylsiloxane) for biological studies", Electrophoresis (2003); 24(21): 3563-3576.
Smith, T. F., et al., "Comparison of Biosequences", Advances in Applied Mathematics (1981); 2: 482-489.
Soen, Y., et al., "Detection and characterization of cellular immune responses using peptide—MHC microarrays", PLoS Biology (2003); 1(3): 429-438.
Sorger, P. K., "Microfluidics closes in on point-of-care assays", Nature Biotechnology (2008); 26(12): 1345-1346.
Spiro, A., et al., "A Bead-Based Method for Multiplexed Identification and Quantitation of DNA Sequences Using Flow Cytometry", Applied and Environmental Microbiology, American Society for Microbiology (2000); 66(10): 4258-4265.
Ståhl, P. L., et al., "Visualization and analysis of gene expression in tissue sections by spatial transcriptomics", Science (2016); 353(6294): 78-82.
Svanes, K., et al., "Variations in small blood vessel hematocrits produced in hypothermic rats by micro-occlusion", Microvascular Research (1968); 1(2): 210-220.
Taton, T. A., et al., "Scanometric DNA array detection with nanoparticle probes", Science (2000); 289(5485): 1757-1760.
Thirumalapura, N. R., et al., "Lipopolysaccharide microarrays for the detection of antibodies", Journal of Immunological Methods (2005); 298(1-2): 73-81.
Thorsen, T., et al., "Microfluidic large-scale integration", Science (2002); 298(5593): 580-584.

(56) References Cited

OTHER PUBLICATIONS

Thuillier, G., et al., "Development of a low cost hybrid Si/PDMS multi-layered pneumatic microvalve", Microsystem Technologies (2005); 12(1): 180-185.

Tian, Q., et al., "Integrated genomic and proteomic analyses of gene expression in mammalian cells", Molecular & Cellular Proteomics (2004); 3(10): 960-969.

Toner, M., et al., "Blood-on-a-chip", Annual Review of Biomedical Engineering (2005); 7(1): 77-103.

Toriello, N., M., et al., "Integrated microfluidic bioprocessor for single-cell gene expression analysis", Proceedings of the National Academy of Sciences (2008); 105(51): 20173-20178.

Toure, M., et al., "Small-Molecule PROTACS: New Approaches to Protein Degradation", Angewandte Chemie International Edition (2016); 55: 1966-1973.

Treutlein, B., et al., "Reconstructing lineage hierarchies of the distal lung epithelium using single-cell RNA-seq", Nature (2014); 509(7500): 371-375.

Trombetta, J., J., et al., "Preparation of single-cell RNA-seq libraries for next generation sequencing", Current Protocols in Molecular Biology (2014); 107(1): 4.22.1-4.22.17.

Tyrberg, B., et al., "T-cadherin (Cdh13) in association with pancreatic ß-cell granules contributes to second phase insulin secretion", Islets (2011); 3(6): 327-337.

Unger, M. A., et al., "Monolithic microfabricated valves and pumps by multilayer soft lithography", Science (2000); 288(5463): 113-116.

[Author Unknown] "Isolight System Guide", Isoplexis (2018) [online] http://isoplexis.com/wp-contenVuploads/2018/04/Isolight-User-Manual-1.pdf; 24 pages.

U.S. Appl. No. 18/808,943, filed Aug. 19, 2024, by Fan, Rong et al.

Duijn, G. V., et al., "Detection of genetically modified organisms in foods by protein- and DNA-based techniques: bridging the methods", Journal of AOAC International (2002); 85(3): 787-791.

Wacker, R., et al., "DDI-μFIA-A readily configurable microarray-fluorescence immunoassay based on DNA-directed immobilization of proteins", Chembiochem (2004); 5(4): 453-459.

Wang, J., et al., "A self-powered, one-step chip for rapid, quantitative and multiplexed detection of proteins from pinpricks of whole blood", Lab on a Chip (2010); 10(22): 3157-3162.

Wang, D., et al., "Single cell analysis: the new frontier in 'omics'", Trends Biotechnology (Jun. 2010); 28(6): 281-290.

Wegner, G. J., et al., "Fabrication of Histidine-Tagged Fusion Protein Arrays for Surface Plasmon Resonance Imaging Studies of Protein-Protein and Protein-DNA Interactions", Analytical Chemistry (2003); 75: 4740-4746.

Wei, W., et al., "Microchip platforms for multiplex single-cell functional proteomics with applications to immunology and cancer research", Genome Medicine (2013); 12 pages.

Whitesides, G. M., et al., "Soll lithography in biology and biochemistry," Annual Review of Biomedical Engineering (2001); 3: 335-373.

Wilbur, W. J., et al., "Rapid similarity searches of nucleic acid and protein data banks", Proceedings of the National Academy of Sciences (1983); 80(3): 726-730.

Wise, D. R., et al., "Glutamine addiction: a new therapeutic target in cancer", Trends in Biochemical Sciences (Aug. 2010); 35(8): 427-433.

Wysocki, L. J., et al., "Panning for lymphocytes: a method for cell selection", Proceedings of the National Academy of Sciences (1978); 75(6): 2844-2848.

Yamanaka, Y. J., "Single-cell Analysis of the Dynamics and Functional Outcomes of Interactions Between Human Natural Killer Cells and Target Cells", Integrative Biology (Oct. 2012); 4(10): 1175-1184.

Yang, S., et al., "A microfluidic device for continuous, real lime blood plasma separation", Lab on a Chip (2006); 6: 871-880.

Yang, C., et al., "Using a cross-flow microfluidic chip and external crosslinking reaction for monodisperse TPP-chitosan microparticles", Sensors and actuators B (2007); 7 pages.

Yu, Z., et al., "Contextual interactions determine whether the *Drosophila homeodomain* protein, Vnd, acts as a repressor or activator", Nucleic Acids Research (2005); 33(8): 1-12.

Yu, J., et al., "Microfluidics-Based Single-Cell Functional Proteomics for Fundamental and Applied Biomedical Applications", Annual Review of Analytical Chemistry (2014); 7: 275-295.

Yu, Y., et al., "Analysis of the Surface, Secreted, and Intracellular Proteome of Propionibacterium acnes", EuPA Open Proteomics (2015); 9: 1-7.

Yuan, J., et al., "An automated microwell platform for large-scale single cell RNA-seq", Scientific Reports (2016); 6(33883); 10 pages.

Zhang, K., et al., "Sequencing genomes from single cells by polymerase cloning", Nature Biotechnology (Jun. 2006); 24(6): 680-686.

Zhao, Y., et al., "High-Affinity TCRs Generated by Phage Display Provide CD4 T Cells with the Ability to Recognize and Kill Tumor Cell Lines", The Journal of Immunology (2007); 5845-5854.

Zimmermann, M., et al., "Modeling and optimization of high-sensitivity, low-volume microfluidic-based surface immunoassays", Biomedical Microdevices (2005); 7(2): 99-110.

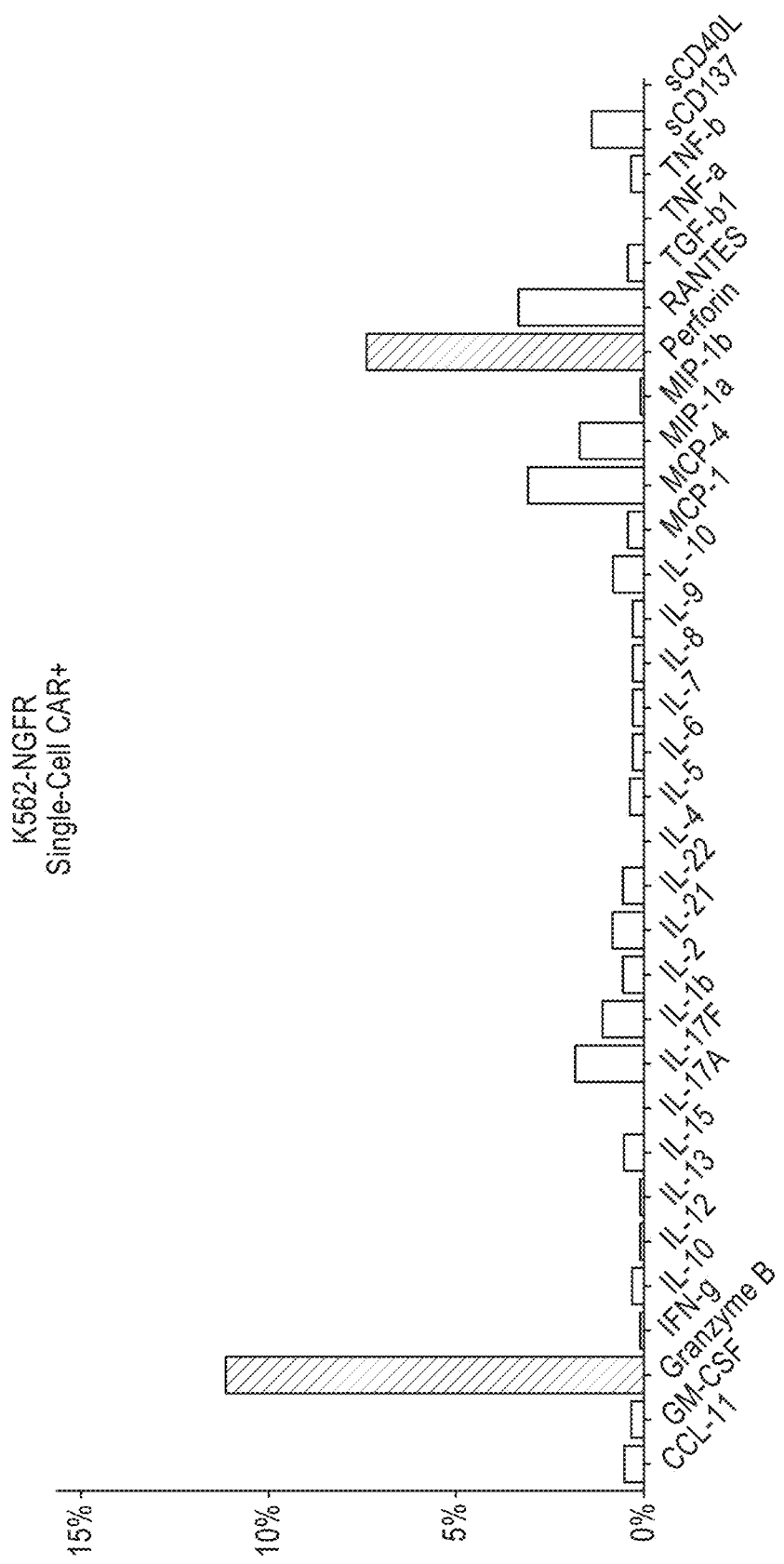

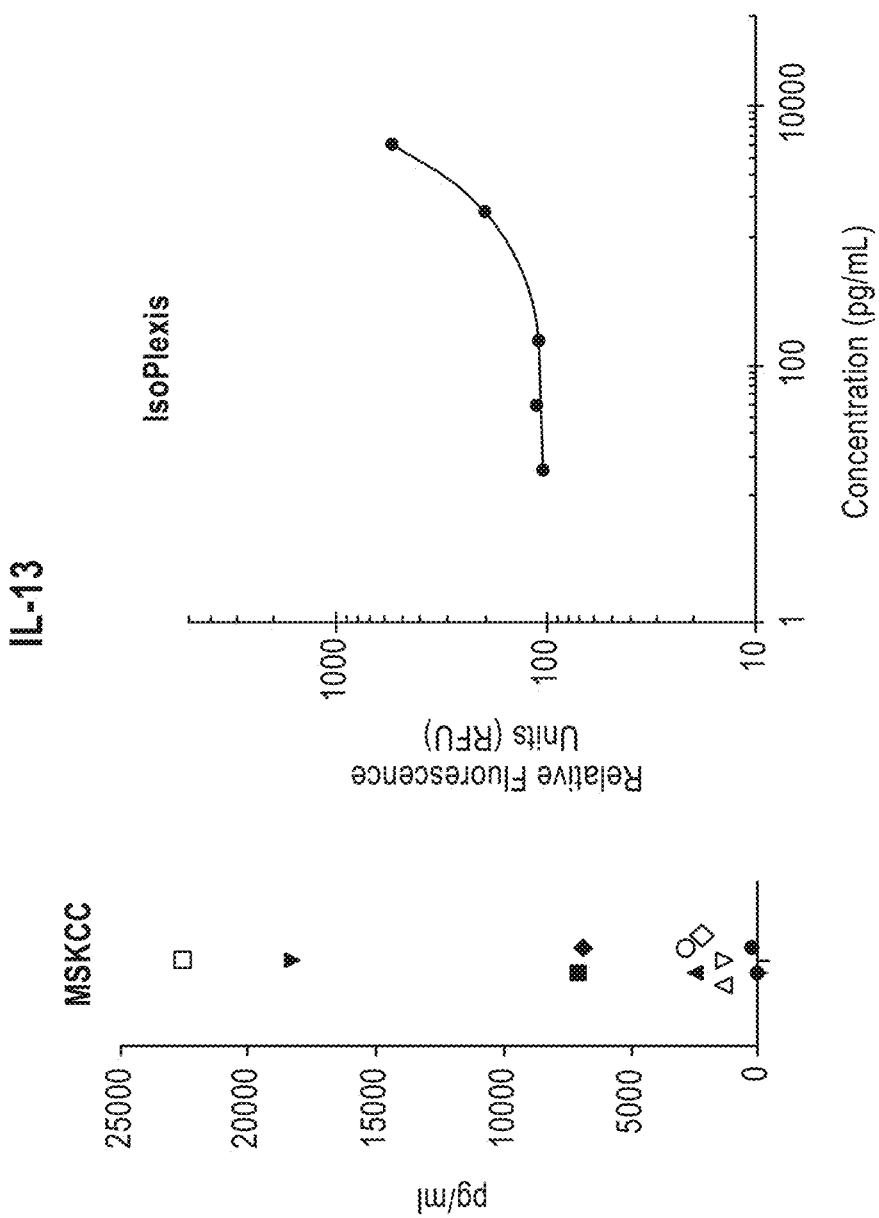

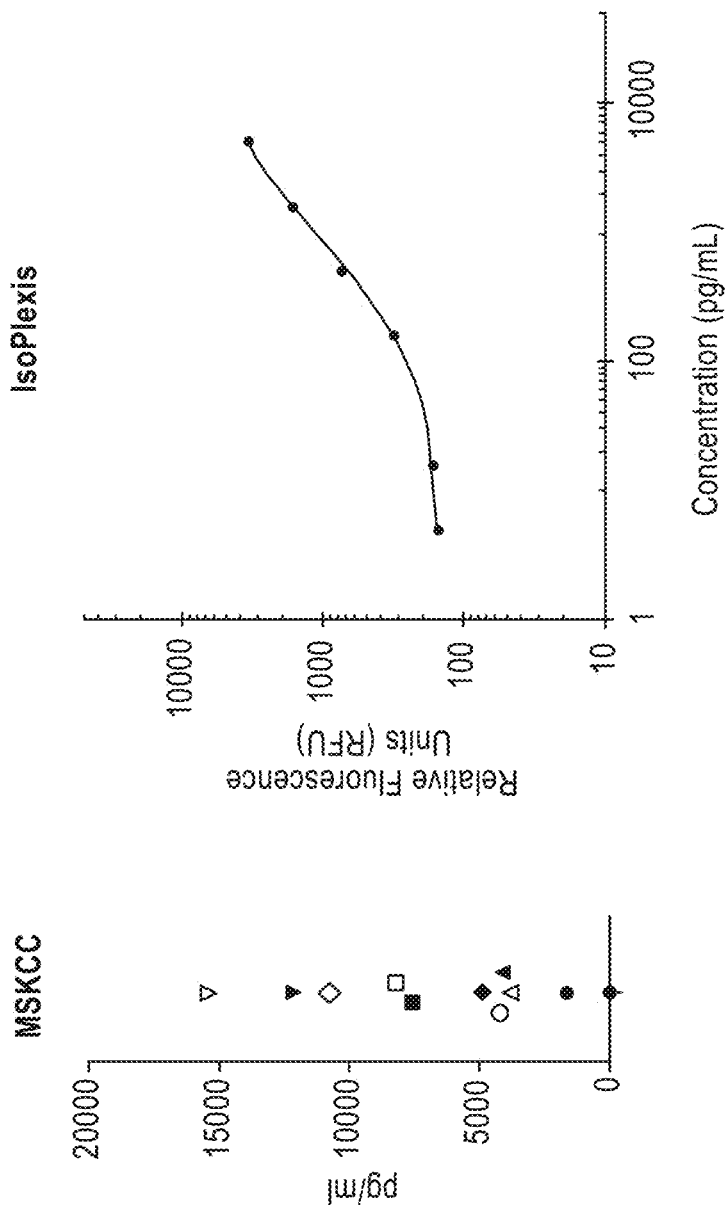

IL-13

IFN-gamma

FIGURE 13A

| NCI Patient | IFNγ, pg/mL | | TNF, pg/mL | | IL-2, pg/mL | |
|---|---|---|---|---|---|---|
| | CD19-positive target | CD19-negative target | CD19-positive target | CD19-negative target | CD19-positive target | CD19-negative target |
| 1* | 8190 | 411 | 448 | <31 | 1156 | 48 |
| 2 | 9850 | 506 | 6250 | <31 | 2002 | 139 |
| 3 | 19 000 | 916 | 9312 | <31 | 1683 | 51 |
| 4 | 27 900 | 944 | 21 895 | <31 | 2768 | 40 |
| 5 | 36 700 | 734 | 21 515 | <31 | 2421 | 32 |
| 6 | 14 800 | 130 | 8288 | <31 | 798 | 44 |
| 7 | 29 300 | 341 | 21 980 | <31 | 1661 | 36 |
| 8 | 9960 | 240 | 9830 | 73 | 1697 | 46 |

FIGURE 13B

| IsoPlexis | LOD SNR>2 | LOD SNR>5 |
|---|---|---|
| IFNγ, pg/mL | 50 | 300 |
| TNF, pg/mL | 300 | 1000 |
| IL-2, pg/mL | 300 | 1000 |

SYSTEM AND METHODS FOR MULTIPLEXED ANALYSIS OF CELLULAR AND OTHER IMMUNOTHERAPEUTICS

RELATED APPLICATIONS

This application is a continuation of U.S. patent application Ser. No. 16/332,627, filed Mar. 12, 2019, which is a national phase filing under 35 U.S.C. § 371 of International PCT Application No. PCT/US2017/051223, filed Sep. 12, 2017, which claims the priority benefit of U.S. Patent Application No. 62/393,612, filed Sep. 12, 2016, U.S. Patent Application No. 62/431,318 filed Dec. 7, 2016, U.S. Patent Application No. 62/480,147, filed Mar. 31, 2017, and U.S. Patent Application No. 62/480,752, filed Apr. 3, 2017, the contents of each of which are herein incorporated by reference in their entirety.

FIELD OF THE DISCLOSURE

The disclosure is directed to molecular biology, and more, specifically, to methods of identifying the contents of the secretome of a subject cell and the use of the secretome for determining the safety and efficacy of the subject cell as a cell-based therapy.

BACKGROUND

There have been long-felt but unmet needs in the art for a system and methods of identifying cells suitable for use in a cellular therapy as well as methods of evaluating the safety and efficacy of these cells ex vivo or in vitro in a highly multiplexed reaction that can simultaneously analyze thousands of single cells from a heterogeneous cell population. The disclosure provides a system and methods to solve these long-felt but unmet needs.

SUMMARY

The systems of the disclosure provide a highly multiplexed method of evaluating the secretome of individual cells in a functionally heterogeneous population following contact with a target cell or a stimulatory agent. Analysis of the composition of the secretome of the subject cell may be used to determine the subject cell's identity, viability, safety and efficacy when used in a cell-based therapy. Cellular therapies may include autologous or allogeneic cells. Cellular therapies may include modified cells, including, but not limited to T-cells that express at least one artificial or chimeric antigen receptor.

The disclosure provides a method of identifying a secretome from a subject cell within a heterogeneous cell population comprising: (a) contacting the subject cell and a target cell or a stimulatory agent in at least one chamber of a plurality of chambers, wherein the chamber is in fluid communication with an antibody panel and wherein the antibody panel is removably attached to the chamber; (b) maintaining the subject cell and the target cell or the stimulatory agent in the chamber under conditions sufficient to permit (1) the subject cell to secrete at least one of a peptide, polypeptide, and protein and (2) at least one antibody of the antibody panel specific for the at least one protein to bind the at least one peptide, polypeptide, or protein, forming at least one of an antibody:secreted peptide, antibody:secreted polypeptide, or an antibody:secreted protein complex; (c) removing the antibody panel from the chamber; and (d) imaging the at least one peptide, polypeptide, or protein, forming at least one of an antibody:secreted peptide, antibody:secreted polypeptide, or an antibody:secreted protein complex, thereby identifying the secretome of the subject cell when the subject cell contacts the target cell or the stimulatory agent.

The disclosure provides a method of identifying a secretome from a subject cell within a heterogeneous cell population comprising: (a) contacting the subject cell and a target cell or a stimulatory agent under conditions sufficient to permit stimulation of the subject cell; (b) introducing the subject cell to at least one chamber of a plurality of chambers, wherein the chamber is in fluid communication with an antibody panel and wherein the antibody panel is removably attached to the chamber; (c) maintaining the subject cell in the chamber under conditions sufficient to permit (1) the subject cell to secrete at least one of a peptide, polypeptide, and protein and (2) at least one antibody of the antibody panel specific for the at least one protein to bind the at least one peptide, polypeptide, or protein, forming at least one of an antibody:secreted peptide, antibody:secreted polypeptide, or an antibody:secreted protein complex; (d) removing the antibody panel from the chamber; and (e) imaging the at least one peptide, polypeptide, or protein, forming at least one of an antibody:secreted peptide, antibody:secreted polypeptide, or an antibody:secreted protein complex, thereby identifying the secretome of the subject cell following contact with the target cell or the stimulatory agent. In certain embodiments, this method further comprises the step of disrupting contact between the subject cell and the target cell or the stimulatory agent. In certain embodiments of this method, the subject cell and the target cell or the stimulatory agent are comprised by a composition and wherein the subject cell and the target cell or the stimulatory agent are in fluid communication. In certain embodiments, including those wherein the subject cell and the target cell or the stimulatory agent are comprised by a composition and wherein the subject cell and the target cell or the stimulatory agent are in fluid communication, the method further comprises the step of depleting the target cell or the stimulatory agent from the composition.

In certain embodiments of the systems and methods of the disclosure, the heterogeneous cell population is a functionally heterogeneous cell population. In certain embodiments, the functionally heterogeneous cell population may comprise at least two cells that produce a secretome in response to a stimulus, wherein the first cell produces a first secretome, wherein the second cell produces a second secretome, and wherein the first secretome and the second secretome are not identical.

Secretomes of the disclosure may comprise one or more peptides, polypeptides, proteins, small molecules, and ions. In certain embodiments, the secretome comprises one or more peptides, polypeptides or proteins. In certain embodiments, the secretome comprises one or more small molecules. In certain embodiments, the secretome comprises one or more ions. When the secretome comprises a small molecule or an ion, detectable labels may be used in addition or in place of antibodies to identify, quantify, or otherwise analyze the small molecule and ions of the secretome.

Secretomes of the disclosure may be released from a subject cell actively or passively. For example, secretomes of the disclosure may be released from a subject cell via a vesicle, an intercellular gap junction and/or a transmembrane channel or pump.

In certain embodiments of the systems and methods of the disclosure, the functionally heterogeneous cell population comprises one or more immune cells. In certain embodiments, the one or more immune cells comprise a T-lymphocyte, a B-lymphocyte, a natural killer (NK) cell, a macrophage, a neutrophil, a mast cell, an eosinophil, or a basophil. In certain embodiments, the T-lymphocyte comprises a naïve T-lymphocyte, an activated T-lymphocyte, an effector T-lymphocyte, a helper T-lymphocyte, a cytotoxic T-lymphocyte, a gamma-delta T-lymphocyte, a regulatory T-lymphocyte, a memory T-lymphocyte, or a memory stem T-lymphocyte. In certain embodiments, the T-lymphocyte expresses a non-naturally occurring antigen receptor. In certain embodiments, the T-lymphocyte expresses a Chimeric Antigen Receptor (CAR).

In certain embodiments of the systems and methods of the disclosure, the functionally heterogeneous cell population comprises one or more immune cells. In certain embodiments, the one or more immune cells comprise a T-lymphocyte, a B-lymphocyte, a natural killer (NK) cell, a macrophage, a neutrophil, a mast cell, an eosinophil, or a basophil. In certain embodiments, the B-lymphocyte comprises a plasmablast, a plasma cell, a memory B-lymphocyte, a regulatory B cell, a follicular B cell, or a marginal zone B cell.

In certain embodiments of the systems and methods of the disclosure, the subject cell is an immune cell. In certain embodiments, the immune cell comprises a T-lymphocyte, a B-lymphocyte, a natural killer (NK) cell, a macrophage, a neutrophil, a mast cell, an eosinophil, or a basophil. In certain embodiments, the T-lymphocyte comprises a naïve T-lymphocyte, an activated T-lymphocyte, an effector T-lymphocyte, a helper T-lymphocyte, a cytotoxic T-lymphocyte, a gamma-delta T-lymphocyte, a regulatory T-lymphocyte, a memory T-lymphocyte, or a memory stem T-lymphocyte. In certain embodiments, the T-lymphocyte expresses a non-naturally occurring antigen receptor. In certain embodiments, the T-lymphocyte expresses a Chimeric Antigen Receptor (CAR).

In certain embodiments of the systems and methods of the disclosure, the subject cell is an immune cell. In certain embodiments, the immune cell comprises a T-lymphocyte, a B-lymphocyte, a natural killer (NK) cell, a macrophage, a neutrophil, a mast cell, an eosinophil, or a basophil. In certain embodiments, the B-lymphocyte comprises a plasmablast, a plasma cell, a memory B-lymphocyte, a regulatory B cell, a follicular B cell, or a marginal zone B cell.

In certain embodiments of the systems and methods of the disclosure, the functionally heterogeneous cell population comprises one or more neuronal cells. In certain embodiments, the one or more neuronal cells comprise a neuron, a glial cell, an astrocyte, a satellite cell, or an enteric glial cell.

In certain embodiments of the systems and methods of the disclosure, the subject cell is a neuronal cell. In certain embodiments, the neuronal cell comprises a neuron, a glial cell, an astrocyte, a satellite cell, or an enteric glial cell.

In certain embodiments of the systems and methods of the disclosure, the functionally heterogeneous cell population comprises one or more endocrine cells. In certain embodiments, the one or more endocrine cells are isolated or derived from a pineal gland, a pituitary gland, a pancreas, an ovary, a testicle, a thyroid gland, a parathyroid gland, a hypothalamus, or an adrenal gland.

In certain embodiments of the systems and methods of the disclosure, the subject cell is an endocrine cell. In certain embodiments, the endocrine cell is isolated or derived from a pineal gland, a pituitary gland, a pancreas, an ovary, a testicle, a thyroid gland, a parathyroid gland, a hypothalamus, or an adrenal gland.

In certain embodiments of the systems and methods of the disclosure, the functionally heterogeneous cell population comprises exocrine cells. In certain embodiments, the exocrine cell is isolated or derived from a salivary gland, a sweat gland or a component of the gastrointestinal tract. Components of the gastrointestinal tract may comprise a mouth, a stomach, a small intestine, and a large intestine.

In certain embodiments of the systems and methods of the disclosure, the subject cell is an exocrine cell. In certain embodiments, the exocrine cell is isolated or derived from a salivary gland, a sweat gland or a component of the gastrointestinal tract. Components of the gastrointestinal tract may comprise a mouth, a stomach, a small intestine, and a large intestine.

In certain embodiments of the systems and methods of the disclosure, the step of contacting the subject cell and the target cell or the stimulatory agent in a chamber comprises direct contact of the subject cell and the target cell or the stimulatory agent.

In certain embodiments of the systems and methods of the disclosure, the step of contacting the subject cell and the target cell or the stimulatory agent in a chamber comprises indirect contact of the subject cell and the target cell or the stimulatory agent. In certain embodiments, the indirect contact comprises fluid communication between the subject cell and the target cell or the stimulatory agent. In certain embodiments, the indirect contact comprises communication between the subject cell and the target cell or the stimulatory agent through a natural or artificial extracellular matrix. In certain embodiments, the indirect contact comprises communication between the subject cell and the target cell or the stimulatory agent through an intermediate cell.

In certain embodiments of the systems and methods of the disclosure, the target cell is a cancer cell. In certain embodiments, the cancer cell is a primary cancer cell or a cultured cancer cell. In certain embodiments, the primary cancer cell is metastatic.

In certain embodiments of the systems and methods of the disclosure, the target cell is a B-lymphocyte.

In certain embodiments of the systems and methods of the disclosure, the target cell is a bacteria, yeast, or microbe.

In certain embodiments of the systems and methods of the disclosure, the target cell is an infected cell. Exemplary infected cells may have contacted or may have been exposed to a virus, bacteria, yeast, or microbe.

In certain embodiments of the systems and methods of the disclosure, the target cell is a host cell. In certain embodiments, the host cell comprises any cell isolated or derived from the same individual as the subject cell. In certain embodiments, the host cell perpetuates an autoimmune response.

In certain embodiments of the systems and methods of the disclosure, the target cell is a host cell. In certain embodiments, the host cell comprises any cell isolated or derived from the same individual as the subject cell. In certain embodiments, the host cell is a target of an autoimmune response.

In certain embodiments of the systems and methods of the disclosure, the target cell is a host cell. In certain embodiments, the host cell comprises any cell isolated or derived from the same individual as the subject cell. In certain embodiments, the host cell is a functional cell and wherein the host cell does not stimulate an autoimmune response. The term "functional" cell is meant to describe a viable cell that does not contribute to a disease or disorder in the host. Alternatively, or in addition, the term "functional" cell may describe a cell without any known mutations that cause a disease or disorder in the host. For example, a functional cell may be noncancerous and/or non-autoimmune.

In certain embodiments of the systems and methods of the disclosure, the stimulatory agent comprises a stimulatory antibody. In certain embodiments, the stimulatory antibody is a monoclonal antibody. In certain embodiments, the monoclonal antibody is a fully human antibody. In certain embodiments, the monoclonal antibody is a humanized antibody, a chimeric antibody, a recombinant antibody or a modified antibody. In certain embodiments, the modified antibody comprises one or more sequence variations when compared to a fully human version of an antibody having the same epitope specificity, one or more modified or synthetic amino acids, or a chemical moiety to enhance a stimulatory function. In certain embodiments, the stimulatory antibody specifically binds an epitope of a T cell regulator protein. In certain embodiments, the T cell regulator protein comprises programmed cell death protein 1 (PD-1). In certain embodiments, the stimulatory antibody comprises Nivolumab or a biosimilar thereof.

In certain embodiments of the systems and methods of the disclosure, the stimulatory agent comprises a stimulatory ligand. In certain embodiments, the stimulatory ligand comprises programmed death ligand 1 (PD-L1).

In certain embodiments of the systems and methods of the disclosure, each antibody of the antibody panel is attached to a surface that is removably attached to the chamber.

In certain embodiments of the systems and methods of the disclosure, each antibody of the antibody panel is attached to the surface to form a repeating pattern and wherein each chamber of the plurality of chambers comprises a repeat of the pattern. Antibody panels of the disclosure form patterns in which each repeat comprises the full panel of antibodies. For examples, if the antibody panel comprises antibodies "a", "b" and "c", then each repeat of the pattern also comprises at least one of antibody "a", "b" and "c". The pattern need only have a size scale such that each chamber aligns with at least one repeat of the pattern. In preferred embodiments, the pattern need only have a size scale such that each chamber aligns with one repeat of the pattern. When additional detectable labels are added to the panel to identify, capture or quantify secreted small molecules and/or ions, the detectable labels also repeat by the same rules set out for the antibody pattern.

In certain embodiments of the systems and methods of the disclosure, the conditions sufficient to permit (1) the subject cell to secrete at least one of a peptide, polypeptide, and protein and (2) at least one antibody of the antibody panel specific for the at least one protein to bind the at least one peptide, polypeptide, or protein, forming at least one of an antibody:secreted peptide, antibody:secreted polypeptide, or an antibody:secreted protein complex, may comprise 5% $CO_2$ and 37° C. for a period of 2 hours, about 2 hours or at least 2 hours. Alternatively, the period may be 4 hours, about 4 hours or at least 4 hours; 8 hours, about 8 hours or at least 8 hours; 12 hours, about 12 hours or at least 12 hours; 16 hours, about 16 hours or at least 16 hours; or 24 hours, about 24 hours or at least 24 hours. In certain embodiments, the period is 16 hours, about or at least 16 hours.

In certain embodiments of the systems and methods of the disclosure, at least one chamber comprises a cell media that maintains the viability of the subject cell from steps (a) through (c) (e.g., from contacting the subject cell and target cell or the stimulatory agent through removal of the antibody panel comprising antibody complexes with one or more of a peptide, polypeptide or protein secreted from the subject cell).

In certain embodiments of the systems and methods of the disclosure, the secretome comprises one or more distinct peptide(s), polypeptide(s), or protein(s) that indicate diminished or decreasing cell function or cell viability.

In certain embodiments of the systems and methods of the disclosure, the secretome comprises one or more distinct peptide(s), polypeptide(s), or protein(s) that indicate(s) augmented or increasing inflammation.

In certain embodiments of the systems and methods of the disclosure, the secretome comprises one or more distinct peptide(s), polypeptide(s), or protein(s) that indicate(s) increased cell activity or cellular stimulation.

In certain embodiments of the systems and methods of the disclosure, the methods further comprise determining a Polyfunctional Strength Index (PSI). In certain embodiments, the Polyfunctional Strength Index is the product of a percentage of polyfunctional subject cells within the heterogeneous cell population and an average signal intensity of two or more cytokines. In certain embodiments, the average signal intensity of two or more cytokines is the average signal intensity of two or more distinct cytokines (i.e. AB versus AA). In certain embodiments, the polyfunctional subject cells, at a single cell level, secrete at least two cytokines. In certain embodiments, the polyfunctional subject cells, at a single cell level, secrete at least two distinct cytokines (i.e. AB versus AA). In certain embodiments, the at least two cytokines produced by each of the polyfunctional subject cells and the two or more cytokines of the average signal intensity comprise the same cytokines (e.g. AB and AB). In certain embodiments, the at least two cytokines produced by each of the polyfunctional subject cells and the two or more cytokines of the average signal intensity consist of the same cytokines. In certain embodiments, an increase in the PSI indicates an increase in the potency of the polyfunctional subject cells.

The disclosure provides a use of a secretome produced by a method of the disclosure for the identification of a T-Lymphocyte expressing a CAR that specifically binds an antigen presented on a target cell, a CAR that specifically binds a stimulatory agent, or a CAR that specifically binds an antigen presented on a target cell and specifically binds a stimulatory agent.

The disclosure provides a use of a secretome produced by a method of the disclosure for the evaluation of the safety of a cellular therapy, wherein the cellular therapy comprises the subject cell, the cellular therapy is intended to respond to the target cell or the stimulatory agent, and wherein the cellular therapy is considered safe when the secretome lacks one or more peptide(s), polypeptide(s), or protein(s) that stimulate the immune system.

The disclosure provides a use of a secretome produced by a method of the disclosure for the evaluation of the safety of a cellular therapy, wherein the cellular therapy comprises the subject cell, the cellular therapy is intended to respond to the target cell or the stimulatory agent, and wherein the cellular therapy is considered safe when the secretome lacks one or more peptide(s), polypeptide(s), or protein(s) that indicate decreased cell viability.

The disclosure provides a use of a secretome produced by a method of the disclosure for the evaluation of the efficacy of a cellular therapy, wherein the cellular therapy comprises the subject cell, the cellular therapy is intended to respond to the target cell or the stimulatory agent, and wherein the cellular therapy is considered safe when the secretome contains one or more peptide(s), polypeptide(s), or protein(s) that indicate a selective response to the target cell.

The disclosure provides a use of the secretome produced by a method of the disclosure for the evaluation of a cellular therapy, wherein the cellular therapy comprises the subject cell and wherein the subject cell is a chimeric antigen receptor (CAR)-expressing T cell; wherein the cellular therapy is intended to respond to the target cell or the stimulatory agent, wherein the target cell is a cancer cell that expresses an antigen to which the chimeric antigen receptor (CAR) specifically binds, and wherein, upon binding the antigen, the chimeric antigen receptor (CAR) stimulates the T cell; wherein the cellular therapy is considered efficacious when the secretome comprises one or more peptide(s), polypeptide(s), or protein(s) that stimulate the immune system above a first threshold, wherein the one or more peptide(s), polypeptide(s), or protein(s) comprise one or more cytokines, and wherein the one or more cytokines are selected from the group consisting of effector, stimulatory or chemoattractive cytokines; and wherein the cellular therapy is considered safe when the secretome comprises one or more peptide(s), polypeptide(s), or protein(s) that mediate a deleterious process, wherein the one or more peptide(s), polypeptide(s), or protein(s) comprise one or more cytokines, and wherein the one or more cytokines are selected from the group consisting of regulatory and inflammatory cytokines. In certain embodiments of this use, the effector cytokines are selected from the group consisting of Granzyme B, IFN-γ, M1P-1a, Performin, TNF-α, and TNF-β. In certain embodiments of this use, wherein the stimulatory cytokines are selected from the group consisting of GM-CSF, IL-12, IL-15, IL-2, IL-21, IL-5, IL-7, IL-8 and IL-9. In certain embodiments of this use, the chemoattractive cytokines are selected from the group consisting of CCL-11, IP-10, MIP-1β and RANTES. In certain embodiments of this use, the regulatory cytokines are selected from the group consisting of IL-10, IL-13, IL-22, IL-4, TGF-β, sCD137 and sCD4OL. In certain embodiments of this use, the inflammatory cytokines are selected from the group consisting of IL-17A, IL-17F, IL-1p, IL-6, MCP-1 and MCP-4. In certain embodiments of this use, the deleterious process comprises inflammation. In certain embodiments of this use, the deleterious process comprises an autoimmune response. In certain embodiments of this use, the deleterious process comprises a non-selective response to the target cell. In certain embodiments of this use, the subject cell is isolated or derived from an adoptive cell therapy for use in the treatment of a cancer.

The disclosure provides a use of the secretome produced by a method of the disclosure for the evaluation of a cellular therapy, wherein the cellular therapy comprises the subject cell and wherein the subject cell is a chimeric antigen receptor (CAR)-expressing T cell; wherein the cellular therapy is intended to respond to the target cell or the stimulatory agent, wherein the target cell is an autoimmune cell that expresses an antigen to which the chimeric antigen receptor (CAR) specifically binds, and wherein, upon binding the antigen, the chimeric antigen receptor (CAR) stimulates the T cell; wherein the cellular therapy is considered efficacious when the secretome comprises one or more peptide(s), polypeptide(s), or protein(s) that stimulate the immune system above a first threshold, wherein the one or more peptide(s), polypeptide(s), or protein(s) comprise one or more cytokines, and wherein the one or more cytokines are selected from the group consisting of effector, stimulatory or chemoattractive cytokines; and wherein the cellular therapy is considered safe when the secretome comprises one or more peptide(s), polypeptide(s), or protein(s) that mediate a deleterious process, wherein the one or more peptide(s), polypeptide(s), or protein(s) comprise one or more cytokines, and wherein the one or more cytokines are selected from the group consisting of regulatory and inflammatory cytokines. In certain embodiments of this use, the effector cytokines are selected from the group consisting of Granzyme B, IFN-γ, MIP-1α, Performin, TNF-α, and TNF-β. In certain embodiments of this use, wherein the stimulatory cytokines are selected from the group consisting of GM-CSF, IL-12, IL-15, IL-2, IL-21, IL-5, IL-7, IL-8 and IL-9. In certain embodiments of this use, the chemoattractive cytokines are selected from the group consisting of CCL-11, IP-10, MIP-1β and RANTES. In certain embodiments of this use, the regulatory cytokines are selected from the group consisting of IL-10, IL-13, IL-22, IL-4, TGF-β, sCD137 and sCD4OL. In certain embodiments of this use, the inflammatory cytokines are selected from the group consisting of IL-17A, IL-17F, IL-1β, IL-6, MCP-1 and MCP-4. In certain embodiments of this use, the deleterious process comprises inflammation. In certain embodiments of this use, the deleterious process comprises an autoimmune response. In certain embodiments of this use, the deleterious process comprises a non-selective response to the target cell. In certain embodiments of this use, the autoimmune cell is an immune cell that initiates, effectuates, or enhances an autoimmune response. In certain embodiments of this use, the subject cell is isolated or derived from an adoptive cell therapy for use in the treatment of an autoimmune condition.

The disclosure provides a use of the secretome produced by a method of the disclosure for the evaluation of a cellular therapy, wherein the cellular therapy comprises the subject cell and wherein the subject cell is a chimeric antigen receptor (CAR)-expressing T cell; wherein the cellular therapy is intended to respond to the target cell or the stimulatory agent, wherein the target cell is an infected cell that expresses an antigen to which the chimeric antigen receptor (CAR) specifically binds, and wherein, upon binding the antigen, the chimeric antigen receptor (CAR) stimulates the T cell; wherein the cellular therapy is considered efficacious when the secretome comprises one or more peptide(s), polypeptide(s), or protein(s) that stimulate the immune system above a first threshold, wherein the one or more peptide(s), polypeptide(s), or protein(s) comprise one or more cytokines, and wherein the one or more cytokines are selected from the group consisting of effector, stimulatory or chemoattractive cytokines; and wherein the cellular therapy is considered safe when the secretome comprises one or more peptide(s), polypeptide(s), or protein(s) that mediate a deleterious process, wherein the one or more peptide(s), polypeptide(s), or protein(s) comprise one or more cytokines, and wherein the one or more cytokines are selected from the group consisting of regulatory and inflammatory cytokines. In certain embodiments of this use, the effector cytokines are selected from the group consisting of Granzyme B, IFN-γ, M1P-1α, Performin, TNF-α, and TNF-β. In certain embodiments of this use, wherein the stimulatory cytokines are selected from the group consisting of GM-CSF, IL-12, IL-15, IL-2, IL-21, IL-5, IL-7, IL-8 and IL-9. In certain embodiments of this use, the chemoattractive cytokines are selected from the group consisting of CCL-11, IP-10, MIP-1β and RANTES. In certain embodiments of this use, the regulatory cytokines are selected from the group consisting of IL-10, IL-13, IL-22, IL-4, TGF-β, sCD137 and sCD4OL. In certain embodiments of this use, the inflammatory cytokines are selected from the group consisting of IL-17A, IL-17F, IL-1β, IL-6, MCP-1 and MCP-4. In certain embodiments of this use, the deleterious process comprises inflammation. In certain embodiments of this use, the deleterious process comprises an autoimmune response. In certain embodiments of this use, the deleterious process comprises a non-selective response to the target cell. In certain embodiments of this use, the autoimmune cell is an immune cell that initiates, effectuates, or enhances an autoimmune response. In certain embodiments of this use, the subject cell is isolated or derived from an adoptive cell therapy for use in the treatment of an infection or an infectious/contagious condition.

The disclosure provides a use of the secretome produced by a method of the disclosure for the evaluation of a cellular therapy, wherein the cellular therapy comprises the subject cell and wherein the subject cell is a chimeric antigen receptor (CAR)-expressing T cell; wherein the cellular therapy is intended to respond to the target cell or the stimulatory agent, wherein the target cell is a cardiovascular cell that expresses an antigen to which the chimeric antigen receptor (CAR) specifically binds, and wherein, upon binding the antigen, the chimeric antigen receptor (CAR) stimulates the T cell; wherein the cellular therapy is considered efficacious when the secretome comprises one or more peptide(s), polypeptide(s), or protein(s) that stimulate the immune system above a first threshold, wherein the one or more peptide(s), polypeptide(s), or protein(s) comprise one or more cytokines, and wherein the one or more cytokines are selected from the group consisting of effector, stimulatory or chemoattractive cytokines; and wherein the cellular therapy is considered safe when the secretome comprises one or more peptide(s), polypeptide(s), or protein(s) that mediate a deleterious process, wherein the one or more peptide(s), polypeptide(s), or protein(s) comprise one or more cytokines, and wherein the one or more cytokines are selected from the group consisting of regulatory and inflammatory cytokines. In certain embodiments of this use, the effector cytokines are selected from the group consisting of Granzyme B, IFN-γ, M1P-1α, Performin, TNF-α, and TNF-β. In certain embodiments of this use, wherein the stimulatory cytokines are selected from the group consisting of GM-CSF, IL-12, IL-15, IL-2, IL-21, IL-5, IL-7, IL-8 and IL-9. In certain embodiments of this use, the chemoattractive cytokines are selected from the group consisting of CCL-11, IP-10, MIP-1β and RANTES. In certain embodiments of this use, the regulatory cytokines are selected from the group consisting of IL-10, IL-13, IL-22, IL-4, TGF-β, sCD137 and sCD4OL. In certain embodiments of this use, the inflammatory cytokines are selected from the group consisting of IL-17A, IL-17F, IL-1β, IL-6, MCP-1 and MCP-4. In certain embodiments of this use, the deleterious process comprises inflammation. In certain embodiments of this use, the deleterious process comprises an autoimmune response. In certain embodiments of this use, the deleterious process comprises a non-selective response to the target cell. In certain embodiments of this use, the autoimmune cell is an immune cell that initiates, effectuates, or enhances an autoimmune response. In certain embodiments of this use, the cardiovascular cell is a smooth muscle cell, a cardiac muscle cell, an endothelial cell, or any other cell type integrated into a capillary, vein, or an artery. In certain embodiments of this use, the cardiovascular cell is a component of the local or circulating blood, including a blood platelet. In certain embodiments of this use, the platelet is a component of a blood clot or another form of obstruction to healthy blood flow. In certain embodiments of this use, the cardiovascular cell is a damaged cell. In certain embodiments of this use, the cardiovascular cell is an infected cell. In certain embodiments of this use, the subject cell is isolated or derived from an adoptive cell therapy for use in the treatment of a cardiovascular condition or a vascular condition.

The disclosure provides a method of identifying a subject cell population as efficacious for use in an adoptive cell therapy, comprising: detecting at least one component of a secretome of each subject cell of the subject cell population according to the method of identifying a secretome from a subject cell of the disclosure; identifying a subpopulation of polyfunctional cells of the subject cell population, wherein a polyfunctional cell of subject cells of the subject cell population secrete two or more signaling molecules; calculating a percentage of polyfunctionality of the subject cell population, wherein the percentage of polyfunctionality is the percentage of polyfunctional cells within the subject cell population; measuring a signal intensity of a first signaling molecule of the secretome of each polyfunctional cell of the subject cell population; measuring a signal intensity of a second signaling molecule of the secretome of each polyfunctional cell of the subject cell population; calculating a Polyfunctional Strength Index (PSI) for each polyfunctional cell of the subject cell population, wherein the PSI comprises (a) the product of the percentage of polyfunctionality of the subject cell population and the signal intensity of the first signaling molecule and (b) the product of the percentage of polyfunctionality of the subject cell population and the signal intensity of the second signaling molecule; identifying the subject cell population as efficacious for use in an adoptive cell therapy when the PSI indicates that at least 50% of the subject cells in the subject cell population are polyfunctional, the signal intensity of the first signaling molecule indicates that the concentration of the first signaling molecule within the chamber is between 2 pg/ml and 10,000 pg/ml, inclusive of the endpoints, and the signal intensity of the second signaling molecule indicates that the concentration of the second signaling molecule within the chamber is between 2 pg/ml and 10,000 pg/ml, inclusive of the endpoints; and identifying the subject cell population as not efficacious for use in an adoptive cell therapy when the PSI indicates that less than 50% of the subject cells in the subject cell population are polyfunctional, the signal intensity of the first signaling molecule indicates that the concentration of the first signaling molecule within the chamber is less than 2 pg/ml, and the signal intensity of the second signaling molecule indicates that the concentration of the second signaling molecule within the chamber is less than 2 pg/ml.

In certain embodiments of the methods of identifying a subject cell population as efficacious for use in an adoptive cell therapy, the subject cell population comprises a plurality of immune cells. In certain embodiments, the plurality of immune cells comprises a T-lymphocyte, a B-lymphocyte, a natural killer (NK) cell, a macrophage, a neutrophil, a mast cell, an eosinophil, a basophil or a combination thereof. In certain embodiments, the T-lymphocyte is a naive T-lymphocyte, an activated T-lymphocyte, an effector T-lymphocyte, a helper T-lymphocyte, a cytotoxic T-lymphocyte, a gamma-delta T-lymphocyte, a regulatory T-lymphocyte, a memory T-lymphocyte, or a memory stem T-lymphocyte. In certain embodiments, the T-lymphocyte expresses a non-naturally occurring antigen receptor. In certain embodiments, the T-lymphocyte expresses a Chimeric Antigen Receptor (CAR).

In certain embodiments of the methods of identifying a subject cell population as efficacious for use in an adoptive cell therapy, the subject cell population comprises a plurality of neuronal cells. In certain embodiments, the plurality of neuronal cells comprises a neuron, a glial cell, an astrocyte, a satellite cell, an enteric glial cell or a combination thereof.

In certain embodiments of the methods of identifying a subject cell population as efficacious for use in an adoptive cell therapy, the subject cell population comprises a plurality of endocrine cells. In certain embodiments, the plurality of endocrine cells comprises one or more cells isolated or derived from a pineal gland, a pituitary gland, a pancreas, an ovary, a testicle, a thyroid gland, a parathyroid gland, a hypothalamus, or an adrenal gland.

In certain embodiments of the methods of identifying a subject cell population as efficacious for use in an adoptive cell therapy, the subject cell population comprises a plurality of exocrine cells. In certain embodiments, the plurality of exocrine cells comprises one or more cells isolated or derived from a salivary gland, a sweat gland or a component of the gastrointestinal tract. In certain embodiments, the component of the gastrointestinal tract comprises a mouth, a stomach, a small intestine, and a large intestine.

In certain embodiments of the methods of identifying a subject cell population as efficacious for use in an adoptive cell therapy, the target cell is a cancer cell. In certain embodiments, the cancer cell is a primary cancer cell or a cultured cancer cell. In certain embodiments, the primary cancer cell is metastatic.

In certain embodiments of the methods of identifying a subject cell population as efficacious for use in an adoptive cell therapy, the target cell is a B-lymphocyte.

In certain embodiments of the methods of identifying a subject cell population as efficacious for use in an adoptive cell therapy, the target cell is a bacteria, yeast, or microbe.

In certain embodiments of the methods of identifying a subject cell population as efficacious for use in an adoptive cell therapy, the target cell is an infected cell. Exemplary infected cells may have contacted or may have been exposed to a virus, bacteria, yeast, or microbe.

In certain embodiments of the methods of identifying a subject cell population as efficacious for use in an adoptive cell therapy, the target cell is a host cell. In certain embodiments, the host cell comprises any cell isolated or derived from the same individual as the subject cell. In certain embodiments, the host cell perpetuates an autoimmune response.

In certain embodiments of the methods of identifying a subject cell population as efficacious for use in an adoptive cell therapy, the target cell is a host cell. In certain embodiments, the host cell comprises any cell isolated or derived from the same individual as the subject cell. In certain embodiments, the host cell is a target of an autoimmune response.

In certain embodiments of the methods of identifying a subject cell population as efficacious for use in an adoptive cell therapy, the target cell is a host cell. In certain embodiments, the host cell comprises any cell isolated or derived from the same individual as the subject cell. In certain embodiments, the host cell is a functional cell and wherein the host cell does not stimulate an autoimmune response. The term "functional" cell is meant to describe a viable cell that does not contribute to a disease or disorder in the host. Alternatively, or in addition, the term "functional" cell may describe a cell without any known mutations that cause a disease or disorder in the host. For example, a functional cell may be non-cancerous and/or non-autoimmune.

In certain embodiments of the methods of identifying a subject cell population as efficacious for use in an adoptive cell therapy, the first signaling molecule is a peptide, a polypeptide, or a protein. In certain embodiments, the first signaling molecule is a cytokine.

In certain embodiments of the methods of identifying a subject cell population as efficacious for use in an adoptive cell therapy, the second signaling molecule is a peptide, a polypeptide, or a protein. In certain embodiments, the second signaling molecule is a cytokine.

In certain embodiments of the methods of identifying a subject cell population as efficacious for use in an adoptive cell therapy, the subject cell population comprises a plurality of T-lymphocytes; wherein the target cell is a cancer cell, an infected cell or a host cell that perpetuates an autoimmune response; the first signaling molecule comprises an effector cytokine, a stimulatory cytokine, or a chemoattractive cytokine and the second signaling molecule comprises an effector cytokine, a stimulatory cytokine, or a chemoattractive cytokine. In certain embodiments, at least one T-lymphocyte of the plurality of T-lymphocytes expresses a chimeric antigen receptor (CAR). In certain embodiments, each T-lymphocyte of the plurality of T-lymphocytes expresses a chimeric antigen receptor (CAR). In certain embodiments, the effector cytokine is Granzyme B, IFN-$\gamma$, M1P-1$\alpha$, Perforin, TNF-$\alpha$ or TNF-$\beta$. In certain embodiments, the stimulatory cytokine is GM-CSF, IL-12, IL-15, IL-2, IL-21, IL-5, IL-7, IL-8 and IL-9. In certain embodiments, the chemoattractive cytokine is CCL-11, IP-10, MIP-10 or RANTES.

In certain embodiments of the methods of identifying a subject cell population as efficacious for use in an adoptive cell therapy, the method further comprises identifying the subject cell population as safe for use in an adoptive cell therapy, when the PSI indicates that at least 50% of the subject cells in the subject cell population are polyfunctional, the signal intensity of the first signaling molecule indicates that the concentration of the first signaling molecule within the chamber is less than 2 pg/ml, the signal intensity of the second signaling molecule indicates that the concentration of the second signaling molecule within the chamber is less than 2 pg/ml, the subject cell population comprises a plurality of T-lymphocytes, the first signaling molecule comprises a regulatory cytokine or an inflammatory cytokine and the second signaling molecule comprises a regulatory cytokine or an inflammatory cytokine; and identifying the subject cell population as not safe for use in an adoptive cell therapy when the PSI indicates that at least 50% of the subject cells in the subject cell population are polyfunctional, the signal intensity of the first signaling molecule indicates that the concentration of the first signaling molecule within the chamber is greater than 2 pg/ml, the signal intensity of the second signaling molecule indicates that the concentration of the second signaling molecule within the chamber is greater than 2 pg/ml, the subject cell population comprises a plurality of T-lymphocytes, the first signaling molecule comprises a regulatory cytokine or an inflammatory cytokine and the second signaling molecule comprises a regulatory cytokine or an inflammatory cytokine. In certain embodiments, the regulatory cytokine is IL-10, IL-13, IL-22, IL-4, TGF-$\beta$, sCD137 and sCD40L. In certain embodiments, the inflammatory cytokine is IL-17A, IL-17F, IL-1$\beta$, IL-6, MCP-1 and MCP-4. In certain embodiments, at least one T-lymphocyte of the plurality of T-lymphocytes expresses a chimeric antigen receptor (CAR). In certain embodiments, each T-lymphocyte of the plurality of T-lymphocytes expresses a chimeric antigen receptor (CAR).

In certain embodiments of the methods of identifying a subject cell population as efficacious for use in an adoptive cell therapy, the subject cell population comprises at least 100 cells. In certain embodiments, the subject cell population comprises at least 500 cells. In certain embodiments, the subject cell population comprises at least 1000 cells. In certain embodiments, the subject cell population comprises at least 5000 cells.

In certain embodiments of the methods of identifying a subject cell population as efficacious for use in an adoptive cell therapy, the detecting step comprises detecting at least 2 components of a secretome from each subject cell of the subject cell population. In certain embodiments, the detecting step comprises detecting at least 10 components of a secretome from each subject cell of the subject cell population. In certain embodiments, the detecting step comprises detecting at least 20 components of a secretome from each subject cell of the subject cell population. In certain embodiments, the detecting step comprises detecting at least 30 components of a secretome from each subject cell of the subject cell population. In certain embodiments, the detecting step comprises detecting at least 50 components of a secretome from each subject cell of the subject cell population. In certain embodiments, the detecting step comprises detecting at least 100 components of a secretome from each subject cell of the subject cell population.

In certain embodiments of the methods of identifying a subject cell population as efficacious for use in an adoptive cell therapy, the percentage of polyfunctional cells comprises a first percentage of polyfunctional cells that secrete two or more signaling molecules, a second percentage of polyfunctional cells that secrete three or more signaling molecules, a third percentage of polyfunctional cells that secrete four or more signaling molecules, a fourth percentage of polyfunctional cells that secrete five or more signaling molecules, and a subsequent percentage of polyfunctional cells that secrete increasing numbers of signaling molecules.

In certain embodiments of the methods of identifying a subject cell population as efficacious for use in an adoptive cell therapy, the measuring of the signal intensity comprises detecting a fluorescent signal from a complex of an antibody specific for the first or second signaling molecule and the first or second signaling molecule, respectively, and normalizing each fluorescent signal against a reference signal to determine a relative fluorescent unit (RFU) value. In certain embodiments, the reference signal is a maximal signal, a minimal signal, or a signal from a component of the secretome with a constant or known concentration. In certain embodiments, the reference signal is a component of the secretome of a subject cell that is most abundant.

In certain embodiments of the methods of identifying a subject cell population as efficacious for use in an adoptive cell therapy, the method further comprises measuring a third or subsequent signaling molecule of the secretome of each polyfunctional cell.

In certain embodiments of the methods of identifying a subject cell population as efficacious for use in an adoptive cell therapy, the method further comprises determining a relative contribution of the first signaling molecule, the second signaling molecule or the subsequent signaling molecule to a response of the subpopulation of polyfunctional cells to a target cell or to a stimulatory agent, wherein the relative contribution is the product of an average of a percentage of the PSI of each polyfunctional cell from the first signaling molecule, the second signaling molecule or the subsequent signaling molecule from each polyfunctional cell and a total PSI for the subpopulation of polyfunctional cells.

(IL-13), Interleukin-22 (IL-22), Interleukin-4 (IL-4), TGF-β, sCD137 and sCD4OL. Inflammatory cytokines include, but are not limited to, Interleukin-17A (IL-17A), Interleukin-17F (IL-17F), Interleukin-1b (IL-1b), Interleukin-6 (IL-6), MCP-1, and MCP-4. Polyfunctionality of single CAR T-cells after stimulation by control or CD19 beads. Polyfunctionality is correlated with potency or success of immune mediated therapies.

FIG. 8A-G is a series of graphs and a key identifying the components of the secretomes of CAR-expressing T-Cells following stimulation by target cells. A. Cytokine secretion levels by CAR-expressing T-cells after stimulation with K562-CD19 target cells, where CD19 is a proxy for the leukemia cells or B-cell malignancies that are the cell therapy target. B. Dampened cytokine secretion by CAR-expressing T-cells after stimulation with K562-NGFR control cells (negative control cells because they do not include the CD19 target). C. Cytokine secretion levels in chambers (taking the form of micro-troughs for this example) containing a single CAR-expressing T-cell and a single K562-CD19 target cell. D. Dampened cytokine secretion in chambers containing a single CAR-expressing T-cell and a single K562-NGFR control cell. E. Key for the bar graphs in A-D. Each bar color represents the inclusion of a cytokine in a specific functional group. Effector cytokines include, but are not limited to, Granzyme B, Interferon-gamma (IFN-γ), MIP-1α, Perforin, TNF-α and TNF-β. C. Stimulatory cytokines include, but are not limited to, GM-CSF, Interleukin-12 (IL-12), Interleukin-15 (IL-15), Interleukin-2 (IL-2), Interleukin-21 (IL-21), Interleukin-5 (IL-5), Interleukin-7 (IL-7), Interleukin-8 (IL-8), and Interleukin-9 (IL-9). Chemoattractive cytokines include, but are not limited to, CCL-11, IP-10, MIP-10, and RANTES. Regulatory cytokines include, but are not limited to, Interleukin-10 (IL-10), Interleukin-13 (IL-13), Interleukin-22 (IL-22), Interleukin-4 (IL-4), TGF-01, sCD137 and sCD4OL. Inflammatory cytokines include, but are not limited to, Interleukin-17A (IL-17A), Interleukin-17F (IL-17F), Interleukin-1b (IL-1b), Interleukin-6 (IL-6), MCP-1, and MCP-4. F. Polyfunctionality of single CAR-expressing T cells in response to K562-CD19 or control stimulation. G. An increase in polyfunctionality when the K562-CD19 target cell is present in the chamber (taking the form of a micro-trough for this example) with the CAR-expressing T-cell.

Figure 1:
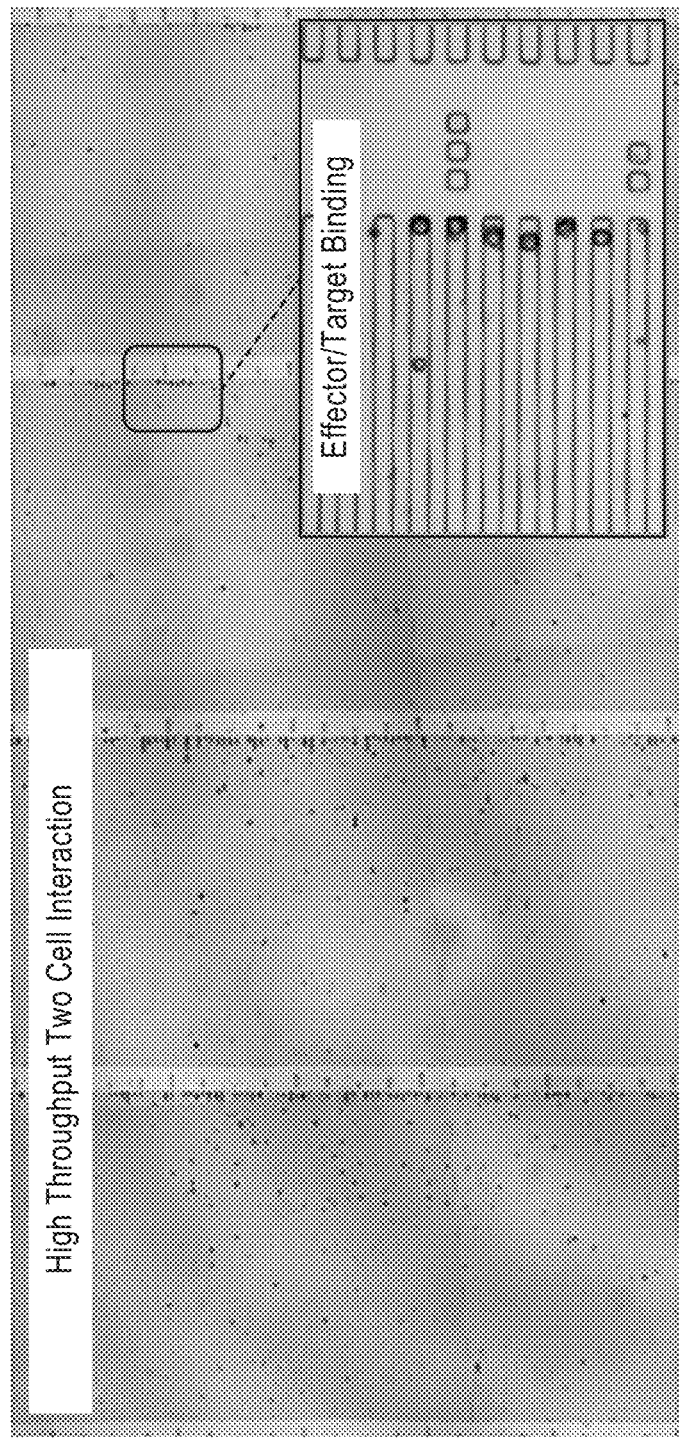
FIG. 1 is a photograph showing a system of the disclosure for high throughput analysis of Two-Cell Interactions. Natural Killer (NK) cell and leukemia cell (K562) populations loaded into a plurality of chambers (e.g. in this example, taking the form of micro-troughs) are mixed allowing for a high throughput analysis of individual two-cell interactions within one chamber (e.g. in this example, a micro-trough).
Figure 2:
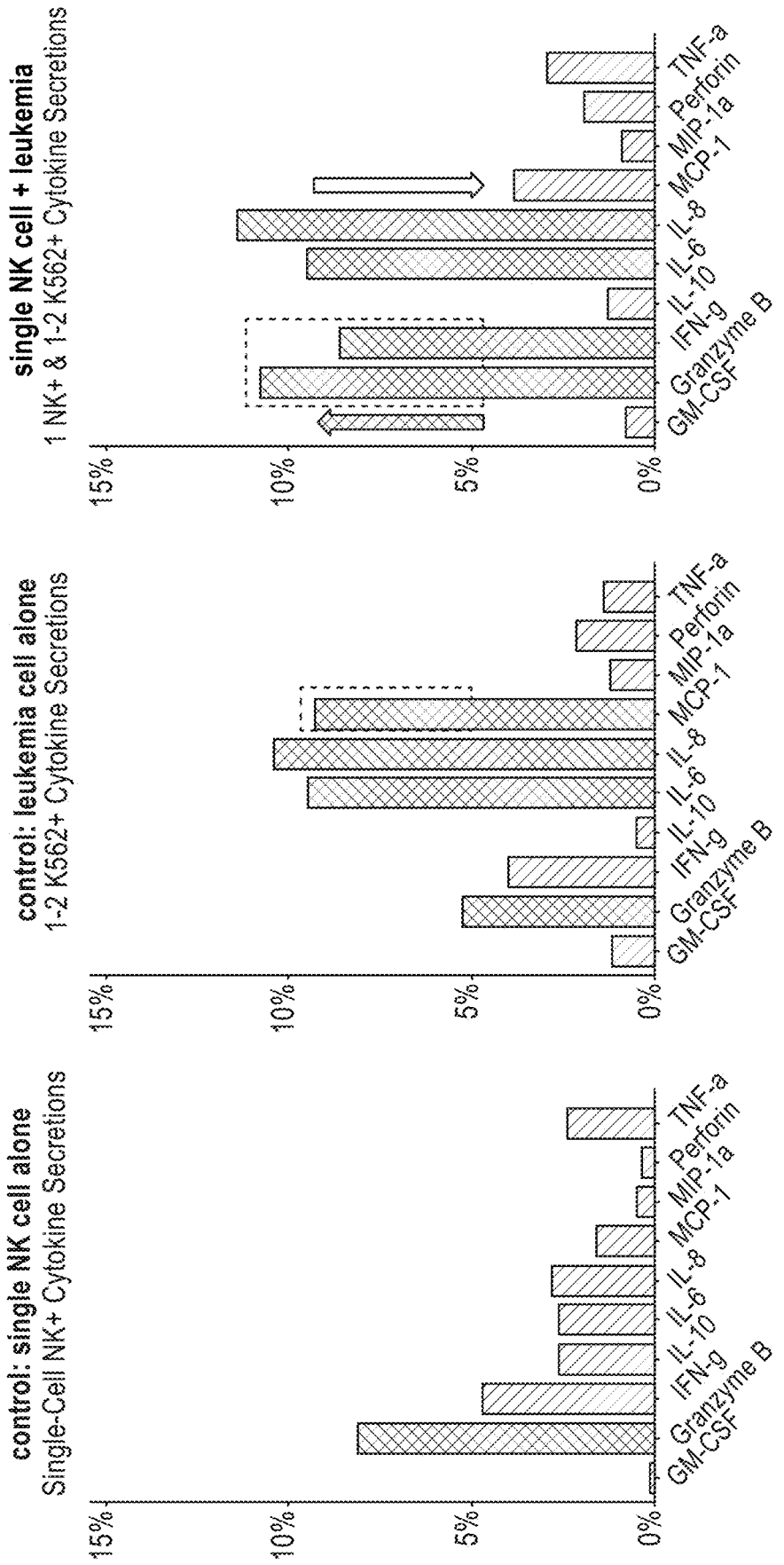
FIG. 2 is a series of graphs showing single cell secretion levels following two cell interactions with a Natural Killer (NK) cell as the subject cell and a leukemia cell (K562) as the target cell in a system of the disclosure. The percent (%) of cell subpopulation secreting is provided as a function of the type of cytokine secreted by the NK cell in each pairing. The secretomes of each NK cell were identified according to a method of the disclosure. The arrows indicate statistically significant differences between the levels of cytokine(s) identified in the secretome of single NK cells in each condition of the two-cell interaction method.
Figure 3:
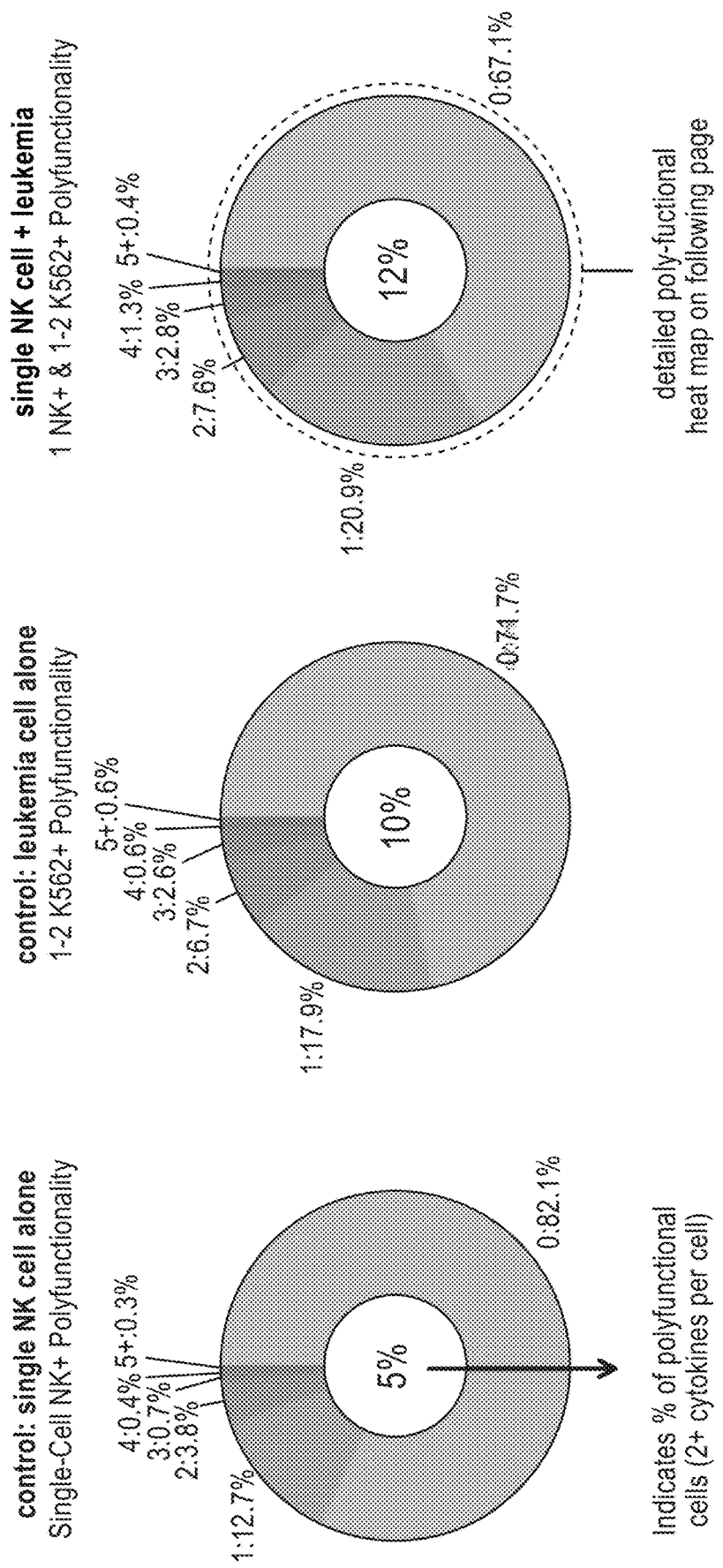
FIG. 3 is a series of graphs comparing cellular polyfunctionality following two cell interactions with a Natural Killer (NK) cell as the subject cell and a leukemia cell (K562) as the target cell in a system of the disclosure. The data demonstrate an increased percentage of poly-functional NK cells (secreting 2+ cytokines) following an interaction with the leukemia cell (right-hand graph).
Figure 4:
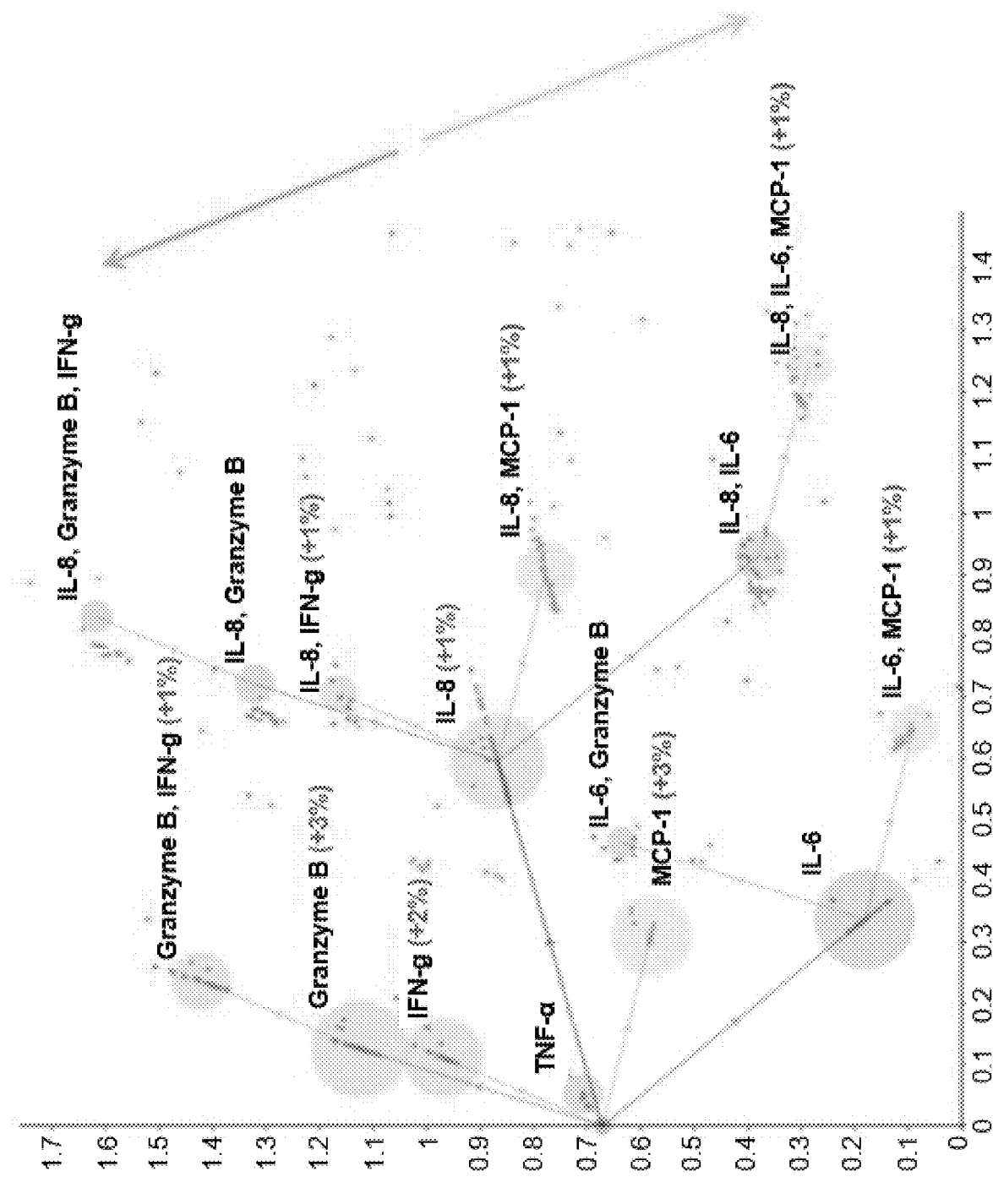
FIG. 4 is a Process Analytical Tools (PAT)-Principal Component Analysis (PCA) plot showing cellular polyfunctionality following two cell interactions with a Natural Killer (NK) cell as the subject cell and a leukemia cell (K562) as the target cell in a system of the disclosure. Functional groups are color-coded by population in which there is a dominant function. Leukemia-activated NK cells lead to increased effector functional cell subpopulations and reduced inflammatory cell subpopulations.
Figure 5:
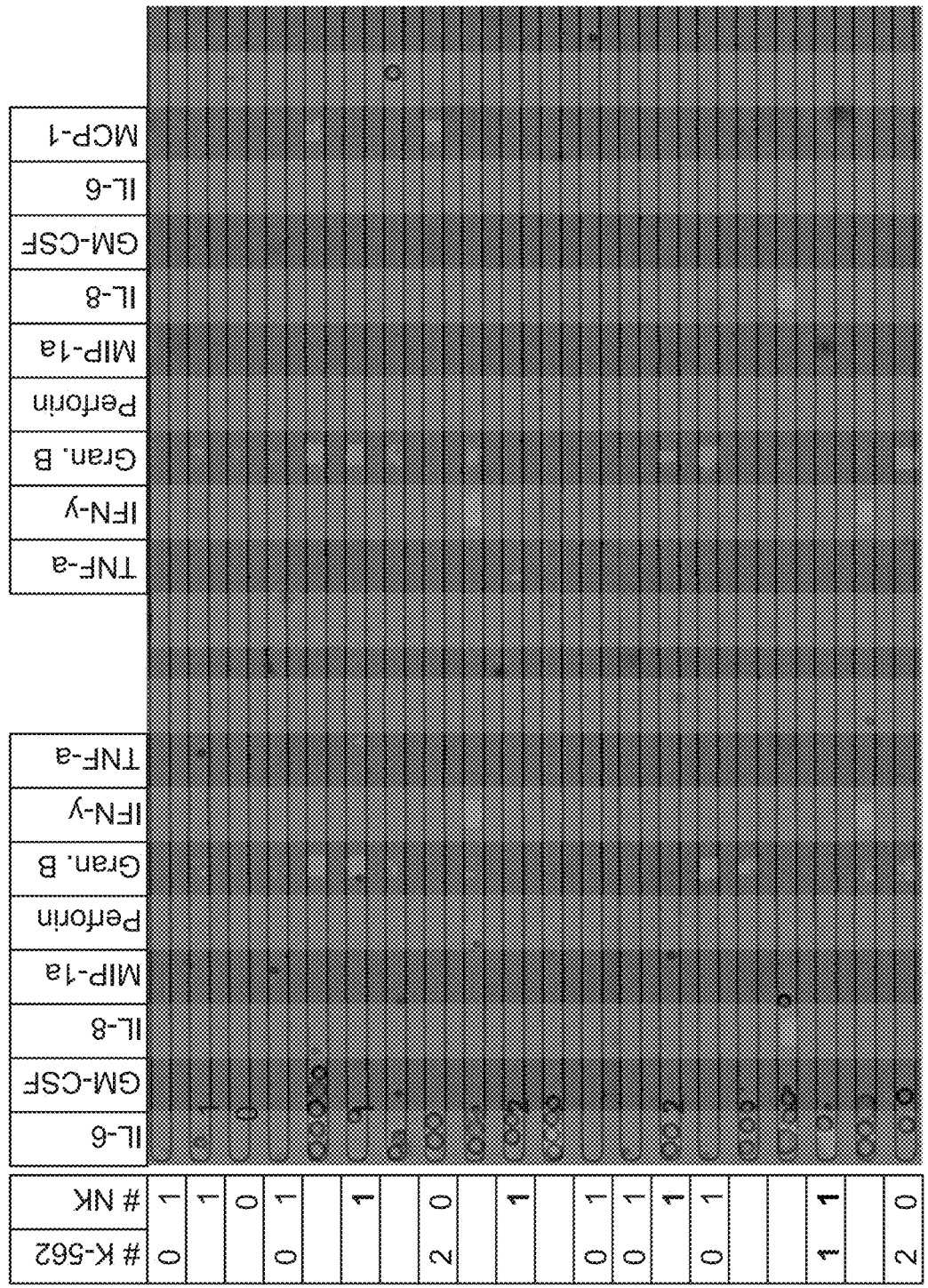
FIG. 5 is a photograph depicting the isolation and manipulation of human immune cell subsets in a system of the disclosure. NK/K562 interactions isolated at the single cell level are combined with their corresponding secretome (also referred to as a secretion profile), enabling a comprehensive analysis of a Target/Effector relationship.
Figure 6:
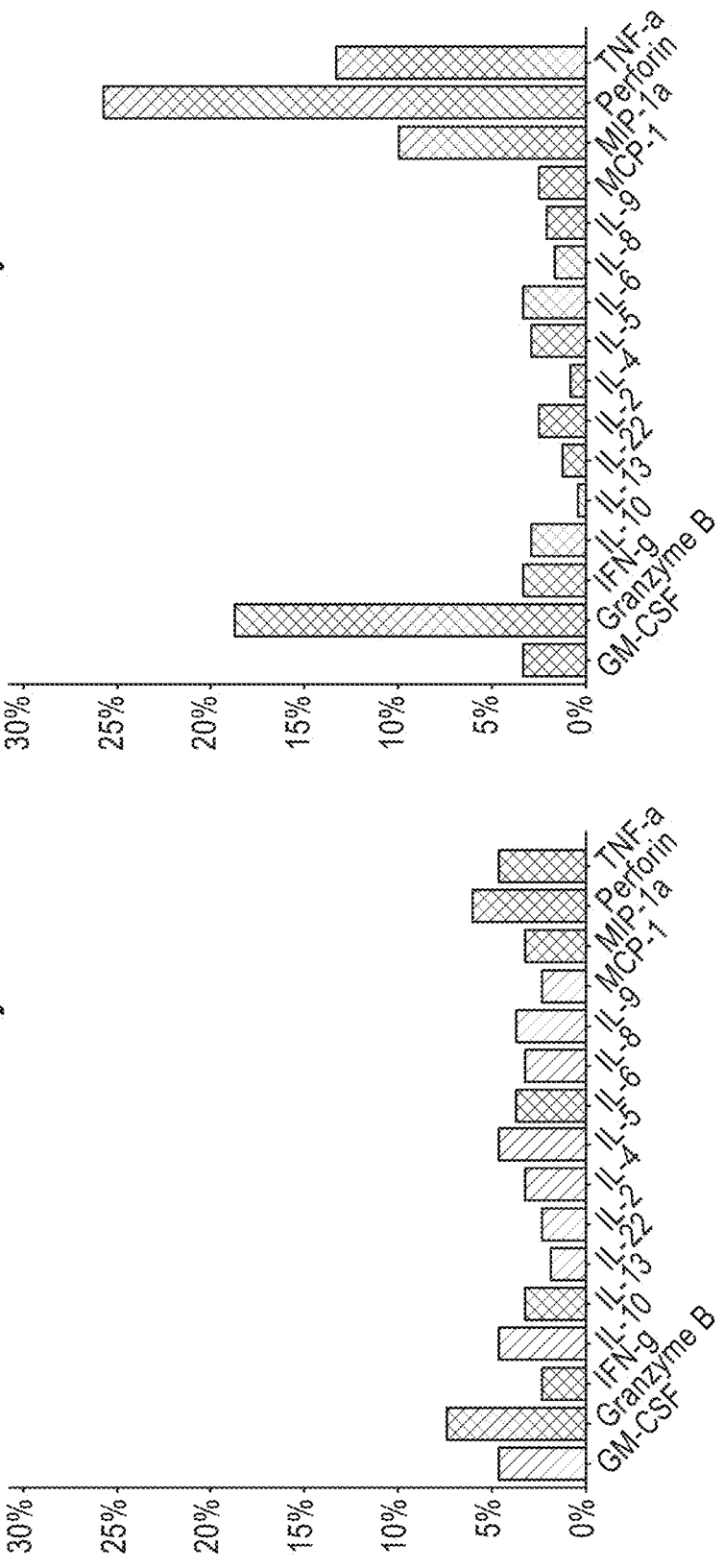
FIG. 6 is a pair of graphs depicting a cytokine and cytotoxicity profile of CD8-positive T cells. The addition of the bispecific antibody substantially increases both cytokine effector function and cytotoxicity to the target Raji cells (right-hand graph). The table above the graphs summarizes the data presented in the graphs below.
Figure 7A:
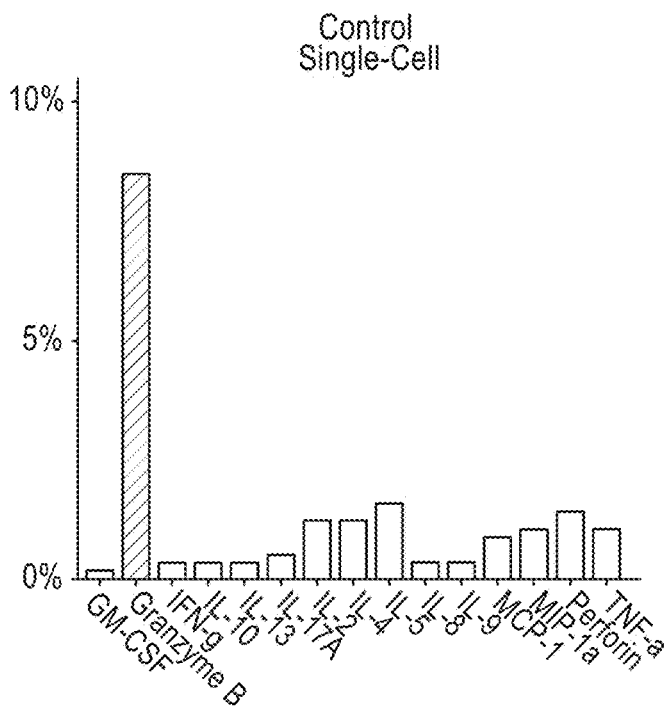
FIG. 7A-C is a series of graphs and a key identifying the components of the secretomes of CAR-expressing T-Cells following stimulation by CD19 Beads. A. Shows the upregulation in cytokine secretion by CAR T-cells stimulated with CD19 versus control beads. In the up-regulation case, certain cytokines associated with potency (TNFα, Granzyme, etc.) as well as certain cytokines associated with toxicity (IL-17A) are detailed. B. Key for the bar graphs in A. Each bar color represents the inclusion of a cytokine in a specific functional group. Effector cytokines include, but are not limited to, Granzyme B, Interferon-gamma (IFN-γ), MIP-1α, Perforin, TNF-α, and TNF-β. C. Stimulatory cytokines include, but are not limited to, GM-CSF, Interleukin-12 (IL-12), Interleukin-15 (IL-15), Interleukin-2 (IL-2), Interleukin-21 (IL-21), Interleukin-5 (IL-5), Interleukin-7 (IL-7), Interleukin-8 (IL-8), and Interleukin-9 (IL-9). Chemoattractive cytokines include, but are not limited to, CCL-11, IP-10, MIP-10, and RANTES. Regulatory cytokines include, but are not limited to, Interleukin-10 (IL-10), Interleukin-13
Figure 7A:
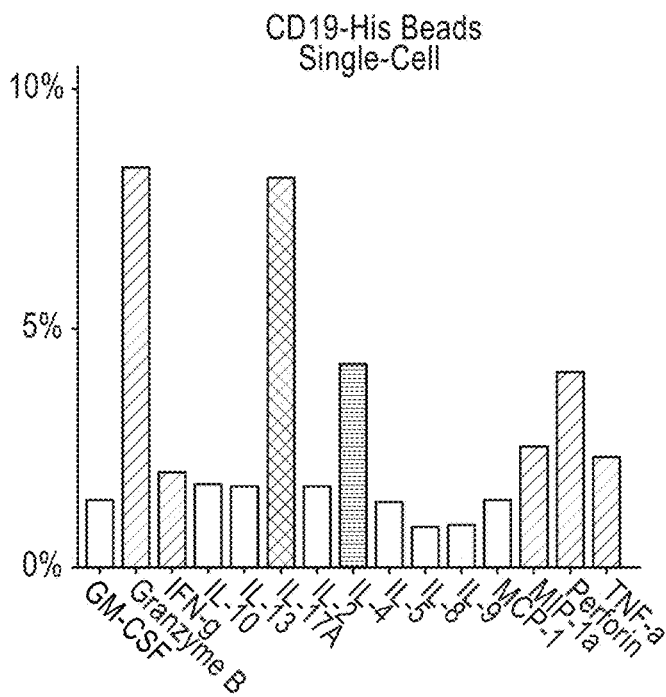
Figure 7B:
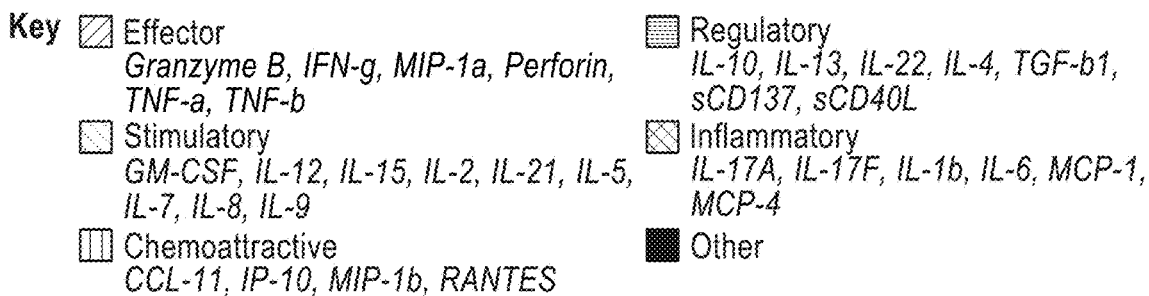
Figure 7C:
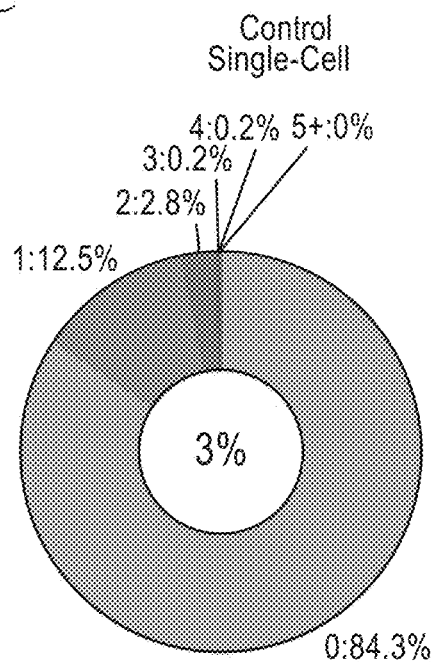
Figure 7C:
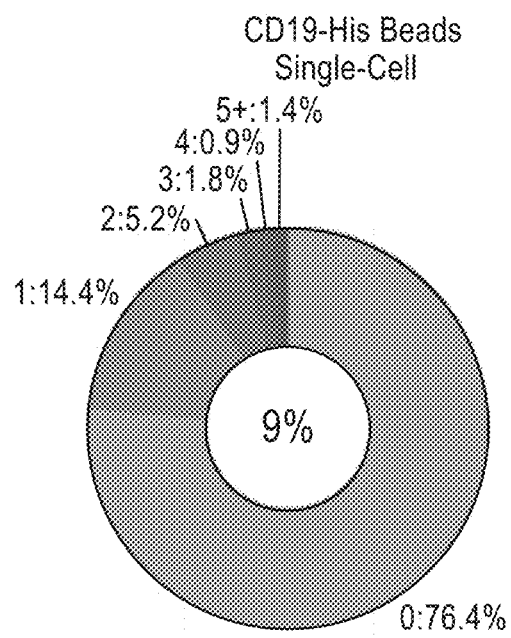
Figure 8A:
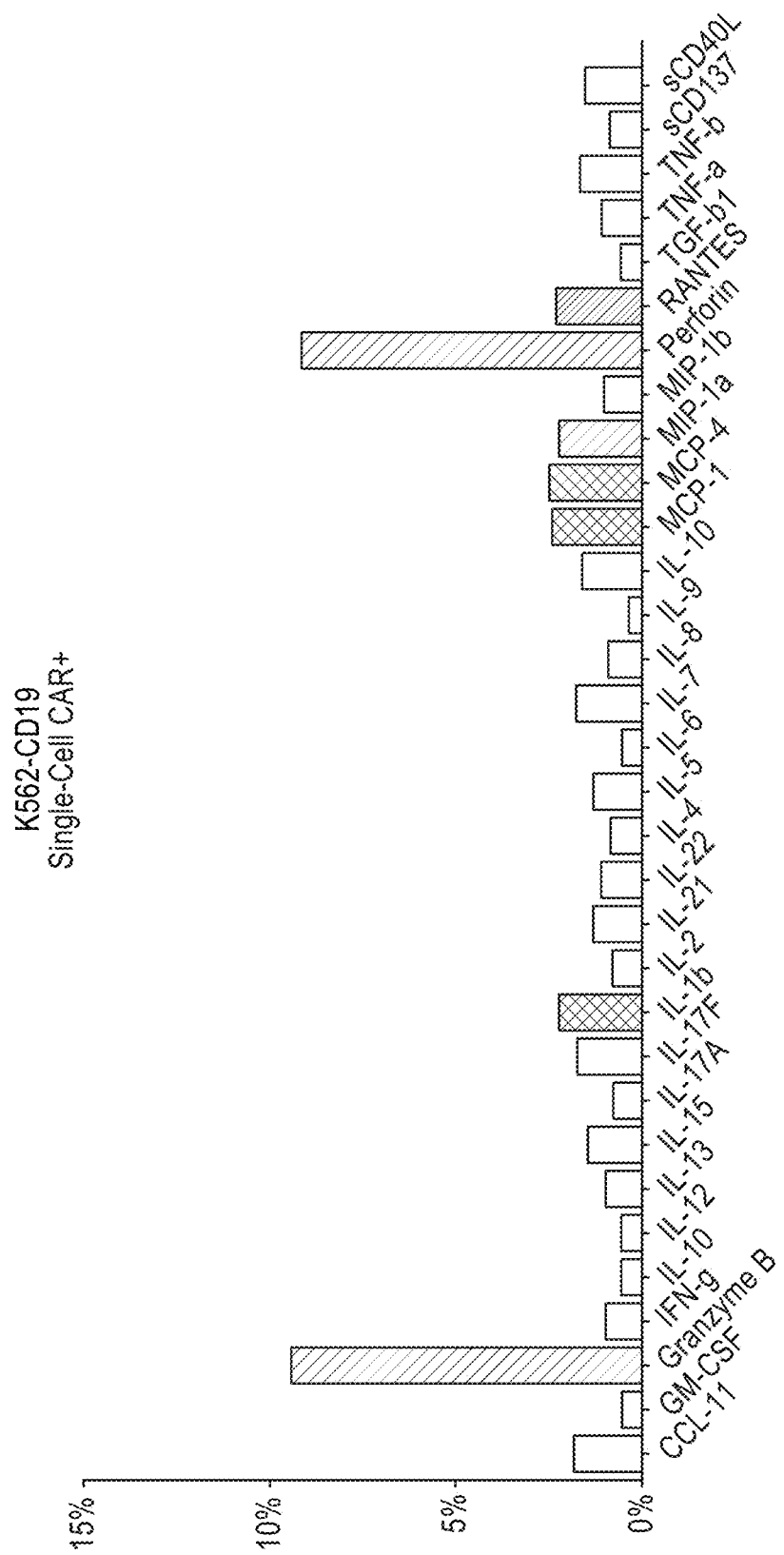
Figure 8C:
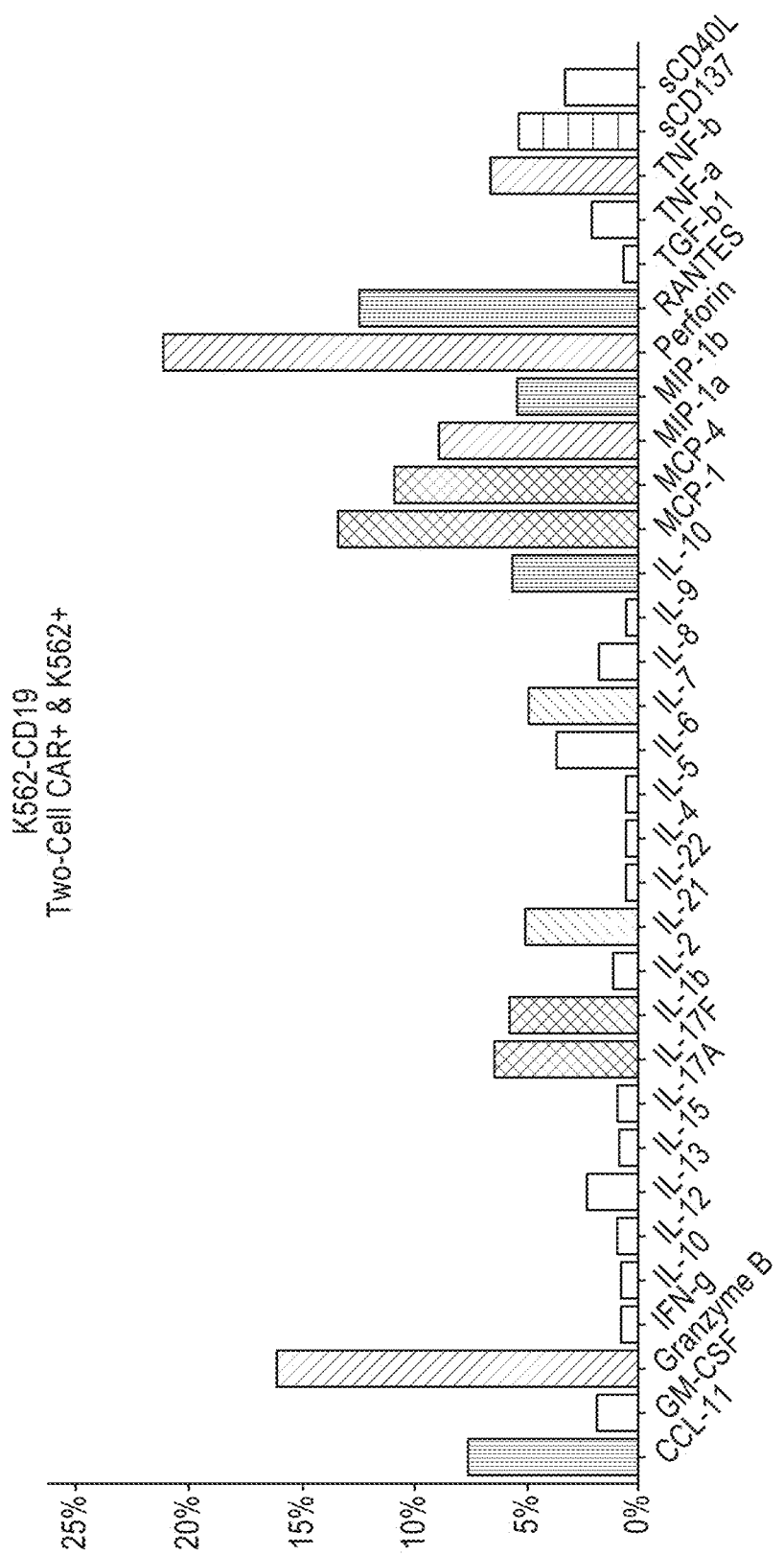
Figures 8D, 8E:
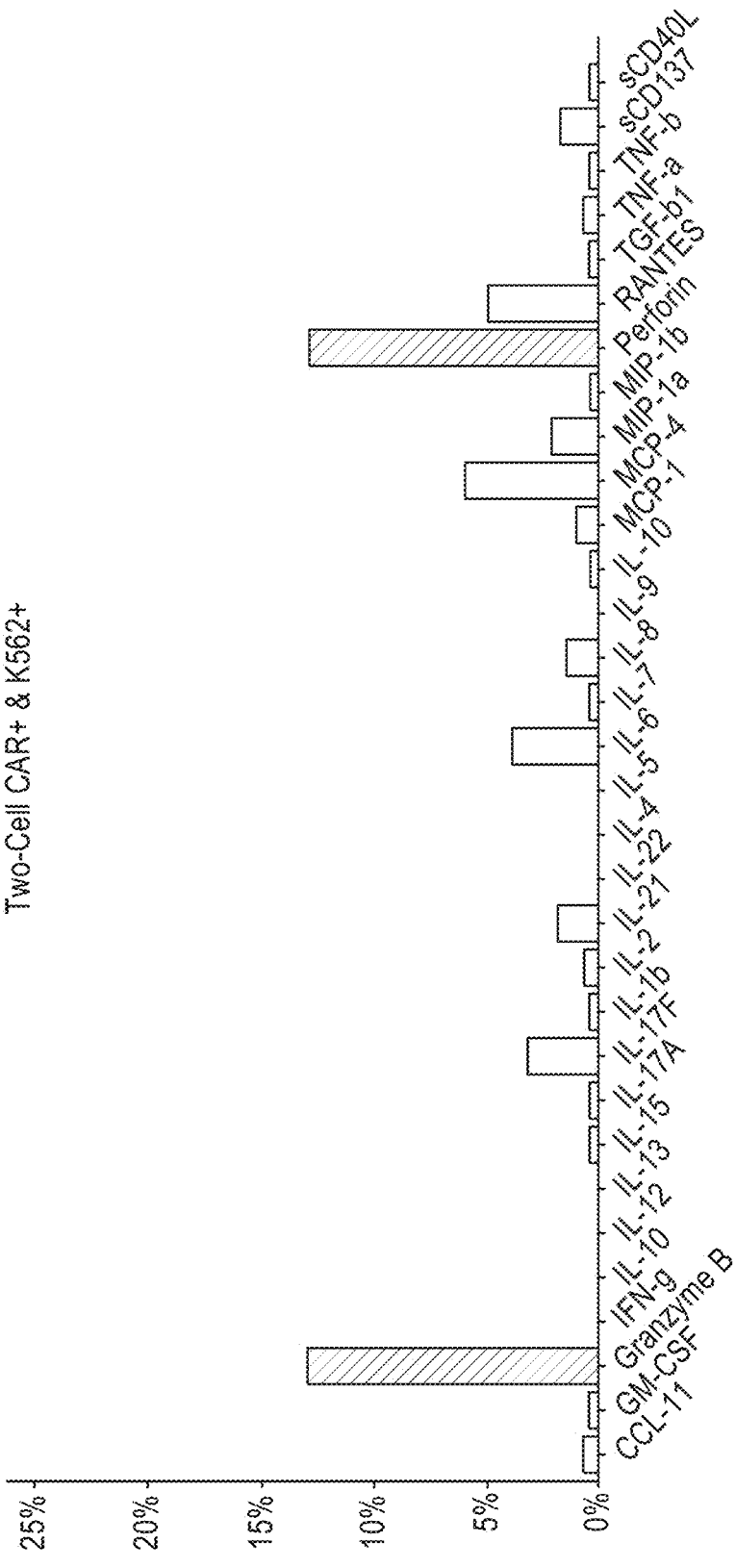
Figure 8F:
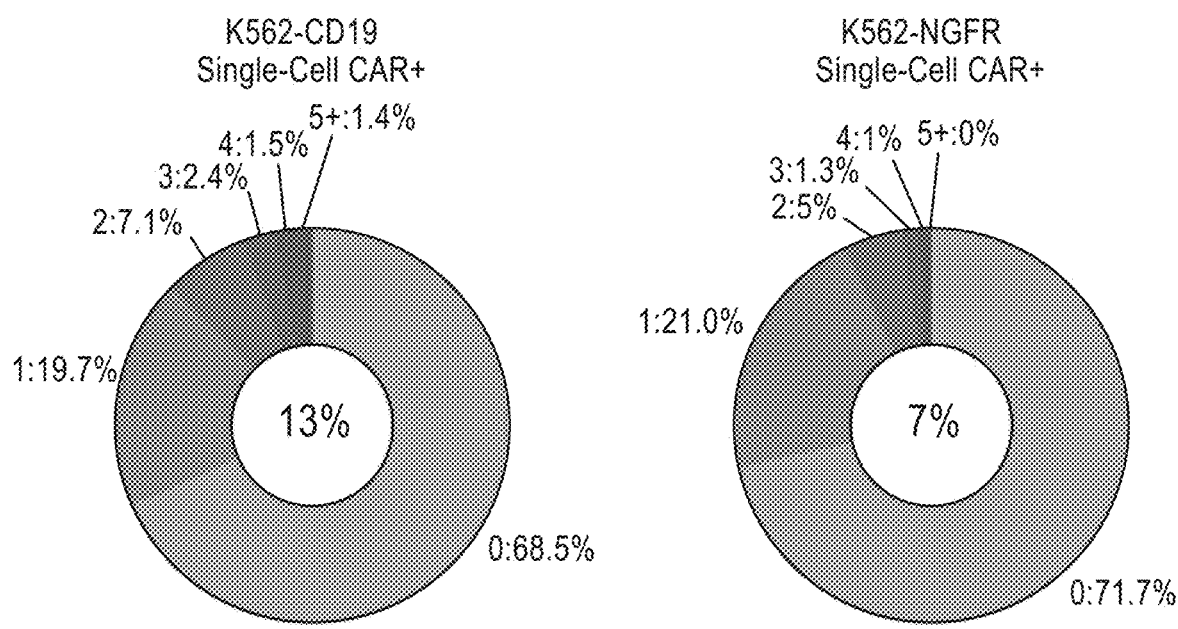
Figure 8G:
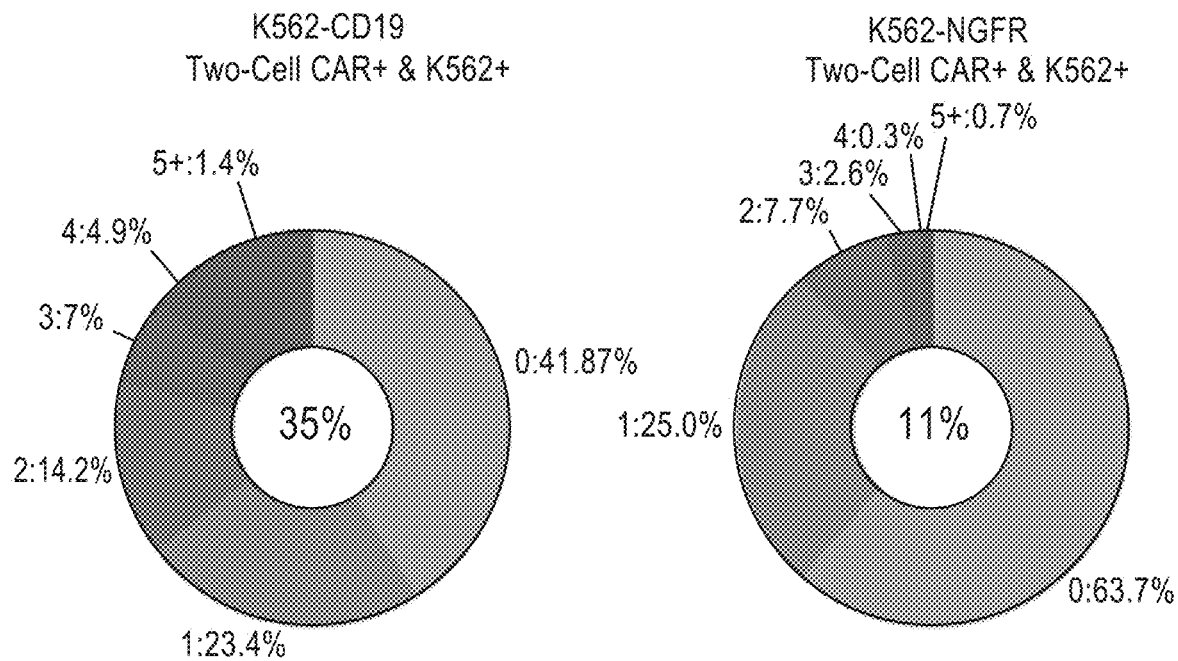
Figure 9:
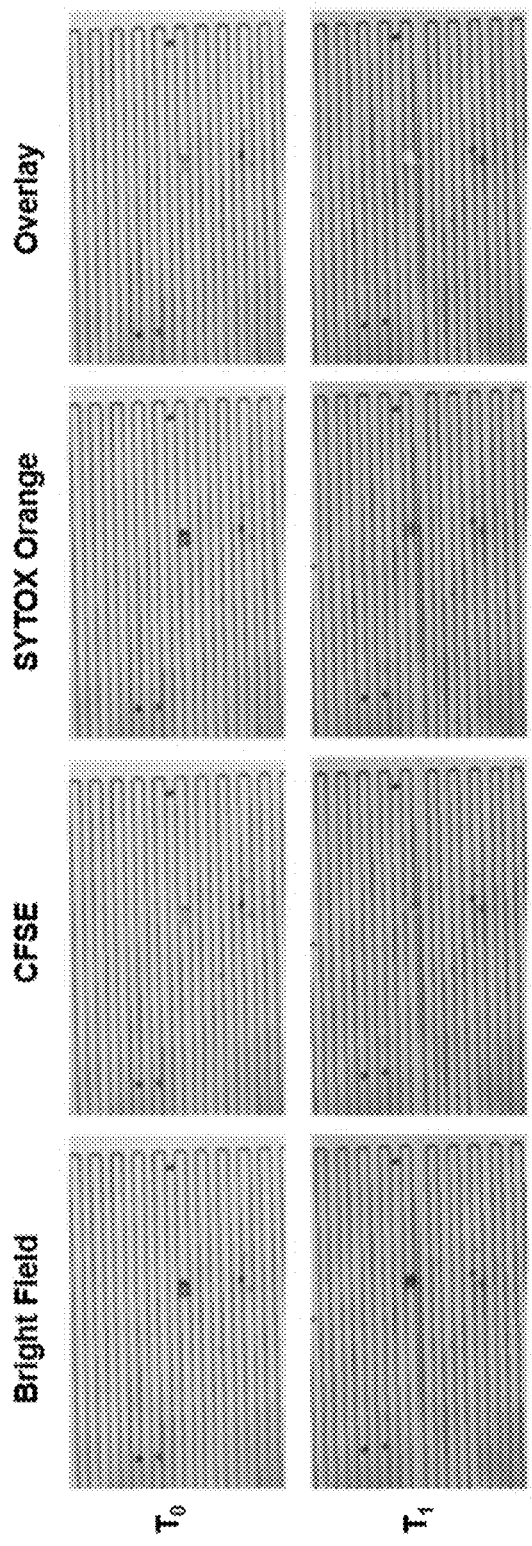

FIG. 9 is a series of photographs depicting systems of the disclosure and the use of fluorescent tracking of cytotoxicity. K562 cells, labeled with the membrane dye CFSE, are mixed with non-labeled NK cells and loaded into chambers (taking the form of micro-troughs for this example) with an excess of SYTOX Orange. The chambers (taking the form of micro-troughs for this example) are imaged immediately after loading (TO) and then again after a 16 hour incubation (TI) and assessed for cell death via fluorescence.

Figure 10A:
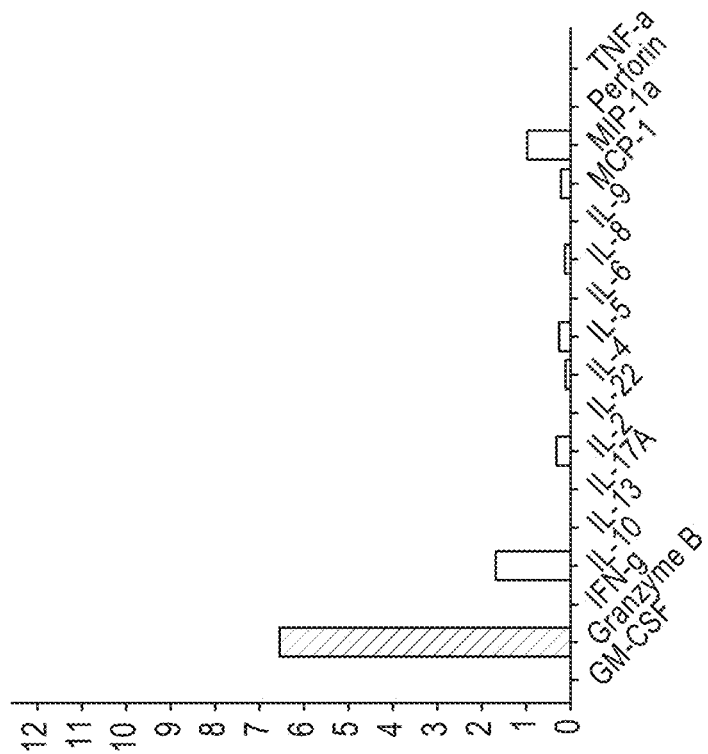
Figure 10A:
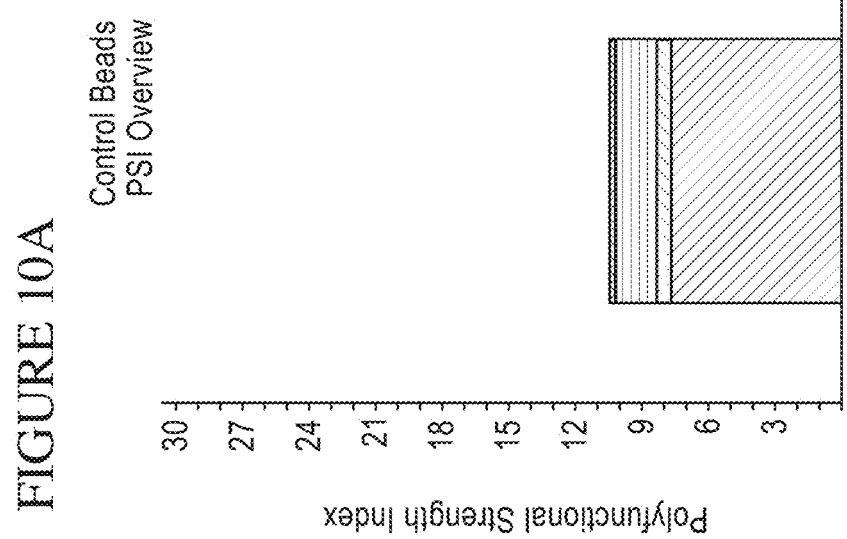
Figure 10B:
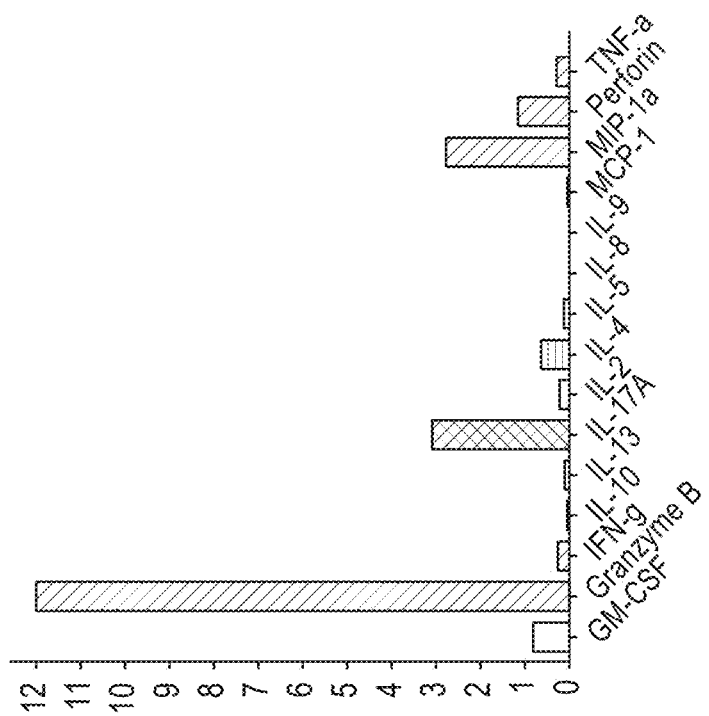
Figure 10B:
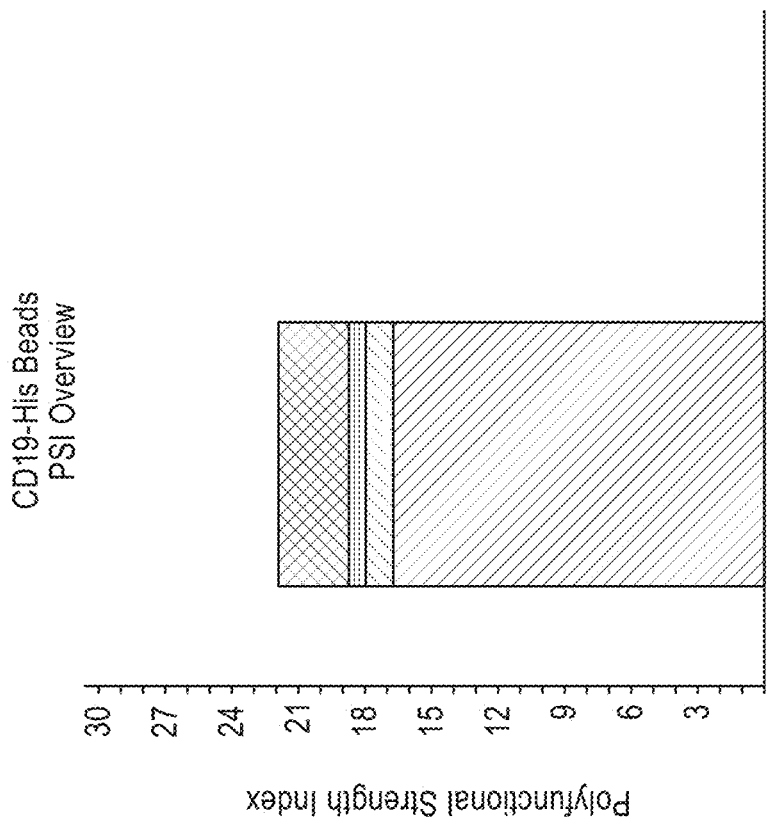
Figure 10C:
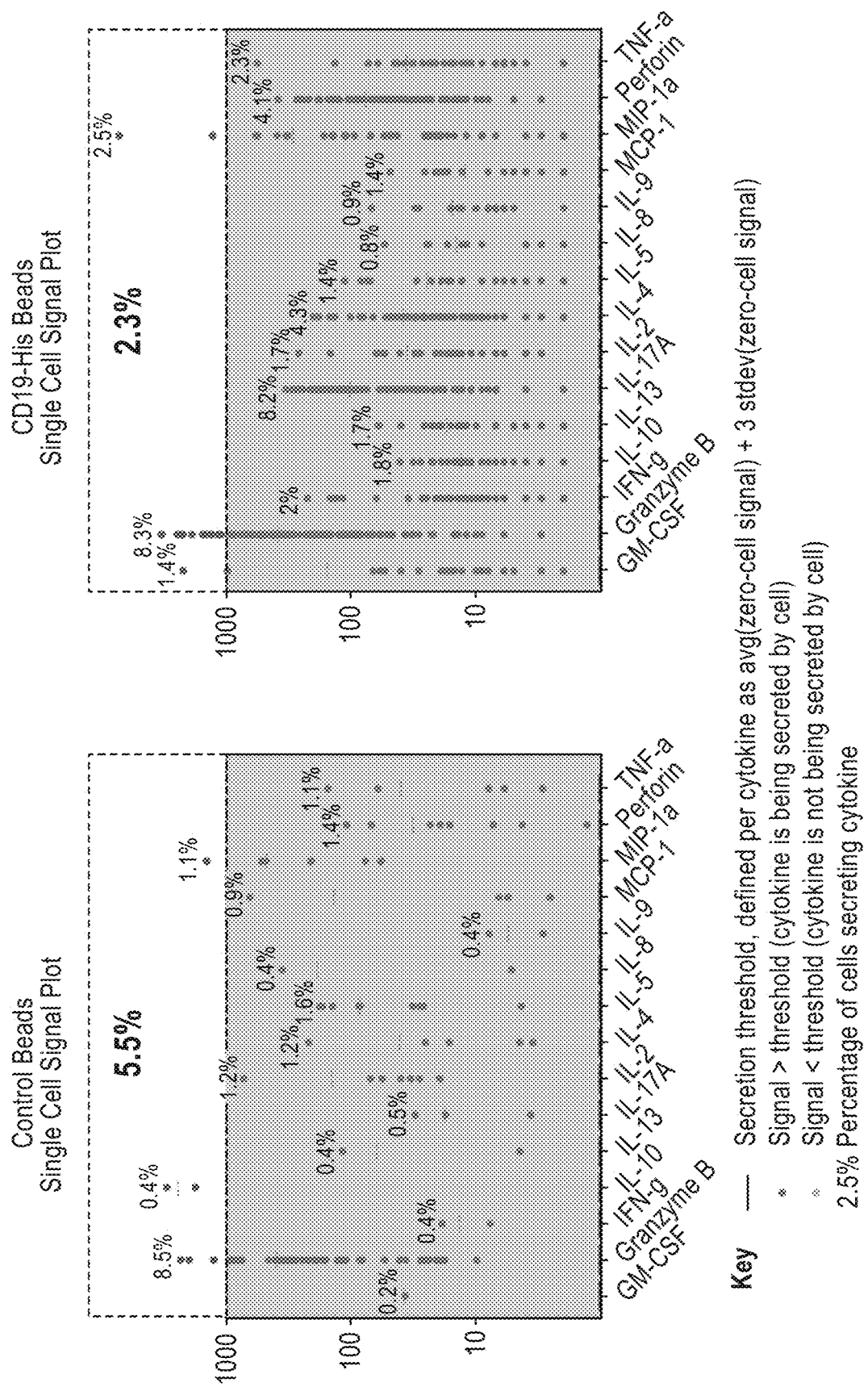

FIG. 10A-C is a series of signal plots of control and stimulated CAR (chimeric antigen receptor expressing) cells. Panel A. PSI (poly-functional strength intensity) Overview and Individual Cytokine contributions from control CAR cells. Panel B. PSI Overview and Individual Cytokine contributions from stimulated CAR cells (stimulated cells were contacted to CD19-conjugated beads). Panel C. Individual signal plots of both control and stimulated CAR cells.

FIG. 11A-F is a series of graphs depicting signals detected from CAR cells stimulated by target cells. PSI Overview from CAR cells stimulated with K562-NFGR control cells (A) or K562-CD19 (B) target cells. Individual Cytokine contributions from CAR cells stimulated with K562-NFGR (C) and K562-CD19 (D). The final plots show signal cell secretion points from CAR cells stimulated with K562-NGFR (E) or K562-CD19 (F).

FIG. 12A-M is a series of graphs comparing results of Memorial Sloan-Kettering Cancer Center (MSKCC) assays of cytokine secretion to exemplary detection sensitivities of the compositions, systems and methods of the disclosure (referred to as "IsoPlexis" in the figure). In the study by MSKCC (Brenthens et al. Blood. 2011 Nov. 3; 118(18): 4817-4828), safety and persistence of adoptively transferred autologous CD19-targeted T cells in patients with relapsed or chemotherapy refractory B-cell leukemias, MSKCC stimulated EOP 19-28z transduced T cells with 3T3 fibroblasts expressing CD19 for 48 hours. MSKCC then analyzed the cytokine secretion levels from the transduced cells on a Luminex IS100 to determine pg/mL amounts of analyte. The compositions, systems and methods of the disclosure can gather the same type of data as the MSKCC assay with equal or greater sensitivity as the MSKCC assay. The above side-by-side graphs show the sensitivity, per analyte, on the compositions, systems and methods of the disclosure versus the amounts measured from the MSKCC Luminex assay. The measurements from the MSKCC assay clearly fall within the measurable range of the compositions, systems and methods of the disclosure (a concentration of cytokines between about 2 pg/ml and about 10,000 pg/ml, inclusive of the endpoints, per cytokine in a highly multiplexed reaction). Therefore the same data could have been gathered using the compositions, systems and methods of the disclosure with the additional benefit of being able to transform this data to represent the Polyfunctional Strength Index (PSI) of individual cell populations. PSI measurements for each cytokine of a plurality of cytokines for each cell in a large-scale experiment (simultaneously measuring thousands of individual cells within a population), enables a prediction of statistically powerful biomarker and cell subsets that drive patient responses.

FIG. 13A-B is a pair of tables comparing results of National Cancer Institute cytokine assays of secretions from CARs to exemplary detection sensitivities of the compositions, systems and methods of the disclosure (referred to as "IsoPlexis" in the figure). In the study by NCI (Kochenderfer et al. Blood, 22 Mar. 2012, 119(12): 2709-2720), B-cell depletion and remissions of malignancy along with cytokine-associated toxicity in a clinical trial of anti-CD19 chimeric-antigen-receptor-transduced T cells, the NCI cultured CD19 directed CAR cells with either CD19-positive K562 cells or the control NGFR-positive (CD19-negative) overnight and ran the cytokine secretions next day on a standard ELISA assay. Cytokine secretion levels for IFN-gamma, TNF, and IL-2 are listed in the top table. In the bottom table, are listed the limits of detection on the compositions, systems, and methods of the disclosure, with either a signal-to-noise ratio (SNR) of greater than 2 or greater than 5. The compositions, systems, and methods of the disclosure are able to measure cytokine secretions, with great confidence, in the same range as those measured by standard ELISA in this NCI study with the additional benefit of being able to transform this data to represent the Polyfunctional Strength Index (PSI) of individual cell populations. PSI measurements for each cytokine of a plurality of cytokines for each cell in a large-scale experiment (simultaneously measuring thousands of individual cells within a population), enables a prediction of statistically powerful biomarker and cell subsets that drive patient responses.

Figure 14A:
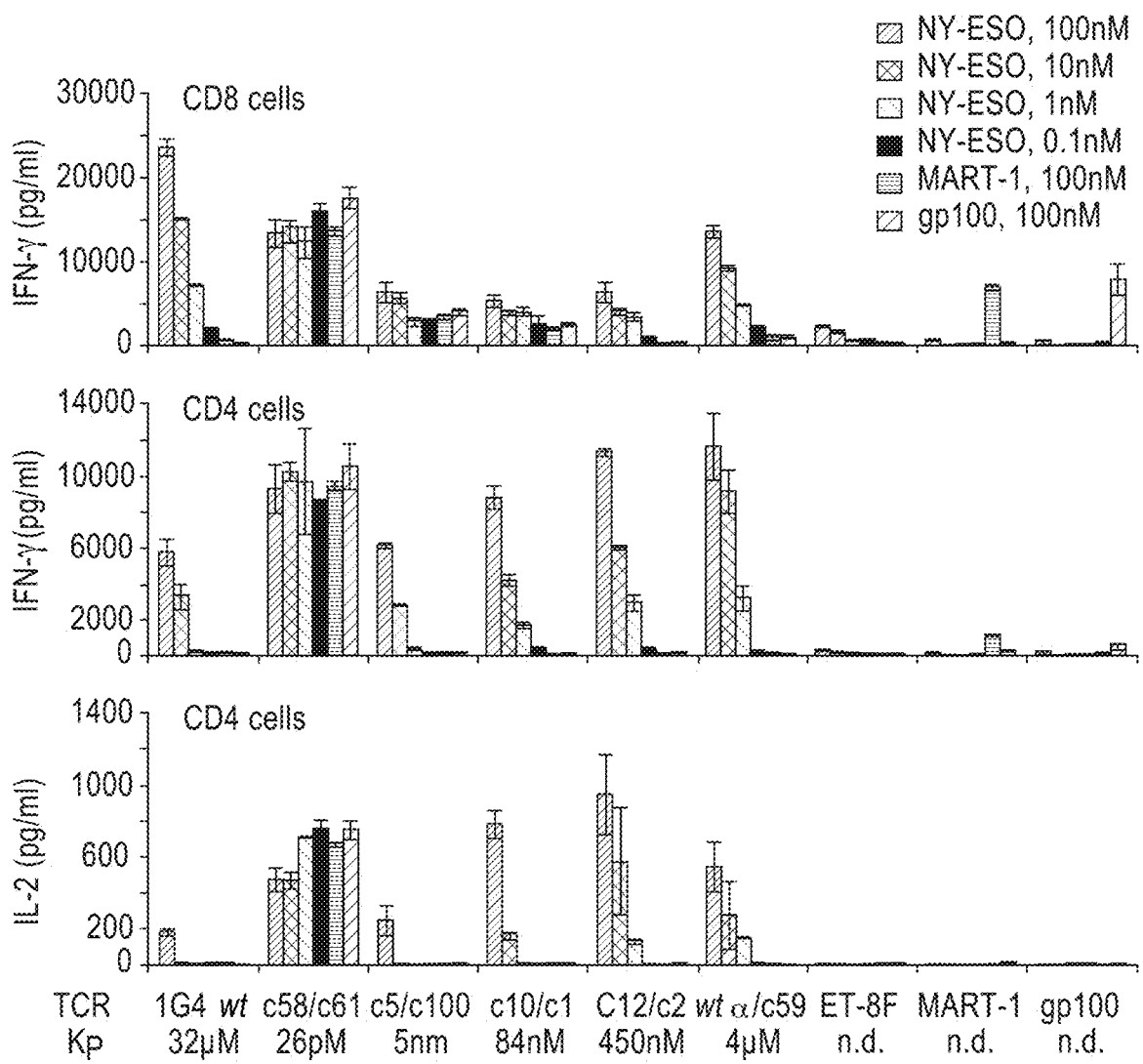
Figure 14B:
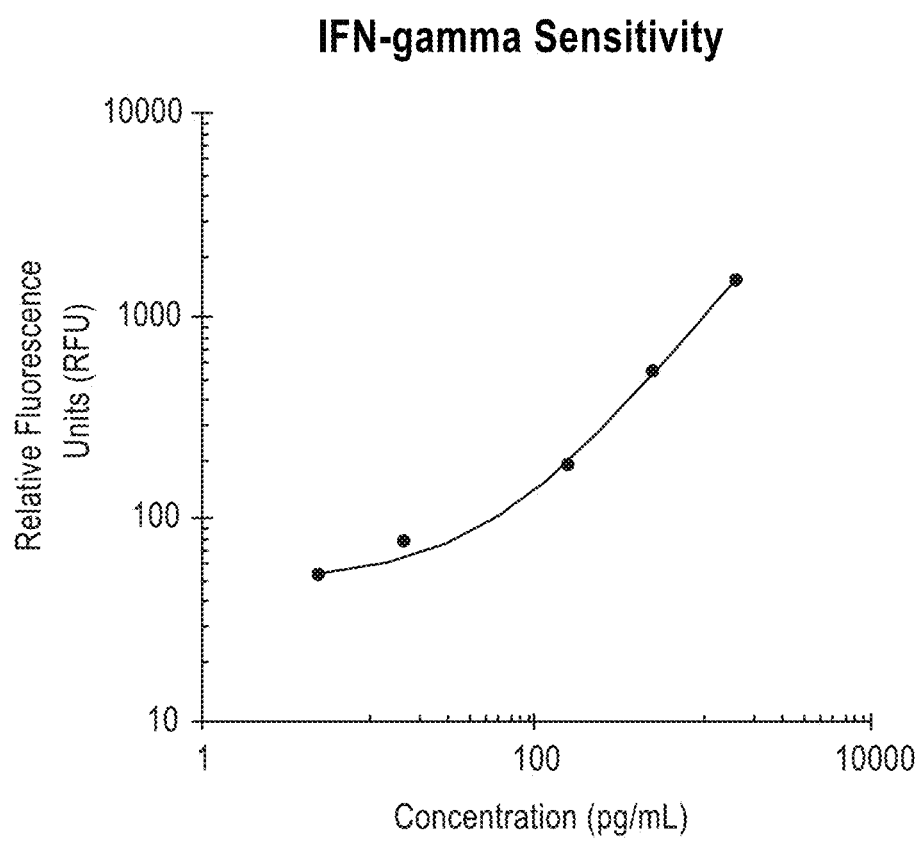
Figure 14C:
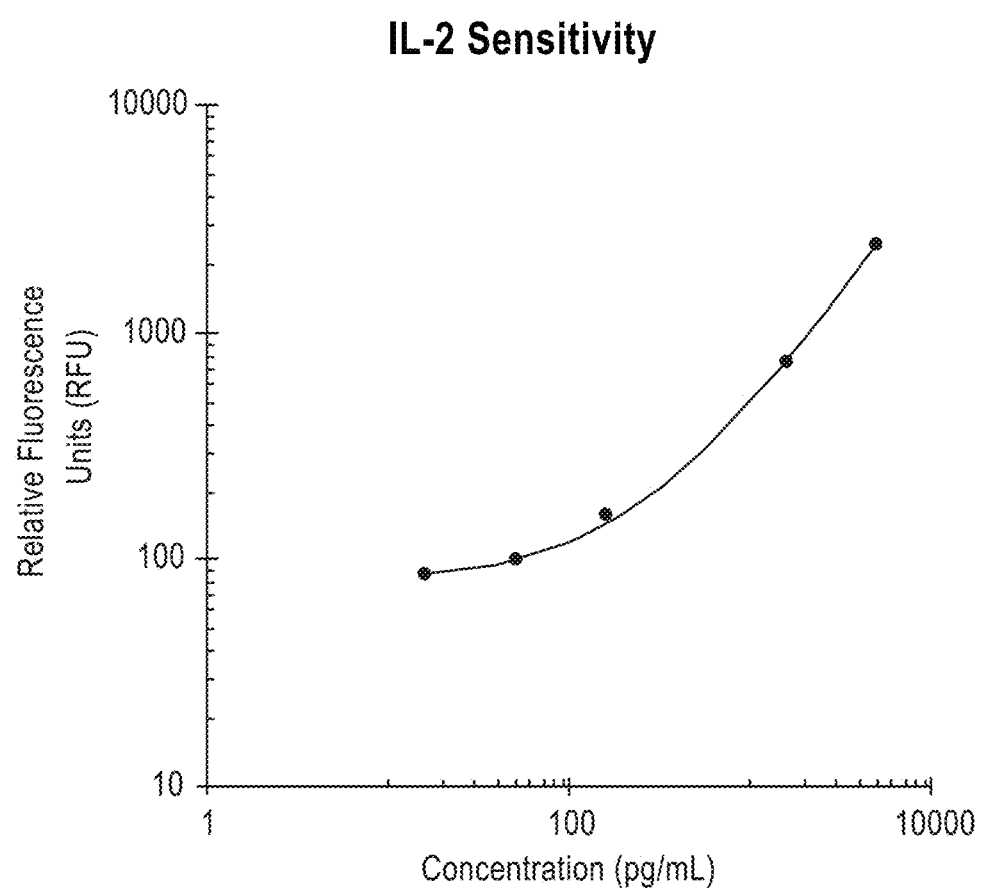

FIG. 14A-C is a series of graphs comparing results of National Cancer Institute cytokine assays of secretions from CARs to exemplary detection sensitivities of the compositions, systems and methods of the disclosure (referred to as "IsoPlexis" in the figure). In the study by NCI (Zhao et al. The Journal of Immunology, 2007, 179: 5845-5854), high-affinity TCRs generated by phage display provide CD4+ cells with the ability to recognize and kill tumor cell lines, the NCI measured the cytokine secretions from TCR-transfected T cells. CD8+ and CD4+ T cells were purified and transfected with the TCRs. The cells were then pulsed with NY-ESO-1, MART-1 or gp100 peptides, and the resulting secretions of IL-2 and IFN-gamma were measured using commercially available ELISA kits at a range of between 200 pg/mL and 30,000 pg/mL, inclusive of the endpoints. The compositions, systems and methods of the disclosure are able to measure cytokine secretions, with great confidence, in the same range as those measured by standard ELISA in this NCI study with the additional benefit of being able to transform this data to represent the Polyfunctional Strength Index (PSI) of individual cell populations. PSI measurements for each cytokine of a plurality of cytokines for each cell in a large-scale experiment (simultaneously measuring thousands of individual cells within a population), enables a prediction of statistically powerful biomarker and cell subsets that drive patient responses.

Figure 15:
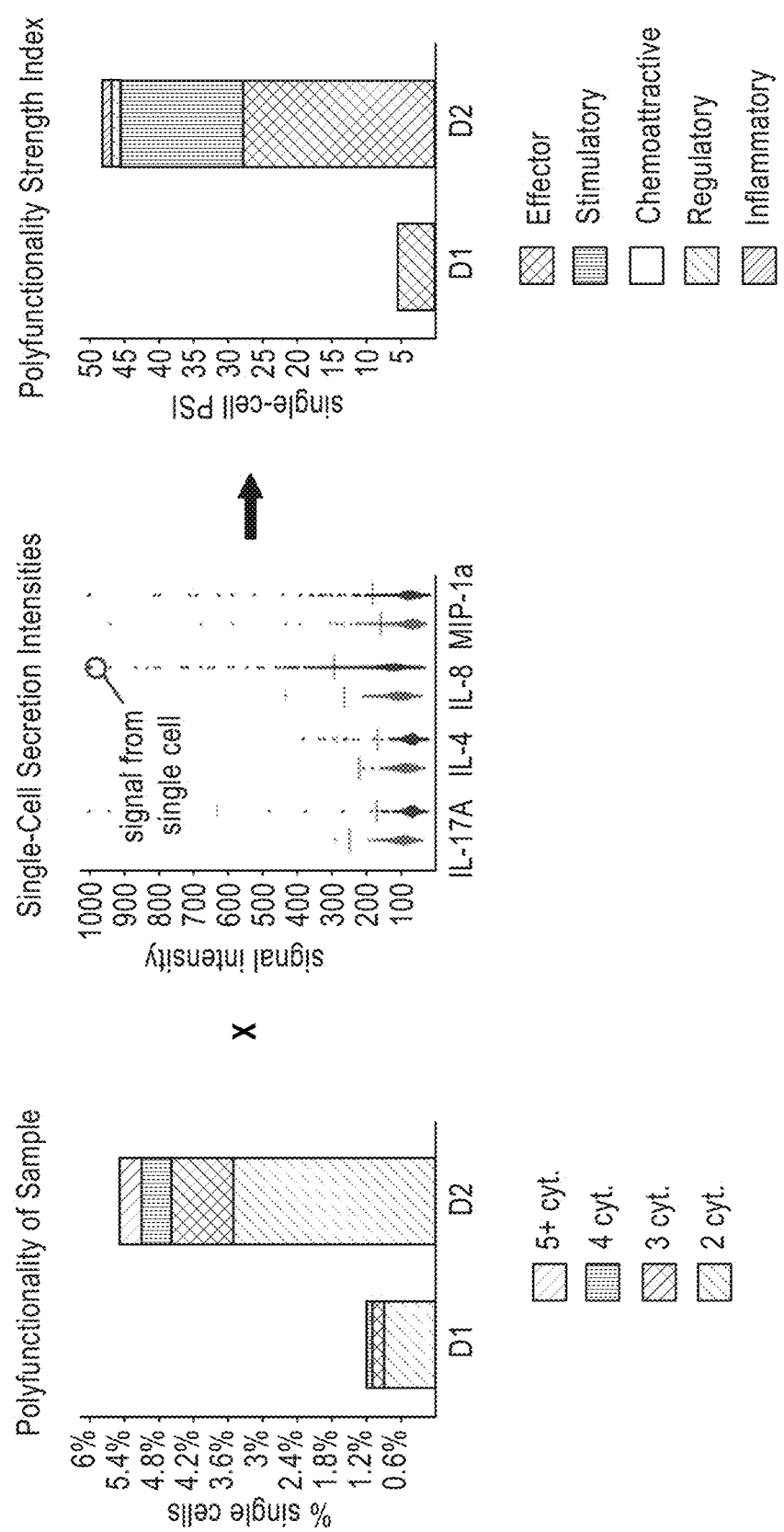

FIG. 15 is a series of graphs depicting a method of measuring single-cell Polyfunctional Strength Index (PSI). This metric quantifies the overall activity of a sample. The PSI is equal to the percentage of polyfunctional cells (secreting two or more cytokines) in a sample multiplied by the average signal intensity of the secreted cytokines. In order to determine which cytokines are driving the polyfunctional response, each individual cytokine's contribution to PSI can also be calculated. This is equivalent to the fraction of the total PSI coming from a specific cytokine, and is found by calculating the percentage of each cell's signal corresponding to that cytokine, averaging it across all cells, and multiplying this percentage by the total PSI.

DETAILED DESCRIPTION

The disclosure provides systems and methods capable of measuring key effector proteins at the single cell level. For example, in certain embodiments, the systems and methods of the disclosure can simultaneously measure 42 key effector proteins at the single cell level. The systems and methods of the disclosure may be used, for example, directly in pipeline drug development and CAR-T assessment by large-scale developers of cell-based therapeutics. The multiplexed parameters measured by the systems and methods of the disclosure cover, for example, the complete range of relevant immune effector functions including stimulatory, proinflammatory, regulatory (negative), chemoattractive, pro-growth and cytolytic (effective).

The systems and methods of the disclosure require smaller amounts of cell input (approximately 1000 cells) compared to the existing single-cell instruments (e.g., flow cytometer) for the analysis of low quantity patient samples, which minimally 100,000 cells per sample for analysis (and typically require millions of cells per sample).

The systems and method of the disclosure provide an analytical approach capable of evaluating single cell secretion profiles in a highly multiplex manner. In certain embodiments, this analysis involves crosstalk of a single immune cell to a diseased target cell (i.e. direct or indirect contact of a subject cell and a target cell) while avoiding or minimizing paracrine effects from the total population (because each pair of subject cell and target cell may be isolated into a chamber separated from the remaining plurality of chambers). This approach enables the study and detection of rare subject to target cell interactions that may be otherwise masked by other cells within the population or sample.

The systems and methods of the disclosure are exemplified in a nonlimiting manner through demonstrating the ability of a system of the disclosure to evaluate individual cell-to-cell interactions for the Target/Effector relationship of immune cells, including CAR cells, with various target cells or stimulatory agents according to a method of the disclosure. Highly multiplexed paired immune and cancer cell assays provide mechanisms for assessing a polyfunctional cytokine profile at the single cell level, in response to a cancer cell and its specific antigens. Such assays may further be used to evaluate the immune response quality in relation to the magnitude of an immune cell response to a cancer cell. Even more, such assays may be used to correlate the immune response quality and/or the magnitude of an immune cell response to a cancer cell with the ability of the immune cell to kill the cancer cell. Accordingly, the systems and method of the disclosure provide novel tools for addressing the critically relevant needs of identifying and evaluating cellular therapies for safety and efficacy in the field of cancer immunology, among many other fields.

The systems and methods of the disclosure provide the ability to analyze cells in a highly multiplexed fashion, down to the single-cell level and are capable of determining the polyfunctional response to a specific diseased cell. While an exemplary method includes monitoring killing of a target tumor cell, by an immune cell, within a chamber, for purposes of correlating with a highly multiplexed immune response, the systems and methods of the disclosure include many other applications.

As shown in the Figures of the disclosure, and in particular, FIGS. 7, 8, 10, and 11, polyfunctionality is a measure of efficacy and potency of cells intended for cellular therapy. Of particular value is the polyfunctional strength index (PSI). The polyfunctional strength index (PSI) is a metric that factors in the polyfunctionality of cells in a sample, and the signal intensity of the cytokines secreted by each cell. It is found by multiplying the percentage of polyfunctional cells of a sample (single cells secreting two or more cytokines), by the average signal intensity of these cytokines. This PSI is shown on the left of FIGS. 10A and 10B, as well as FIGS. 11A and 11B. For example, FIG. 10B demonstrates that the polyfunctional strength is roughly 2× higher in the CD19 stimulated sample, relative to the control PSI shown in FIG. 10A. FIG. 11B demonstrates that the stimulated cells have a polyfunctional strength roughly 5× higher than the control cells. For more detail regarding PSI, see Example 7.

Methods of Analyzing Immune Cells

Secreted proteins and in particular cytokines, are key mediators of intercellular communication within the immune system. Homeostatic immune response requires tightly regulated cytokine synthesis and secretion. Many analytical technologies have been developed to analyze protein secretion during the immune response, but the methods used are generally restricted to measuring the average secretions for an entire cellular population. Such analyses, while helpful in understanding disease pathogenesis and the immune process, are insufficient to characterize cytokine activity for individual subsets of cells within a population. Recent investigations using single-cell analysis have shown that immune cells display highly heterogeneous cytokine profile even in cells with similar phenotypes further demonstrating a significant limitation of focusing only on cellular response at the bulk population level. These heterogeneous subsets of cells within the population may dictate a complex signaling interplay between cells that represent important checks and balances for disease immunotherapy evaluation. This is particularly notable when a cellular population's response can be determined by the cell-cell interactions in a rare subset of cells. As a result, understanding these interactions is crucial to developing more effective therapeutic treatments in the future.

Challenges to defining consistent and high functional quality "drug" in cell-based cancer immunotherapy: Despite the demonstrated benefit of emerging CAR-T cancer immunotherapeutics, two major concerns remain: one, manufacturing the cell therapies consistently, and two, managing the immuno-toxicity, such as cytokine release syndrome, that could be potentially life threatening. In cell-based therapies such as Chimeric Antigen Receptor T cell (CAR-T) therapy, in which the living cells are the "drug", cellular manufacturing is still relatively new, and each patient batch generated may differ substantially even if a standardized operation procedure (SOP) exists to ensure consistency in manufacturing. Giving clinicians and biotech companies an effective cellular function monitoring tool could change clinical paradigms by allowing them to remove or modify the inconsistent or unsafe cell therapies prior to injection, significantly reducing risk to the patient, and improving odds of therapeutic success.

Defining the "quality" of a cytokine mediated anti-tumor T cell: To evaluate engineered T cells for an immunotherapy or to evaluate endogenous T cells reactivated to battle cancer or infection, a T cell's functional status is largely determined by a spectrum of secreted effector function proteins (e.g., cytokines). In a protective immune response, the 'quality' of an immune cell correlates to the extent of polyfunctionality (the ability of a T cell to co-secrete multiple effector proteins). While these anti-tumor cytolytic, chemoattractive cytokines produce an effective response, these poly-functional cell subsets must not also secrete immuno-toxic inflammatory or regulatory cytokines (up to 15) prevalent in NK or CAR-T cells. To detect consistent performance of this "quality" effective and safe response of CAR single-cell subsets, a need exists for a new technology to conduct highly multiplexed measurement of immune effector proteins in single T cells. And while single-cell flow cytometry technologies fix cells to detect cytokines, a more predictive platform would detect true secretions.

Current methods of cell function evaluation: Single parameter ELISpot assay remains the state-of-the-art for T cell activation assay, but does not measure polyfunctionality. Averaging bead based multiplexing platform (Luminex based) measure many cytokines, yet not at the required single-cell level. Fluorescence-based multicolor flow cytometry is a powerful single cell analysis tool and has been used to detect cytokines via retaining and staining proteins within the cytoplasm by blocking vesicle transport. The number of proteins that can be simultaneously measured is limited by fluorescence spectral overlap with ICS (intracellular cytokine staining). Time-of-flight mass spectrometer-coupled flow cytometry (CyTOF) has been used recently by CAR-T companies, though not as regularly in trials. Similar to fluorescence flow cytometry, it does not measure true secretion and so far the number of cytokines co-measured in single cells by CyTOF is 11 due in part to the high background of ICS. Other single cell technologies being developed in research laboratories (e.g., microengraving) provides advantages in sensitivity and assay speed but still limited in the multiplexing capability (typically <5).

Risks involved in adoptive cell therapies and other immune mediated therapies: Cytokine release syndrome (CRS) is a non-antigen specific, life-threatening toxicity that results from the over-activation of the immune system due to immune therapies, such as CAR T-cell therapy. Although CAR T-cells are potent on-target killers, they activate the immune system far above naturally occurring levels and due to the nature of their design, have a large degree of "on target, off tumor" toxicity. Based on the level of mortalities in recent clinical trials, it has become apparent that the cytokine profiles of individual CAR-T cells must be known before introduction to the patient. The systems and methods of the disclosure determine an abundance of up to 42 cytokines, per single cell, falling into the following groups: effector, stimulatory, inflammatory, and regulatory. This information allows the user to identify any potentially toxic subsets of cells (pro-inflammatory or regulatory) within a population that would have been missed by conventional means, providing a safer and more effective means of monitoring immunotherapies prior to patient introduction.

Systems and Arrays

The disclosure provides a system for the multiplexed detection of a plurality of compounds from single cells comprising an array comprising a plurality of chambers and a panel of capture agents. Preferred capture agents include antibodies, however, capture agents may include any detectable entity that specifically binds to a component of a secretome of the disclosure. The detectable entity may comprise a detectable label, for example. Detectable labels may include, but are not limited to fluorescent labels.

Systems of the disclosure comprise a plurality of individual chambers, preferably in uniform arrangement. In certain embodiments, at least some of the plurality of individual chambers have a length of greater than 50 [tm and, optionally, may be configured to contain an isolated single cell in a sub-nanoliter volume of contents.

Capture agent panels of the disclosure may comprise a plurality of immobilized capture agents, each immobilized capture agent capable of specifically binding to one of the plurality of components of a secretome of the disclosure. Preferably, the immobilized capture agents are arranged in uniform capture agent panels. Preferably, the immobilized capture agents are attached to a surface in a repeatable pattern, wherein each repeat of the pattern aligns with a chamber of the plurality of chambers.

The array and capture agent panels are coupled to form a plurality of enclosed interfaces, each enclosed interface comprising a chamber and a capture agent panel such that the contents of each chamber are accessible to each and every capture agent of the capture agent panel.

Chambers of the array may take on any shape and may have any dimension, however, in certain embodiments of the disclosure, the array comprises at least 1, 2, 5, 10, 15, 20, 25, 50, 100, 150, 500, 1000, 1500, 2000 or any integer between of chambers. Each chamber may have a depth/height of between 1 µm and 2000 [tm, a diameter of between 1 µm and 2000 [tm, a width of between 1 µm and 2000 [tm and/or a length of between 1 µm and 2000 [tm. The distance between any two chambers of the array may be between 1 [tm and 2000 [tm.

In certain embodiments, at least one chamber is a high aspect ratio rectangular well, having dimensions of about 1-2 mm in length and about 5-50 [tm in depth.

In certain embodiments, each chamber is rectangular with a length of about 10-2000 [tm, a width of about 10-100 [tm, and a depth of about 10-100 [tm.

In certain embodiments, the capture agent panel may comprise between 3 and 50 different capture agents, thereby allowing for the detection of between 3 and 50 different components of a secretome. In certain embodiments, the capture agent panel may comprise greater than 3 different capture agents, thereby allowing for the detection of greater than 3 different components of a secretome. In certain embodiments, the capture agent panel may comprise greater than 10 different capture agents, thereby allowing for the detection of greater than 10 different components of a secretome. In certain embodiments, the capture agent panel may comprise greater than 42 different capture agents, thereby allowing for the detection of greater than 42 different components of a secretome.

In certain embodiments, the array comprises a chamber density of about 200 microwells per $cm^2$ to about 20,000 microchambers per $cm^2$.

Definitions

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The following definitions are useful in understanding the present invention:

The term "antibody" (Ab) as used herein includes monoclonal antibodies, polyclonal antibodies, multispecific antibodies (e.g., bispecific antibodies), and antibody fragments, as long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Capture agents of the disclosure may comprise one or more monoclonal antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies.

Monoclonal antibodies contemplated herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Capture agents of the disclosure may comprise humanized antibodies. A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed by substituting import hypervariable region sequences for the corresponding sequences of a human antibody. Accordingly, such "humanized" antibodies are chimeric antibodies wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

Capture agents of the disclosure may comprise intact antibodies. An "intact" antibody is one that comprises an antigen-binding site as well as a CL and at least heavy chain constant domains, CH 1, CH 2 and CH 3. The constant domains may be native sequence constant domains (e.g., human native sequence constant domains) or amino acid sequence variant thereof. Preferably, the intact antibody has one or more effector functions.

Capture agents of the disclosure may comprise an antibody fragment. An "antibody fragment" comprises a portion of an intact antibody, preferably the antigen binding or variable region of the intact antibody. Examples of antibody fragments include Fab, Fab', F(ab')2, and Fv fragments; diabodies; linear antibodies; single-chain antibody molecules; and multispecific antibodies formed from antibody fragments.

Capture agents of the disclosure may comprise a functional fragment or an analog of an antibody. The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Feat"

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH 1). Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

Capture agents of the disclosure may comprise single-chain antibodies (also referred to as scFv). "Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

Capture agents of the disclosure may comprise diabodies. The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natd. Acad. Sci. USA, 90:6444-6448 (1993).

Capture agents of the disclosure may comprise bispecific antibodies. In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen.

Methods for making bispecific antibodies are known in the art. Traditional production of full length bispecific antibodies is based on the co-expression of two immunoglobulin heavy chain-light chain pairs, where the two chains have different specificities. Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low.

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

As used herein, an antibody is said to be "immunospecific," "specific for" or to "specifically bind" an antigen if it reacts at a detectable level with the antigen, preferably with an affinity constant, $K\alpha$, of greater than or equal to about $10^4$ M", or greater than or equal to about $10^5$ M", greater than or equal to about $10^6$ M", greater than or equal to about $10^7$ $M^1$, or greater than or equal to $10^8$ M". Affinity of an antibody for its cognate antigen is also commonly expressed as a dissociation constant KD, and in certain embodiments, an antibody specifically binds to a component of a secretome if it binds with a KD of less than or equal to 10' M, less than or equal to about $10^{-5}$ M, less than or equal to about 10' M, less than or equal to 10' M, or less than or equal to $10^{-8}$M. Affinities of antibodies can be readily determined using conventional techniques, for example, those described by Scatchard et al. (Ann. N.Y. Acad. Sci. USA 51:660 (1949)).

Subject and target cells of the disclosure may be isolated, derived, or prepared from any species, including any mammal. A "mammal" for purposes of treating n infection, refers to any mammal, including humans, domestic and farm animals, and zoo, sports, or pet animals, such as dogs, cats, cattle, horses, sheep, pigs, goats, rabbits, etc. Preferably, the mammal is human.

Subject cells of the disclosure may be used in a cellular therapy for the treatment of a disease or disorder. "Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal may be successfully "treated" when, after receiving a cellular therapy with a subject cell of the disclosure, the patient shows observable and/or measurable reduction in or absence of one or more of the following: reduction in one or more of the symptoms associated with disease or disorder; reduced morbidity and mortality, and improvement in quality of life issues. The above parameters for assessing successful treatment and improvement in the disease are readily measurable by routine procedures familiar to a physician. Methods of the disclosure may be used to determine the safety and/or efficacy of a cellular therapy before, during or after initiation of treatment of the subject.

Capture agents of the disclosure may be labeled to render them detectable using one or more means. "Label" as used herein refers to a detectable compound or composition that is conjugated directly or indirectly to the capture agent (e.g. an antibody) so as to generate a "labeled" capture agent (e.g. an antibody). The label may be detectable by itself (e.g., a fluorescent label) or, in the case of an enzymatic label, may catalyze chemical alteration of a substrate compound or composition that is detectable.

Capture agents of the disclosure may selectively or specifically identify, capture, and/or quantify one or more small molecules in a secretome. A "small molecule" is defined herein to have a molecular weight below about 500 Daltons.

Capture agents of the disclosure may include nucleic acids or labeled nucleic acids. The terms "nucleic acid" and "polynucleotide" are used interchangeably herein to refer to single- or double-stranded RNA, DNA, or mixed polymers. Polynucleotides may include genomic sequences, extragenomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the disclosure and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (3.9); and arginine (−4.5).

Certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. The substitution of like amino acids can be made effectively on the basis of hydrophilicity. The greatest local average hydrophilicity of a protein, as governed by the hydrophilicity of its adjacent amino acids, correlates with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 Methods in Enzymology vol. 183, Academic Press, Inc., San Diego, CA; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, CA; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J Mol. Biol.* 48:443, by the search for similarity methods of Pearson and Lipman (1988) *Proc. Natd. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

As used in this specification and the appended claims, the singular forms "a," "an" and "the" include plural references unless the content clearly dictates otherwise.

EXAMPLES

The methods detailed below are capable of analyzing distinct single subject cell to single target cell interactions on a system of the disclosure (also referred to below as an array). Cell populations may be cultured separately and briefly mixed before being loading onto the array. The array may comprise a plurality of chambers (which, for these examples, may take the form of micro-troughs) that are enclosed by surface (e.g. a glass slide or other cover material) creating isolated microenvironments for high throughput cellular studies such as paired cell interactions. The surface enclosing each chamber of the array may have attached thereto one or more detection agents (including, but not limited to antibodies). The detection agents (e.g. antibodies in the Examples provided below) may be attached to the surface in a repeated pattern such that each chamber comprises one repeat of the pattern on the portion of the surface enclosing the chamber. In this circumstance, each repeat of the pattern comprises at least one of every individual detection agent (e.g. antibody specific for a particular cytokine). The surface may have attached thereto between 20-1000 detection agents that are each specific for a distinct component of a subject cell's secretome. The systems of the disclosure include a plurality of chambers. The plurality of chambers may include, for example, between 2 and 2000 chambers.

Example 1: Analysis of Natural Killer (NK) Cell and Target Cell

Cell Culture. Isolated peripheral blood mononuclear cells (PBMCs), stored in-house at a concentration of $2.5 \times 10^7$ cells/vial, were thawed and cultured overnight in a T25 cell culture flask with 5 mL of X-Vivo 15 without Gentamicin or phenol red (Lonza, 04-744Q) supplemented with 1× GlutaMAX (ThermoFisher, 35050061), 1 mM sodium pyruvate (ThermoFisher, 11360-070), 1×MEM Vitamin Solution (Gibco; ThermoFisher, 11120-052), 20 mM HEPES (Gibco; ThermoFisher, 15630-080), 2% Human AB serum (Valley Biomedical, HP1022HI), 1× Penicillin-Streptomycin-Neomycin (Sigma-Aldrich, P4083), 100 ng/mL recombinant IL-18 (R&D Systems, B001-5) and 10 ng/mL IL-12 (R&D Systems, 219-IL-005). After an overnight recovery, NK cells were isolated using the Miltenyi NK Cell Isolation Kit according to the manufacturer's instructions. NK cells were then cultured at 37° C., 5% CO2 in supplemented X-Vivo 15 media at a concentration of $1 \times 10^6$ cells/mL until use. A human K562 Cell line (ATCC CCL243) was purchased from the American Type Culture Collection (ATCC) and cultured in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083) and 1× GlutaMAX supplement (ThermoFisher, 35050061).

Single-Cell Secretome Assay. Before performing the single cell assay, the system of the disclosure (in this example, a polydimethylsiloxane (PDMS) microchamber array) was plasma treated for 2.5 minutes with a Plasma Etch PE-25 plasma cleaner to increase hydrophilicity. The array was then blocked in 3% BSA/PBS for 30 minutes. Immediately prior to the assay, K562 cells were taken from culture, resuspended in 1 mL of PBS and stained with CellTrace Carboxyfluorescein succinimidyl ester (CFSE) (1:1000, ThermoFisher) for 20 minutes. K562 cells were then washed 3× with supplemented X-Vivo 15 media and resuspended at a concentration of $1 \times 10^6$ cells/mL. K562 cells and NK cells were then combined at a 1:1 ratio to generate a cell suspension. This suspension containing K562 cells and NK cells was centrifuged at 300×g for 10 minutes and re-suspended in fresh media at a concentration of $2.5 \times 10^6$ cells/mL. Immediately before the assay, the array was rinsed with media and dried using compressed air. The array was positioned onto a glass slide and secured into a custom clamping system. Thirty microliters of the cell suspension was pipetted, chamber-by-chamber, onto the array. A surface (a glass side in this example) with the a repeated pattern of antibodies attached thereto was contacted to the array such that the repeated pattern of antibodies was facing the array and such that each repeat of the pattern aligned with a chamber of the array. The array and the surface (with the antibody pattern) enclosing the array were clamped tightly together in our custom clamping system. Cells were trapped in microchambers and imaged immediately after loading as described below. The microchamber assembly was placed in a standard 5% CO2, incubator at 37° C. for 16 hours. Following incubation, the surface with the antibody pattern was removed in a 1% BSA/PBS bath and rinsed with 1% BSA/PBS. Subsequently, 300 [EL of a biotin-labeled secondary antibody cocktail was introduced to the surface and incubated for 45 minutes. This cocktail contains detection antibodies at a concentration of 0.25 [Eg/mL each in 1:200 suspension of 1% BSA/PBS. Following this step, the surface was rinsed with 1% BSA, 300 [EL of a 1:100 solution of APC streptavidin (BioLegend, 405207) was added and the surface was incubated for 30 minutes. Following this incubation, the surface was washed with 1% BSA/PBS then washed in coplin jars PBS, 50% PBS/DI water, DI water, DI water sequentially for 3 minutes in a centrifuge set at 125 rpm. The surface was dried for 30 seconds in a Labnet slide spinner (C1303-T). The surface was analyzed using a GenePix microarray scanner as described below.

Microchamber Array Imaging. A Zeiss Axio Observer.Z1 fluorescent microscope with an automatic stage was used to acquire both bright field and fluorescent images of the array. Images of the entire array were taken with a Hamamatsu Orca-Flash4.0 LT Digital CMOS camera (C11440-42U) of a 54183 uM×24866 uM area corresponding to either 253 tiles (5× image) or 494 tiles (10× image). Using Zen2 Pro software, the tiles were stitched together with 0% overlap and were exported as TIFFs for analysis by our proprietary CytoSpeak software.

Imaging of Antibody-Patterned Surface. GenePix 4400A scanners (Molecular Devices) were used to obtain scanned fluorescent images of the antibody-patterned surfaces. Two color channels, 488 (blue, PMT 350, Power 90) and 635 (red, PMT 600, Power 90) were used to collect fluorescence signals using GenePix Pro software (Molecular Devices). The image was then exported as a TIFF before analysis using CytoSpeak software.

Example 2: Analysis of CD8+ T-Cell and Target Cell with Bispecific Antibodies Cell Culture. Isolated PBMCs, stored in-house at a concentration of $2.5 \times 10^7$ cells/vial, were thawed and cultured overnight in a T25 cell culture flask with 5 mL of X-Vivo 15 without Gentamicin or phenol red (Lonza, 04-744Q) supplemented with 1× GlutaMAX (ThermoFisher, 35050061), 1 mM sodium pyruvate (ThermoFisher, 11360-070), 1×MEM Vitamin Solution (Gibco; ThermoFisher, 11120-052), 20 mM HEPES (Gibco; ThermoFisher, 15630-080), 2% Human AB serum (Valley Biomedical, HP1022HI), 1× Penicillin-Streptomycin-Neomycin (Sigma-Aldrich, P4083), and 4 ng/mL recombinant IL-2 (BioLegend). After an overnight recovery, CD8+ T-cells were isolated using the Miltenyi CD8+ T-Cell Isolation Kit according to the manufacturer's instructions. CD8+ T-cells were then cultured at 37° C., 5% CO2 in supplemented X-Vivo 15 media at a concentration of $1 \times 10^6$ cells/mL until use. The human Raji B Cell line (purchased from the American Type Culture Collection (ATCC)) was cultured in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083) and 1× GlutaMAX supplement (ThermoFisher, 35050061).

Single-Cell Secretome Assay. Before performing the single cell assay, the system of the disclosure (in this example, a polydimethylsiloxane (PDMS) microchamber array) was plasma treated for 2.5 minutes with a Plasma Etch PE-25 plasma cleaner to increase hydrophilicity. The array was then blocked in 3% BSA/PBS for 30 minutes. CD8+ T-cells were resuspended in 1 mL of PBS and stained with CellTrace Violet (1:1000, ThermoFisher) for 20 minutes. CD8+ T-cells were then washed 3× with supplemented X-Vivo 15 media and resuspended at a concentration of $2 \times 10^6$ cells/mL. Raji cells were taken from culture and resuspended in 1 mL of PBS and stained with Cell Trace CFSE (1:1000, ThermoFisher) for 20 minutes. Raji cells were then washed 3× with supplemented X-Vivo 15 media and resuspended at a concentration of $2 \times 10^6$ cells/mL. CD8+ T-cells and Raji cells were then combined at a 1:1 ratio to generate a cell suspension. Subsequently, 100 ng/mL of a bispecific antibody was added to this suspension. The cell suspension containing CD8+ T-cells and Raji cells was centrifuged for 10 minutes at 300×g and then resuspended before loading onto the array. Immediately before the assay, the array was rinsed with media and dried using compressed air. The array was then positioned on a glass slide and secured into a custom clamping system. Thirty microliters of the cell suspension was pipetted, chamber-by-chamber, onto the array. A surface (a glass side in this example) with the a repeated pattern of antibodies attached thereto was contacted to the array such that the repeated pattern of antibodies was facing the array and such that each repeat of the pattern aligned with a chamber of the array. The array and the surface (with the antibody pattern) enclosing the array were clamped tightly together in our custom clamping system. Cells were trapped in microchambers and imaged immediately after loading as described below. The microchamber assembly was placed in a standard 5% CO2, incubator at 37° C. for 16 hours. Following incubation, the surface with the antibody pattern was removed in a 1% BSA/PBS bath and rinsed with 1% BSA/PBS. Subsequently, 300 [EL of a biotin-labeled secondary antibody cocktail was introduced to the surface and incubated for 45 minutes. This cocktail contains detection antibodies at a concentration of 0.25 pg/mL each in 1:200 suspension of 1% BSA/PBS. Following this step, the surface was rinsed with 1% BSA, 300 [EL of a 1:100 solution of APC streptavidin (BioLegened, 405207) was added and the surface was incubated for 30 minutes. Following this incubation, the surface was washed with 1% BSA/PBS then washed in coplin jars PBS, 50% PBS/DI water, DI water, DI water sequentially for 3 minutes in a centrifuge set at 125 rpm. The surface was dried for 30 seconds in a Labnet slide spinner (C1303-T). The surface was analyzed using a GenePix microarray scanner as described below.

Microchamber Array Imaging. A Zeiss Axio Observer.Z1 fluorescent microscope with an automatic stage was used to acquire both bright field and fluorescent images of the array. Images of the entire array were taken with a Hamamatsu Orca-Flash4.0 LT Digital CMOS camera (C11440-42U) of a 54183 uM×24866 uM area corresponding to either 253 tiles (5× image) or 494 tiles (10× image). Using Zen2 Pro software, the tiles were stitched together with 0% overlap and were exported as TIFFs for analysis by our proprietary CytoSpeak software.

Imaging of Antibody-Patterned Surface. GenePix 4400A scanners (Molecular Devices) were used to obtain scanned fluorescent images of the antibody-patterned surfaces. Two color channels, 488 (blue, PMT 350, Power 90) and 635 (red, PMT 600, Power 90) were used to collect fluorescence signals using GenePix Pro software (Molecular Devices). The image was then exported as a TIFF before analysis using CytoSpeak software.

Example 3: Analysis of Interactions Between CAR T-Cells and Stimulation Beads CD19 Bead Design. $1 \times 10^8$ M450 Tosylactivated Dynabeads (ThermoFisher) (250 [EL of the M450 Tosylactivated Dynabeads) were washed 3× with PBS. Recombinant human CD19-Histidine (His) (Sino) was resuspeneded in dH20 at 1 µg/µL and incubated at room temperature for 30 minutes. Fifty microliters of CD19-His was then added to the beads and incubated at room temperature overnight, with rotation. The CD19-coated beads were then washed 3× with PBS. To inactivate the remaining tosyl groups on the beads, the beads were resuspended in 250 µL of 0.2M Tris with 0.1% BSA (pH 8.5) and incubated with rotation overnight at room temperature. The beads were then resuspended in PBS at a concentration of 4×10$^6$ beads/mL and stored at 4° C. until use.

CAR T-cell Stimulation. CAR-T cells were mixed with CD19-coated beads in a 1:4 ratio and plated at a concentration of 1×10$^6$ cells/mL in a 96-well plate. The plate was incubated for 6 hours at 37° C. and 5% CO2 before performing the assay.

Cell Culture. Target cells were cultured in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083) and 1× GlutaMAX supplement (ThermoFisher, 35050061). CAR T– cells were thawed and cultured overnight at a concentration of 1×10$^6$ cells/mL in X-Vivo 15 without Gentamicin or phenol red (Lonza, 04-744Q) supplemented with 1× GlutaMAX (ThermoFisher, 35050061), 1 mM sodium pyruvate (ThermoFisher, 11360-070), 1×MEM Vitamin Solution (Gibco; ThermoFisher, 11120-052), 20 mM HEPES (Gibco; ThermoFisher, 15630-080), 2% Human AB serum (Valley Biomedical, HP1022HI), 1× Penicillin-Streptomycin-Neomycin (Sigma-Aldrich, P4083) and 4 ng/mL recombinant human IL-2 (BioLegend, 589104). Immediately prior to use, dead cells were removed from culture using a Dead Cell Removal Kit (Miltenyi, 130-090-101) and LS Magnetic Column (Miltenyi, 130-042-401) or by using a standard Ficoll-Paque Plus (GE, 17-1440-02) dead cell removal protocol. If it is desired to separate the CD8+ from CD4+ cells in culture, CD8 microbeads (Miltenyi, 130-045-201) may be used for isolation according to the manufacturer's instructions following dead cell removal. Single-Cell Secretome Assay. Before performing the single cell assay, the array was plasma treated for 2.5 minutes with a Plasma Etch PE-25 plasma cleaner to increase hydrophilicity. The array was then blocked in 3% BSA/PBS for 30 minutes. Stimulated T-cells were collected, stained at 1:100 with an anti-human CD4 RPE antibody (ThermoFisher, MHCD0404) and an anti-human CD8a Alexa Fluor 647 antibody (BioLegend, 300918) and incubated at room temperature for 10 minutes. The stimulated T-cells were centrifuged at 300×g for 10 minutes and re-suspended in fresh media at a concentration of 2.5×10$^6$ cells/mL. Immediately before the assay, the array was rinsed with media and dried using compressed air. The array was then positioned on a glass slide and secured into a custom clamping system. Thirty microliters of the cell suspension was pipetted, chamber-by-chamber, onto the array. A surface (a glass side in this example) with the a repeated pattern of antibodies attached thereto was contacted to the array such that the repeated pattern of antibodies was facing the array and such that each repeat of the pattern aligned with a chamber of the array. The array and the surface (with the antibody pattern) enclosing the array were clamped tightly together in our custom clamping system. Cells were trapped in microchambers and imaged immediately after loading as described below. The microchamber assembly was placed in a standard 5% CO2, incubator at 37° C. for 16 hours. Following incubation, the surface with the antibody pattern was removed in a 1% BSA/PBS bath and rinsed with 1% BSA/PBS. Subsequently, 300 [IL of a biotin-labeled secondary antibody cocktail was introduced to the surface and incubated for 45 minutes. This cocktail contains detection antibodies at a concentration of 0.2511 g/mL each in 1:200 suspension of 1% BSA/PBS. Following this step, the surface was rinsed with 1% BSA, 300 [IL of a 1:100 solution of APC streptavidin (BioLegened, 405207) was added and the surface was incubated for 30 minutes. Following this incubation, the surface was washed with 1% BSA/PBS then washed in coplin jars PBS, 50% PBS/DI water, DI water, DI water sequentially for 3 minutes in a centrifuge set at 125 rpm. The surface was dried for 30 seconds in a Labnet slide spinner (C1303-T). The surface was analyzed using a GenePix microarray scanner as described below.

Microchamber Array Imaging. A Zeiss Axio Observer.Z1 fluorescent microscope with an automatic stage was used to acquire both bright field and fluorescent images of the array. Images of the entire array were taken with a Hamamatsu Orca-Flash4.0 LT Digital CMOS camera (Cl 1440-42U) of a 54183 uM×24866 uM area corresponding to either 253 tiles (5× image) or 494 tiles (10× image). Using Zen2 Pro software, the tiles were stitched together with 0% overlap and were exported as TIFFs for analysis by our proprietary CytoSpeak software.

Imaging of Antibody-Patterned Surface. GenePix 4400A scanners (Molecular Devices) were used to obtain scanned fluorescent images of the antibody-patterned surfaces. Two color channels, 488 (blue, PMT 350, Power 90) and 635 (red, PMT 600, Power 90) were used to collect fluorescence signals using GenePix Pro software (Molecular Devices). The image was then exported as a TIFF before analysis using CytoSpeak software.

Example 4: Analysis of Interactions Between CAR T-Cells and Target Cells

Target Cell Design. Target cells are generated by cloning full length cDNA (see list of target cDNAs below) into a pcDNA3.1 (+) vector (ThermoFisher, V79020) using the EcoRI and XhoI cut sites. The target plasmid is transfected into K562 cells (ATCC, CCL243) in a 24-well plate following the standard Lipofectamine 3000 (ThermoFisher) protocol. Stable pool lines are created by selecting transformants with 500 μg/mL Geneticin (ThermoFisher) for 3-4 weeks. Once stable pools are created, clonal lines are developed by serially diluting cells in a 96 well plate. Wells with a single cell are cultured and selected with Geneticin for 3-4 weeks, until a stable clonal line is developed. Clonal lines were frozen at a concentration of 1×10' cells/vial in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083), 1× GlutaMAX supplement (ThermoFisher, 35050061) and 10% DMSO. Target cDNAs include, but are not limited to, the following: Nerve Growth Factor Receptor (NGFR; Negative control cDNA), CD19, Epidermal Growth Factor Receptor (EGFR), Epidermal Growth Factor Receptor type III mutation (EGFRvIII; also referred to as de2-7 EGFR or AEGFR), Melanoma-associated antigen 3 (MAGE A3), NY-ESO-1 (also known as CTAG-1B; an immunogenic cancer antigen), Prostate Stem Cell Antigen (PSCA), Preferentially Expressed Antigen In Melanoma (PRAME), human epidermal growth factor receptor 2 (HER2), B-cell maturation antigen (BCMA; also known as CD296), carcinoembryonic antigen (CEA), Mucin 1 (MUC-1; also known as episialin, PEM, H23Ag, EMA, CA15-3, and MCA), Mucin 16 (MUC-16), and Mesothelin.

Cell Culture. Target cells were cultured in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083) and 1× GlutaMAX supplement (ThermoFisher, 35050061). CART– cells were thawed and cultured overnight at a concentration of $1\times10^6$ cells/mL in X-Vivo 15 without Gentamicin or phenol red (Lonza, 04-744Q) supplemented with 1× GlutaMAX (ThermoFisher, 35050061), 1 mM sodium pyruvate (ThermoFisher, 11360-070), 1×MEM Vitamin Solution (Gibco; ThermoFisher, 11120-052), 20 mM HEPES (Gibco; ThermoFisher, 15630-080), 2% Human AB serum (Valley Biomedical, HP1022HI), 1× Penicillin-Streptomycin-Neomycin (Sigma-Aldrich, P4083) and 4 ng/mL recombinant human IL-2 (BioLegend, 589104). Immediately prior to use, dead cells were removed from culture using a Dead Cell Removal Kit (Miltenyi, 130-090-101) and LS Magnetic Column (Miltenyi, 130-042-401) or by using a standard Ficoll-Paque Plus (GE, 17-1440-02) dead cell removal protocol. If it is desired to separate the CD8+ from CD4+ cells in culture, CD8 microbeads (Miltenyi, 130-045-201) may be used for isolation according to the manufacturer's instructions following dead cell removal.

CAR T-cell Stimulation. Target cells were stained for 20 minutes with CellTrace CF SE (ThermoFisher, C34554) and rinsed 3× with supplemented X-Vivo 15 media prior to use. Target cells (at a concentration of $1\times10^6$ cells/mL) and CAR T-cells (at a concentration of $1\times10^6$ cells/mL) were combined in a 1:1 ratio to generate a cell suspension. Two hundred microliters of the cell suspension containing the CAR T-cells and the target cells was plated per well into a 96-well plate and incubated at 37° C., 5% CO2 for 1-2 hours.

Single-Cell Secretome Assay. Before performing the single cell assay, the array was plasma treated for 2.5 minutes with a Plasma Etch PE-25 plasma cleaner to increase hydrophilicity. The array was then blocked in 3% BSA/PBS for 30 minutes. Stimulated T-cells were collected, stained at 1:100 with an anti-human CD4 RPE antibody (ThermoFisher, MHCD0404) and an anti-human CD8a Alexa Fluor 647 antibody (BioLegend, 300918) and incubated at room temperature for 10 minutes. The stimulated T-cells were centrifuged at 300×g for 10 minutes and re-suspended in fresh media at a concentration of $2.5\times10^6$ cells/mL. Immediately before the assay, the array was rinsed with media and dried using compressed air. The array was then positioned on a glass slide and secured into a custom clamping system. Thirty microliters of the cell suspension was pipetted, chamber-by-chamber, onto the array. A surface (a glass side in this example) with the a repeated pattern of antibodies attached thereto was contacted to the array such that the repeated pattern of antibodies was facing the array and such that each repeat of the pattern aligned with a chamber of the array. The array and the surface (with the antibody pattern) enclosing the array were clamped tightly together in our custom clamping system. Cells were trapped in microchambers and imaged immediately after loading as described below. The microchamber assembly was placed in a standard 5% CO2, incubator at 37° C. for 16 hours. Following incubation, the surface with the antibody pattern was removed in a 1% BSA/PBS bath and rinsed with 1% BSA/PBS. Subsequently, 300 [EL of a biotin-labeled secondary antibody cocktail was introduced to the surface and incubated for 45 minutes. This cocktail contains detection antibodies at a concentration of 0.25 [Eg/mL each in 1:200 suspension of 1% BSA/PBS. Following this step, the surface was rinsed with 1% BSA, 300 [EL of a 1:100 solution of APC streptavidin (BioLegened, 405207) was added and the surface was incubated for 30 minutes. Following this incubation, the surface was washed with 1% BSA/PBS then washed in coplin jars PBS, 50% PBS/DI water, DI water, DI water sequentially for 3 minutes in a centrifuge set at 125 rpm. The surface was dried for 30 seconds in a Labnet slide spinner (C1303-T). The surface was analyzed using a GenePix microarray scanner as described below.

Microchamber Array Imaging. A Zeiss Axio Observer.Z1 fluorescent microscope with an automatic stage was used to acquire both bright field and fluorescent images of the array. Images of the entire array were taken with a Hamamatsu Orca-Flash4.0 LT Digital CMOS camera (C11440-42U) of a 54183 uM×24866 uM area corresponding to either 253 tiles (5× image) or 494 tiles (10× image). Using Zen2 Pro software, the tiles were stitched together with 0% overlap and were exported as TIFFs for analysis by our proprietary CytoSpeak software.

Imaging of Antibody-Patterned Surface. GenePix 4400A scanners (Molecular Devices) were used to obtain scanned fluorescent images of the antibody-patterned surfaces. Two color channels, 488 (blue, PMT 350, Power 90) and 635 (red, PMT 600, Power 90) were used to collect fluorescence signals using GenePix Pro software (Molecular Devices). The image was then exported as a TIFF before analysis using CytoSpeak software.

Example 5: Analysis of Interactions Between CAR T-Cells and Target Cells with Target Cell Depletion Target Cell Design. Target cells are generated by cloning full length cDNA (see list of target cDNAs below) into a pcDNA3.1 (+) vector (ThermoFisher, V79020) using the EcoRI and XhoI cut sites. The target plasmid is transfected into K562 cells (ATCC, CCL243) in a 24-well plate following the standard Lipofectamine 3000 (ThermoFisher) protocol. Stable pool lines are created by selecting transformants with 500 µg/mL Geneticin (ThermoFisher) for 3-4 weeks. Once stable pools are created, clonal lines are developed by serially diluting cells in a 96 well plate. Wells with a single cell are cultured and selected with Geneticin for 3-4 weeks, until a stable clonal line is developed. Clonal lines were frozen at a concentration of $1\times10^7$ cells/vial in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083), 1× GlutaMAX supplement (ThermoFisher, 35050061) and 10% DMSO. Target cDNAs include, but are not limited to, the following: Nerve Growth Factor Receptor (NGFR; Negative control cDNA), CD19, Epidermal Growth Factor Receptor (EGFR), Epidermal Growth Factor Receptor type III mutation (EGFRvIII; also referred to as de2-7 EGFR or AEGFR), Melanoma-associated antigen 3 (MAGE A3), NY-ESO-1 (also known as CTAG-1B; an immunogenic cancer antigen), Prostate Stem Cell Antigen (PSCA), Preferentially Expressed Antigen In Melanoma (PRAME), human epidermal growth factor receptor 2 (HER2), B-cell maturation antigen (BCMA; also known as CD296), carcinoembryonic antigen (CEA), Mucin 1 (MUC-1; also known as episialin, PEM, H23Ag, EMA, CA15-3, and MCA), Mucin 16 (MUC-16), and Mesothelin.

Cell Culture. Target cells were cultured in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083) and 1× GlutaMAX supplement (ThermoFisher, 35050061). CAR T– cells were thawed and cultured overnight at a concentration of $1\times10^6$ cells/mL in X-Vivo 15 without Gentamicin or phenol red (Lonza, 04-744Q) supplemented with 1× GlutaMAX (ThermoFisher, 35050061), 1 mM sodium pyruvate (ThermoFisher, 11360-070), 1×MEM Vitamin Solution (Gibco; ThermoFisher, 11120-052), 20 mM HEPES (Gibco; ThermoFisher, 15630-080), 2% Human AB serum (Valley Biomedical, HP1022HI), 1× Penicillin-Streptomycin-Neomycin (Sigma-Aldrich, P4083) and 4 ng/mL recombinant human IL-2 (BioLegend, 589104). Immediately prior to use, dead cells were removed from culture using a Dead Cell Removal Kit (Miltenyi, 130-090-101) and LS Magnetic Column (Miltenyi, 130-042-401) or by using a standard Ficoll-Paque Plus (GE, 17-1440-02) dead cell removal protocol. If it is desired to separate the CD8+ from CD4+ cells in culture, CD8 microbeads (Miltenyi, 130-045-201) may be used for isolation according to the manufacturer's instructions following dead cell removal.

CAR T-cell Stimulation. CAR T-cells (at a concentration of $1\times10^6$ cells/mL) and target cells (at a concentration of $1\times10^6$ cells/mL) are mixed in a ratio of 1:1 to generate a cell suspension. Two hundred microliters of the cell suspension is plated per well of a 96-well plate. The plate is then incubated overnight (in this example is approximately 20 hours) in an incubator at 37° C. with 5% CO2.

Target Cell Depletion. After an overnight stimulation, the cell suspension containing CAR T-cells and target cells is removed from the wells and centrifuged for 10 minutes at 300×g. The supernatant is then removed and the cells are resuspended in a conjugated bead solution. The conjugated bead solution contains M280 Dynabeads conjugated to an antibody against the target receptor. The beads of the conjugated bead solution are designed to remove all of the target cells from the solution. This conjugated bead solution containing the CAR T-cells and the target cells is incubated, with gentle mixing, at room temperature for 10 minutes. After the incubation, the solution containing the CAR T-cells and the target cells is brought up to a total volume of 1 mL with PBS and transferred to a 5 mL round bottom polypropylene falcon tube (Corning, 352063). The tube is then placed in an EasySep Magnet (StemCell Technologies, 18000) for 2 minutes before decanting the solution of CAR T-cells into a clean tube. The beads are washed with media and decanted 2× before centrifuging the CAR T-cells and resuspending the target cell depleted CAR-T cells for use in the assay.

Single-Cell Secretome Assay. Before performing the single cell assay, the array was plasma treated for 2.5 minutes with a Plasma Etch PE-25 plasma cleaner to increase hydrophilicity. The array was then blocked in 3% BSA/PBS for 30 minutes. Stimulated T-cells were collected, stained at 1:100 with an anti-human CD4 RPE antibody (ThermoFisher, MEICD0404) and an anti-human CD8a Alexa Fluor 647 antibody (BioLegend, 300918) and incubated at room temperature for 10 minutes. The stimulated T-cells were centrifuged at 300×g for 10 minutes and re-suspended in fresh media at a concentration of $2.5\times10^6$ cells/mL. Immediately before the assay, the array was rinsed with media and dried using compressed air. The array was then positioned on a glass slide and secured into a custom clamping system. Thirty microliters of the cell suspension was pipetted, chamber-by-chamber, onto the array. A surface (a glass side in this example) with the a repeated pattern of antibodies attached thereto was contacted to the array such that the repeated pattern of antibodies was facing the array and such that each repeat of the pattern aligned with a chamber of the array. The array and the surface (with the antibody pattern) enclosing the array were clamped tightly together in our custom clamping system. Cells were trapped in microchambers and imaged immediately after loading as described below. The microchamber assembly was placed in a standard 5% CO2, incubator at 37° C. for 16 hours. Following incubation, the surface with the antibody pattern was removed in a 1% BSA/PBS bath and rinsed with 1% BSA/PBS. Subsequently, 300 [EL of a biotin-labeled secondary antibody cocktail was introduced to the surface and incubated for 45 minutes. This cocktail contains detection antibodies at a concentration of 0.25 [Eg/mL each in a 1:200 suspension of 1% BSA/PBS. Following this step, the surface was rinsed with 1% BSA, 300 [EL of a 1:100 solution of APC streptavidin (BioLegened, 405207) was added and the surface was incubated for 30 minutes. Following this incubation, the surface was washed with 1% BSA/PBS then washed in coplin jars PBS, 50% PBS/DI water, DI water, DI water sequentially for 3 minutes in a centrifuge set at 125 rpm. The surface was dried for 30 seconds in a Labnet slide spinner (C1303-T). The surface was analyzed using a GenePix microarray scanner as described below.

Microchamber Array Imaging. A Zeiss Axio Observer.Z1 fluorescent microscope with an automatic stage was used to acquire both bright field and fluorescent images of the array. Images of the entire array were taken with a Hamamatsu Orca-Flash4.0 LT Digital CMOS camera (Cl 1440-42U) of a 54183 uM×24866 uM area corresponding to either 253 tiles (5× image) or 494 tiles (10× image). Using Zen2 Pro software, the tiles were stitched together with 0% overlap and were exported as TIFFs for analysis by our proprietary CytoSpeak software.

Imaging of Antibody-Patterned Surface. GenePix 4400A scanners (Molecular Devices) were used to obtain scanned fluorescent images of the antibody-patterned surfaces. Two color channels, 488 (blue, PMT 350, Power 90) and 635 (red, PMT 600, Power 90) were used to collect fluorescence signals using GenePix Pro software (Molecular Devices). The image was then exported as a TIFF before analysis using CytoSpeak software.

Example 6: Fluorescent Cytotoxicity Analysis of Target/Effector Interaction

This method can be applied to any of the target/effector (subject) cell types of the disclosure with the addition of the following step to the Single-Cell Secretome Assay Protocol. If fluorescent tracking of cytotoxicity is desired, 1 [iL/mL of SYTOX orange (ThermoFisher) may be added to the cell suspension containing the target cells and effector (subject) cells immediately prior to loading the cell suspension onto the array.

Example 7: Assessing Polyfunctionality in CAR-Expressing Anti-Tumor T-Cells

To evaluate engineered T cells for an immunotherapy or to evaluate endogenous T cells reactivated to battle cancer or infection, a T cell's functional status is largely determined by a spectrum of secreted effector function proteins (e.g., cytokines). In a protective immune response, the 'quality' of an immune cell correlates to the extent of polyfunctionality (the ability of a T cell to co-secrete multiple effector proteins). While these anti-tumor cytolytic, chemoattractive cytokines produce an effective response, these poly-functional cell subsets must not also secrete immuno-toxic inflammatory or regulatory cytokines (up to 15) prevalent in NK or CAR-T cells.

The following provides one method for determining whether a stimulated CAR-expressing anti-tumor T cell responds in a therapeutically effective and safe manner before administering the cell or substantially similar cell of a population of CAR-expressing anti-tumor T-cells to a patient as a therapeutic.

Target Cell Design. Target cells are generated by cloning full length cDNA (see list of target cDNAs below) into a pcDNA3.1 (+) vector (ThermoFisher, V79020) using the EcoRI and XhoI cut sites. The target plasmid is transfected into K562 cells (ATCC, CCL243) in a 24-well plate following the standard Lipofectamine 3000 (ThermoFisher) protocol. Stable pool lines are created by selecting transformants with 500 μg/mL Geneticin (ThermoFisher) for 3-4 weeks. Once stable pools are created, clonal lines are developed by serially diluting cells in a 96 well plate. Wells with a single cell are cultured and selected with Geneticin for 3-4 weeks, until a stable clonal line is developed. Clonal lines were frozen at a concentration of $1 \times 10^7$ cells/vial in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083), 1× GlutaMAX supplement (ThermoFisher, 35050061) and 10% DMSO. Target cDNAs include, but are not limited to, the following: Nerve Growth Factor Receptor (NGFR; Negative control cDNA), CD19, Epidermal Growth Factor Receptor (EGFR), Epidermal Growth Factor Receptor type III mutation (EGFRvIII; also referred to as de2-7 EGFR or AEGFR), Melanoma-associated antigen 3 (MAGE A3), NY-ESO-1 (also known as CTAG-1B; an immunogenic cancer antigen), Prostate Stem Cell Antigen (PSCA), Preferentially Expressed Antigen In Melanoma (PRAME), human epidermal growth factor receptor 2 (HER2), B-cell maturation antigen (BCMA; also known as CD296), carcinoembryonic antigen (CEA), Mucin 1 (MUC-1; also known as episialin, PEM, H23Ag, EMA, CA15-3, and MCA), Mucin 16 (MUC-16), and Mesothelin.

Cell Culture. Target cells were cultured in Corning™ Cellgro™ RPMI 1640 Medium (Mod.) 1× with L-Glutamine (Corning; ThermoFisher MT10040CV) supplemented with 10% FBS (Sigma-Aldrich, F2442), 1× Penicillin-Streptomycin-Neomycin (Sigma-Aldrich, P4083) and 1× GlutaMAX supplement (ThermoFisher, 35050061). CAR T– cells were thawed and cultured overnight at a concentration of $1 \times 10^6$ cells/mL in X-Vivo 15 without Gentamicin or phenol red (Lonza, 04-744Q) supplemented with 1× GlutaMAX (ThermoFisher, 35050061), 1 mM sodium pyruvate (ThermoFisher, 11360-070), 1×MEM Vitamin Solution (Gibco; ThermoFisher, 11120-052), 20 mM HEPES (Gibco; ThermoFisher, 15630-080), 2% Human AB serum (Valley Biomedical, HP1022HI), 1× Penicillin-Streptomycin-Neomycin (Sigma-Aldrich, P4083) and 4 ng/mL recombinant human IL-2 (BioLegend, 589104). Immediately prior to use, dead cells were removed from culture using a Dead Cell Removal Kit (Miltenyi, 130-090-101) and LS Magnetic Column (Miltenyi, 130-042-401) or by using a standard Ficoll-Paque Plus (GE, 17-1440-02) dead cell removal protocol. If it is desired to separate the CD8+ from CD4+ cells in culture, CD8 microbeads (Miltenyi, 130-045-201) may be used for isolation according to the manufacturer's instructions following dead cell removal.

CAR T-cell Stimulation. Target cells were stained for 20 minutes with CellTrace CFSE (ThermoFisher, C34554) and rinsed 3× with supplemented X-Vivo 15 media prior to use. Target cells (at a concentration of $1 \times 10^6$ cells/mL) and CAR T-cells (at a concentration of $1 \times 10^6$ cells/mL) were combined in a 1:1 ratio to generate a cell suspension. Two hundred microliters of the cell suspension containing the CAR T-cells and the target cells was plated per well into a 96-well plate and incubated at 37° C., 5% CO2 for 1-2 hours.

Single-Cell Secretome Assay. Before performing the single cell assay, the array was plasma treated for 2.5 minutes with a Plasma Etch PE-25 plasma cleaner to increase hydrophilicity. The array was then blocked in 3% BSA/PBS for 30 minutes. Stimulated T-cells were collected, stained at 1:100 with an anti-human CD4 RPE antibody (ThermoFisher, MHCD0404) and an anti-human CD8a Alexa Fluor 647 antibody (BioLegend, 300918) and incubated at room temperature for 10 minutes. The stimulated T-cells were centrifuged at 300×g for 10 minutes and re-suspended in fresh media at a concentration of $2.5 \times 10^6$ cells/mL. Immediately before the assay, the array was rinsed with media and dried using compressed air. The array was then positioned on a glass slide and secured into a custom clamping system. Thirty microliters of the cell suspension was pipetted, chamber-by-chamber, onto the array. A surface (a glass side in this example) with the a repeated pattern of antibodies attached thereto was contacted to the array such that the repeated pattern of antibodies was facing the array and such that each repeat of the pattern aligned with a chamber of the array. The array and the surface (with the antibody pattern) enclosing the array were clamped tightly together in our custom clamping system. Cells were trapped in microchambers and imaged immediately after loading as described below. The microchamber assembly was placed in a standard 5% CO2, incubator at 37° C. for 16 hours. Following incubation, the surface with the antibody pattern was removed in a 1% BSA/PBS bath and rinsed with 1% BSA/PBS. Subsequently, 300 [EL of a biotin-labeled secondary antibody cocktail was introduced to the surface and incubated for 45 minutes. This cocktail contains detection antibodies at a concentration of 0.25 [Eg/mL each in 1:200 suspension of 1% BSA/PBS. Following this step, the surface was rinsed with 1% BSA, 300 [EL of a 1:100 solution of APC streptavidin (BioLegened, 405207) was added and the surface was incubated for 30 minutes. Following this incubation, the surface was washed with 1% BSA/PBS then washed in coplin jars PBS, 50% PBS/DI water, DI water, DI water sequentially for 3 minutes in a centrifuge set at 125 rpm. The surface was dried for 30 seconds in a Labnet slide spinner (Cl 303-T). The surface was analyzed using a GenePix microarray scanner as described below.

Microchamber Array Imaging. A Zeiss Axio Observer.Z1 fluorescent microscope with an automatic stage was used to acquire both bright field and fluorescent images of the array. Images of the entire array were taken with a Hamamatsu Orca-Flash4.0 LT Digital CMOS camera (C11440-42U) of a 54183 uM×24866 uM area corresponding to either 253 tiles (5× image) or 494 tiles (10× image). Using Zen2 Pro software, the tiles were stitched together with 0% overlap and were exported as TIFFs for analysis by our proprietary CytoSpeak software.

Imaging of Antibody-Patterned Surface. GenePix 4400A scanners (Molecular Devices) were used to obtain scanned fluorescent images of the antibody-patterned surfaces. Two color channels, 488 (blue, PMT 350, Power 90) and 635 (red, PMT 600, Power 90) were used to collect fluorescence signals using GenePix Pro software (Molecular Devices). The image was then exported as a TIFF before analysis using CytoSpeak software.

Analysis of polyfunctionality: The absolute and relative contributions of each cytokine in the secretome of the control and target-cell stimulated CAR T-cells were measured. FIGS. 10 and 11 demonstrate on a single-cell basis the Polyfunctional Strength Index (PSI) contributions of each detected cytokine in the secretome. As shown in FIG. 11, panels E and F, when a population of cells are detected individually, but analyzed as a population, a percentage of cells in the given population that express any one cytokine above a threshold level may be determined. The cytokines used in this plot may include those cytokines that indicate a risk of the CAR-T cell inducing a deleterious or unwanted reaction in vivo and the threshold may be raised and lowered according to what is considered safe and tolerable. Using this method, any population of cells intended for administration in vivo as a cell therapy may be tested in vitro to reveal potential harmful reactions before the cell population can negatively impact a patient.

Figure 11A:
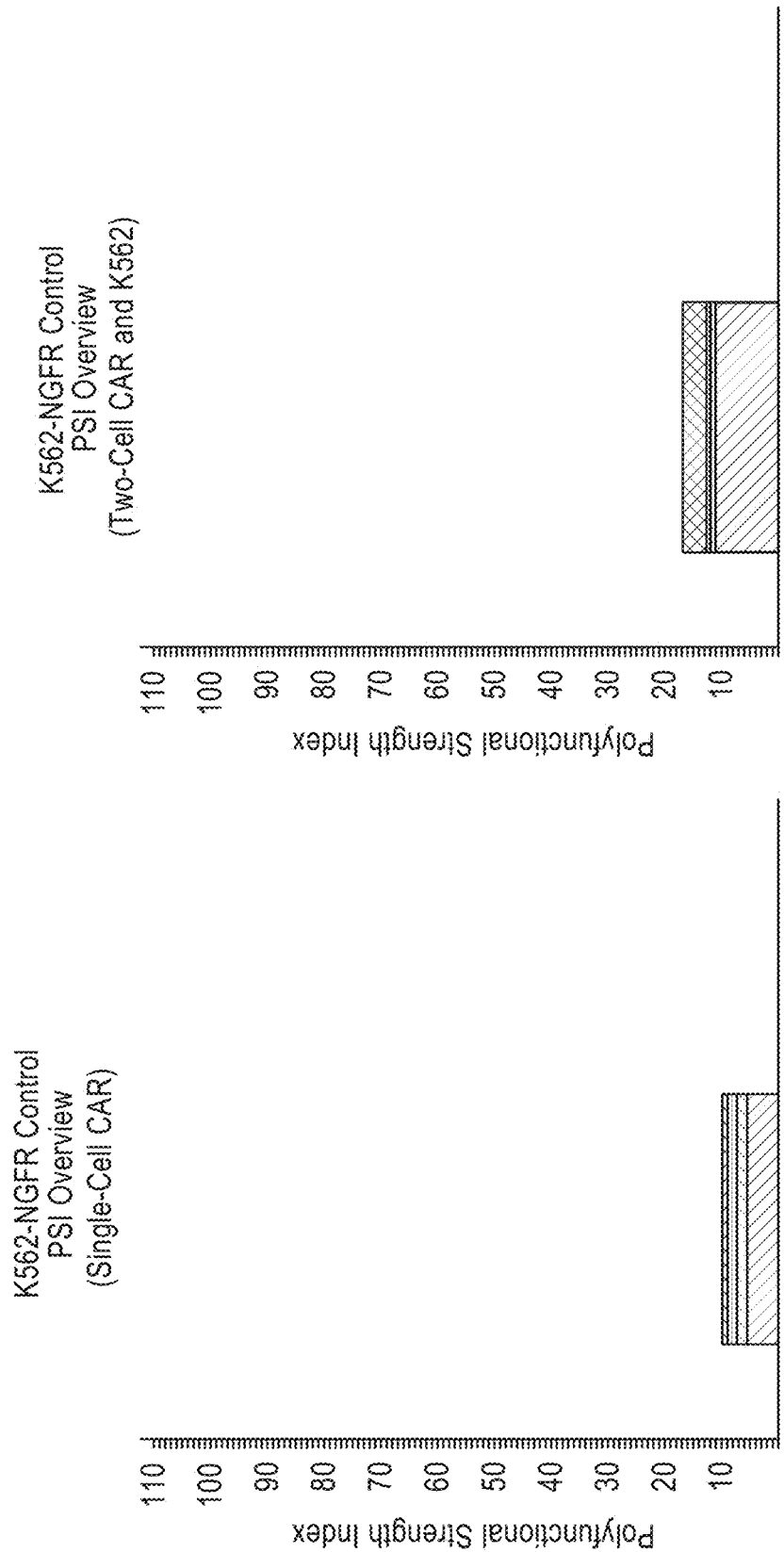
Figure 11B:
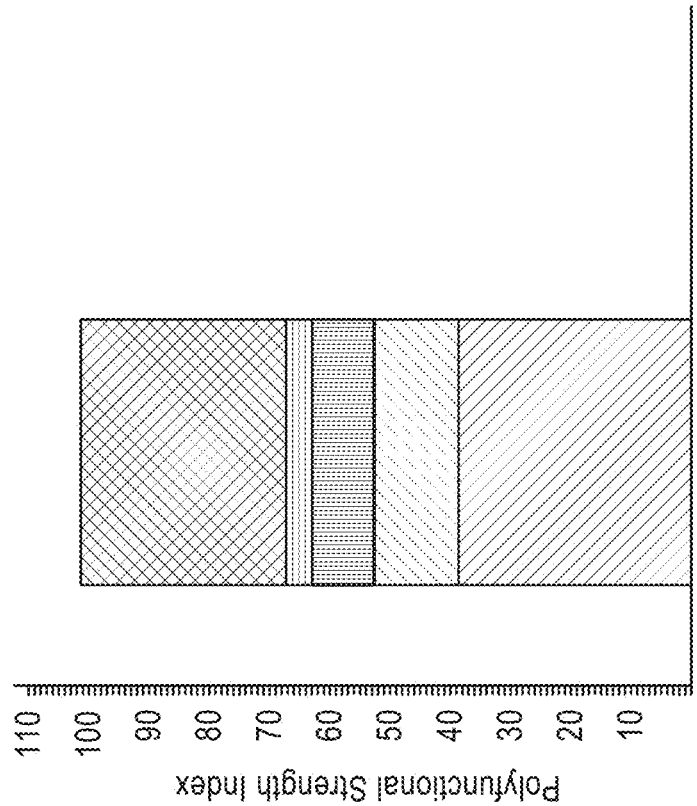
Figure 11B:
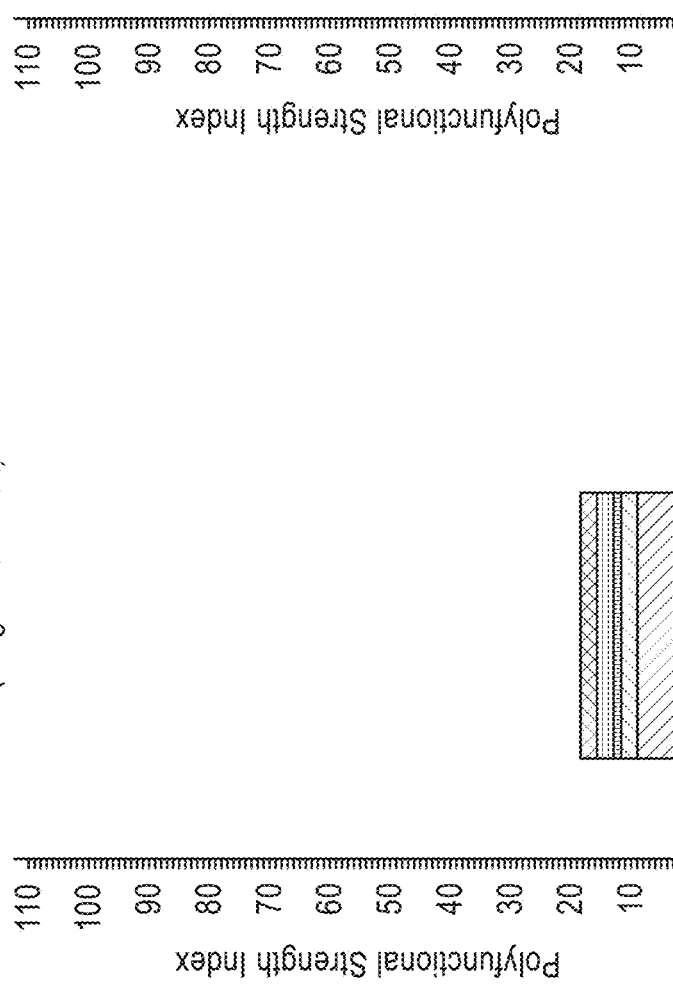

The polyfunctional strength index (PSI) is a metric that factors in the polyfunctionality of cells in a sample, and the signal intensity of the cytokines secreted by each cell. It is found by multiplying the percentage of polyfunctional cells of a sample (single cells secreting two or more cytokines), by the average signal intensity of these cytokines. This PSI is shown on the left of FIGS. 10A and 10B, as well as FIGS. 11A and 11B. For example, FIG. 10B demonstrates that the polyfunctional strength is roughly 2× higher in the CD19 stimulated sample, relative to the control PSI shown in FIG. 10A. FIG. 11B demonstrates that the stimulated cells have a polyfunctional strength roughly 5× higher than the control cells.

As seen in the bar graphs of FIGS. 10 and 11, the polyfunctional strength can be further broken down into defined cytokine groups (see the key shown in FIG. 8E), illustrating the impact of particular groups of cytokines on the sample's polyfunctionality. In the left graph of FIG. 10B, for example, effector cytokines are major drivers of the polyfunctionality, as they account for about 75% of the total PSI. The corresponding graph on the right shows the contribution of each individual cytokine to the overall PSI. In this case, Granzyme B is the major driver of the sample's polyfunctionality.

Figure 11C:
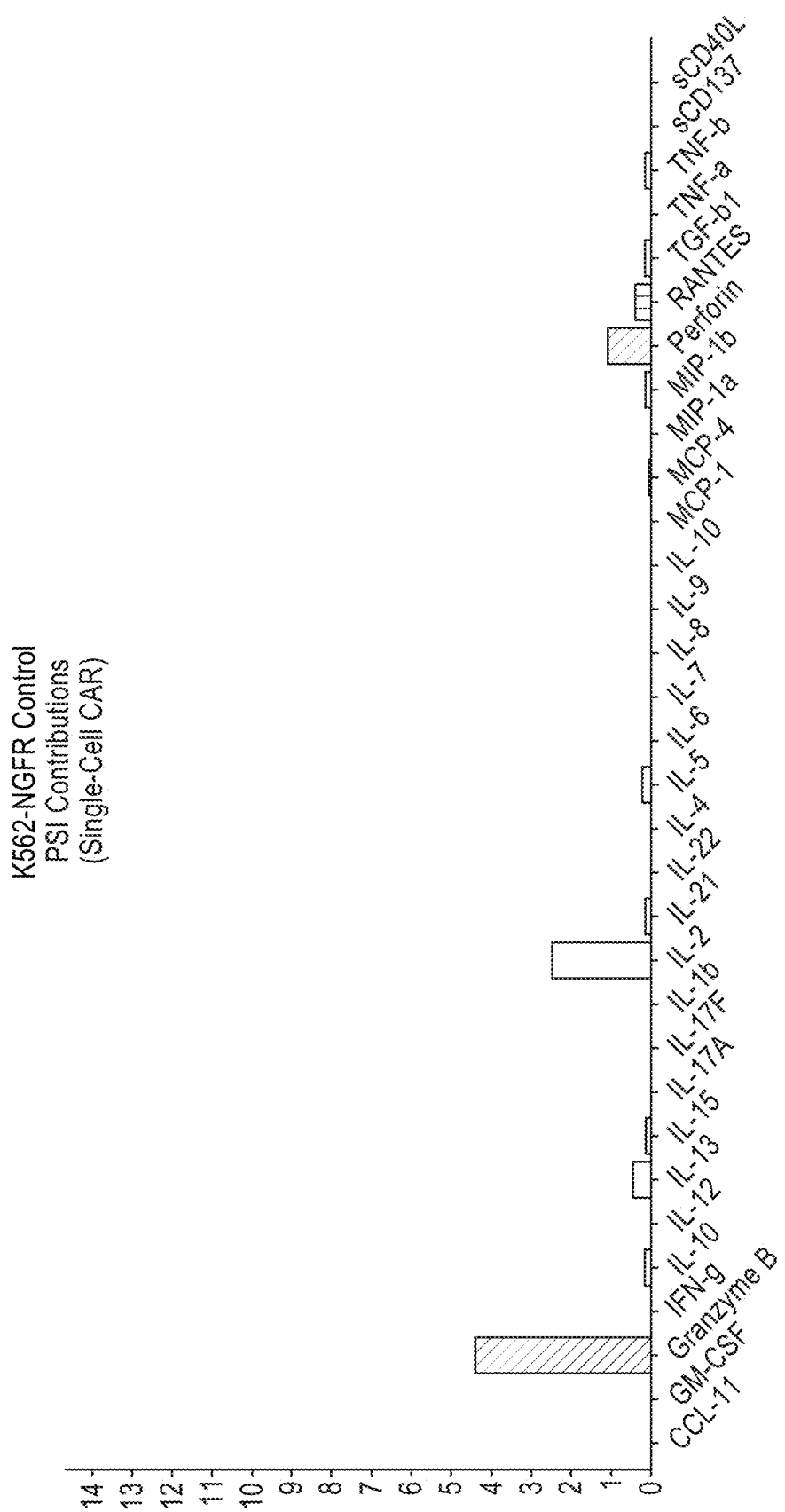
Figure 11C:
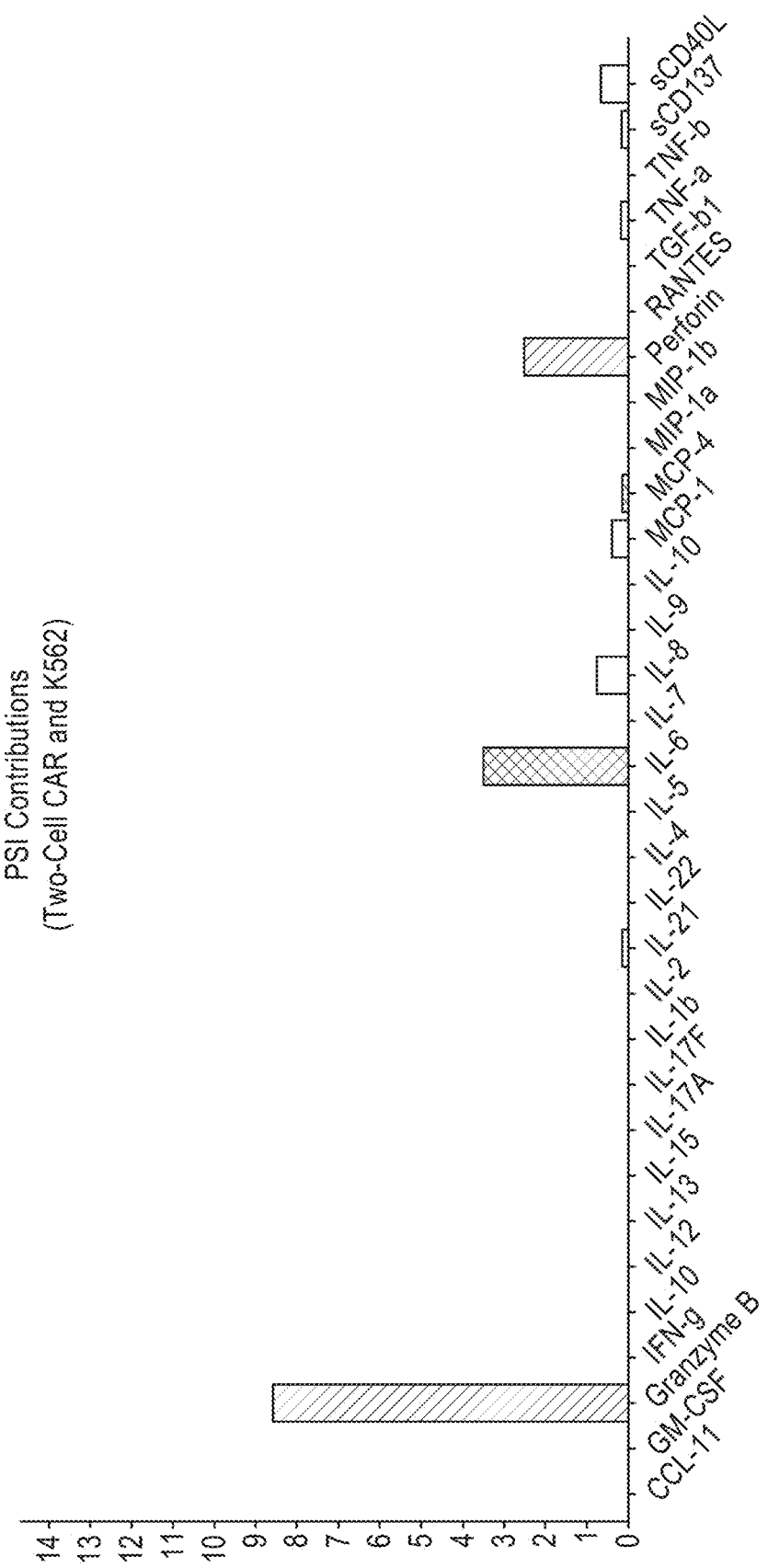
Figure 11D:
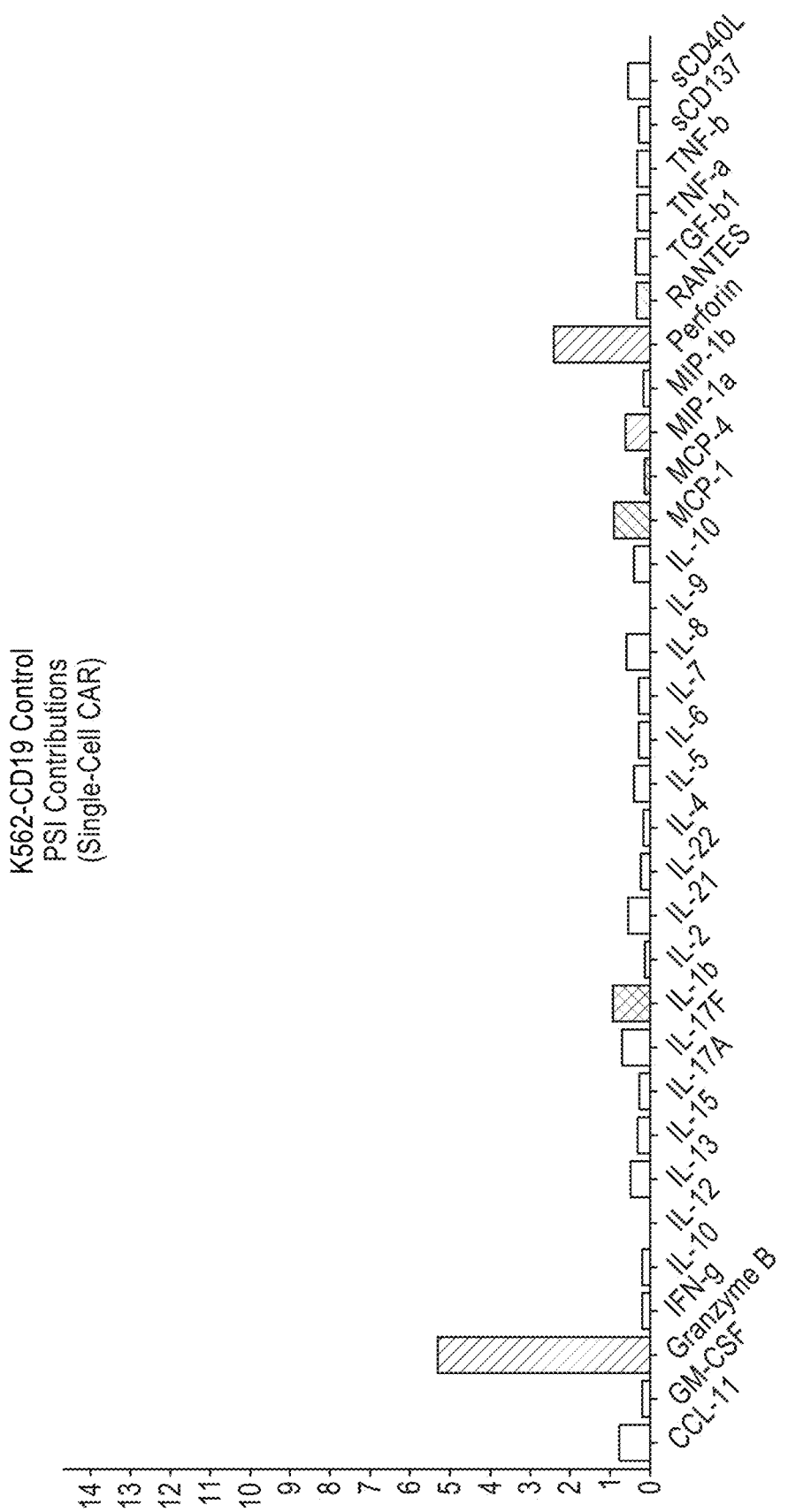
Figure 11D:
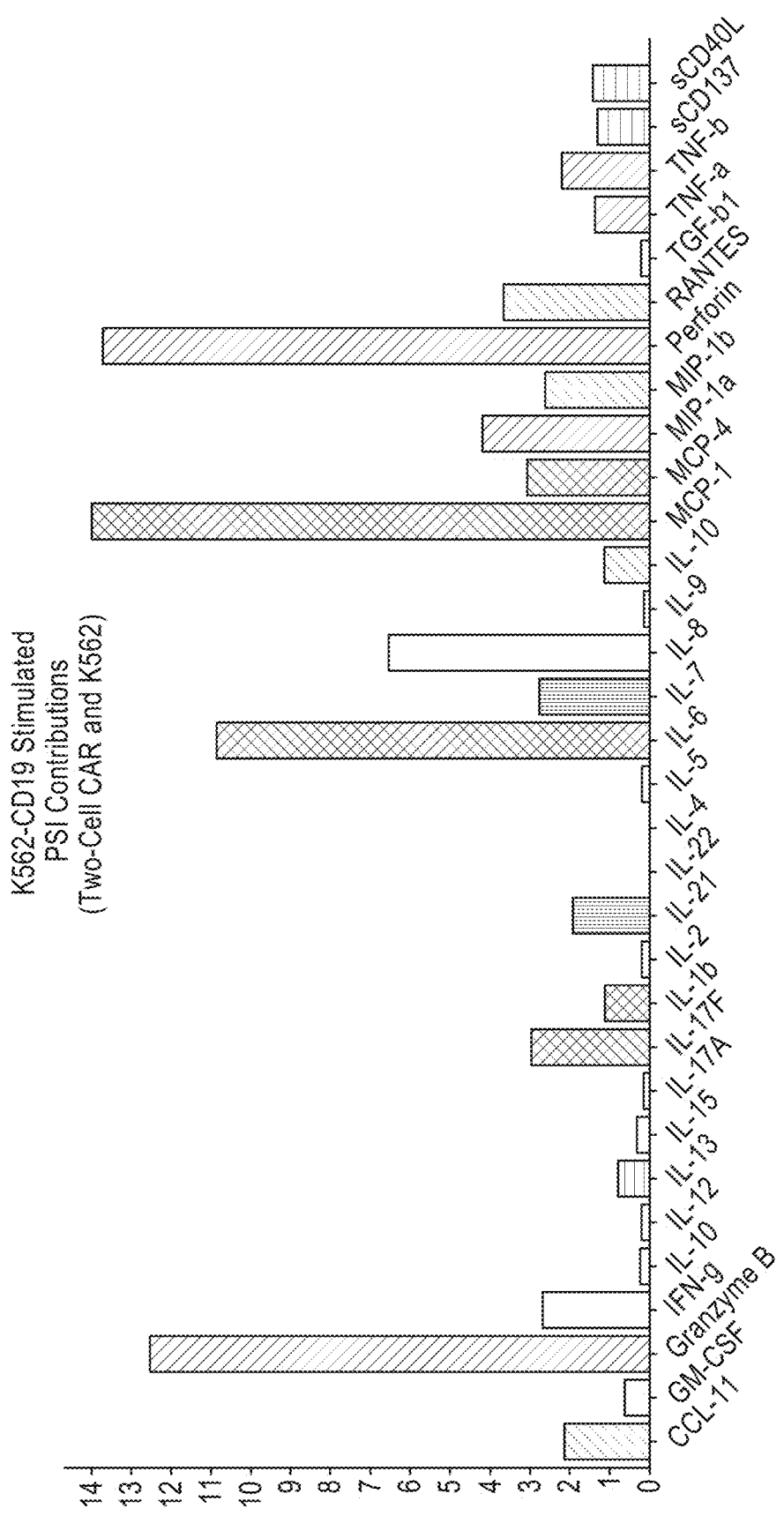
Figure 11E:
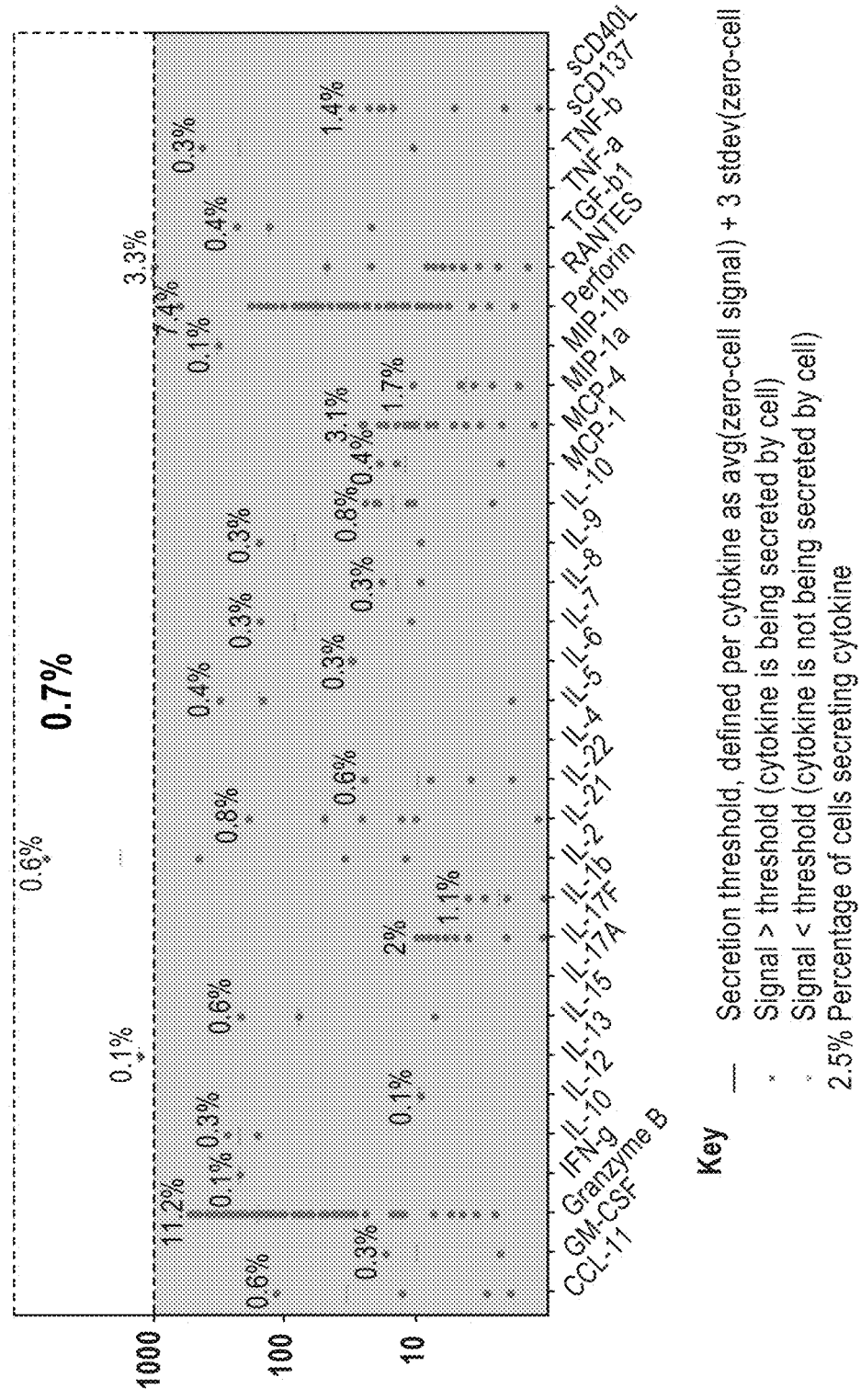
Figure 11E:
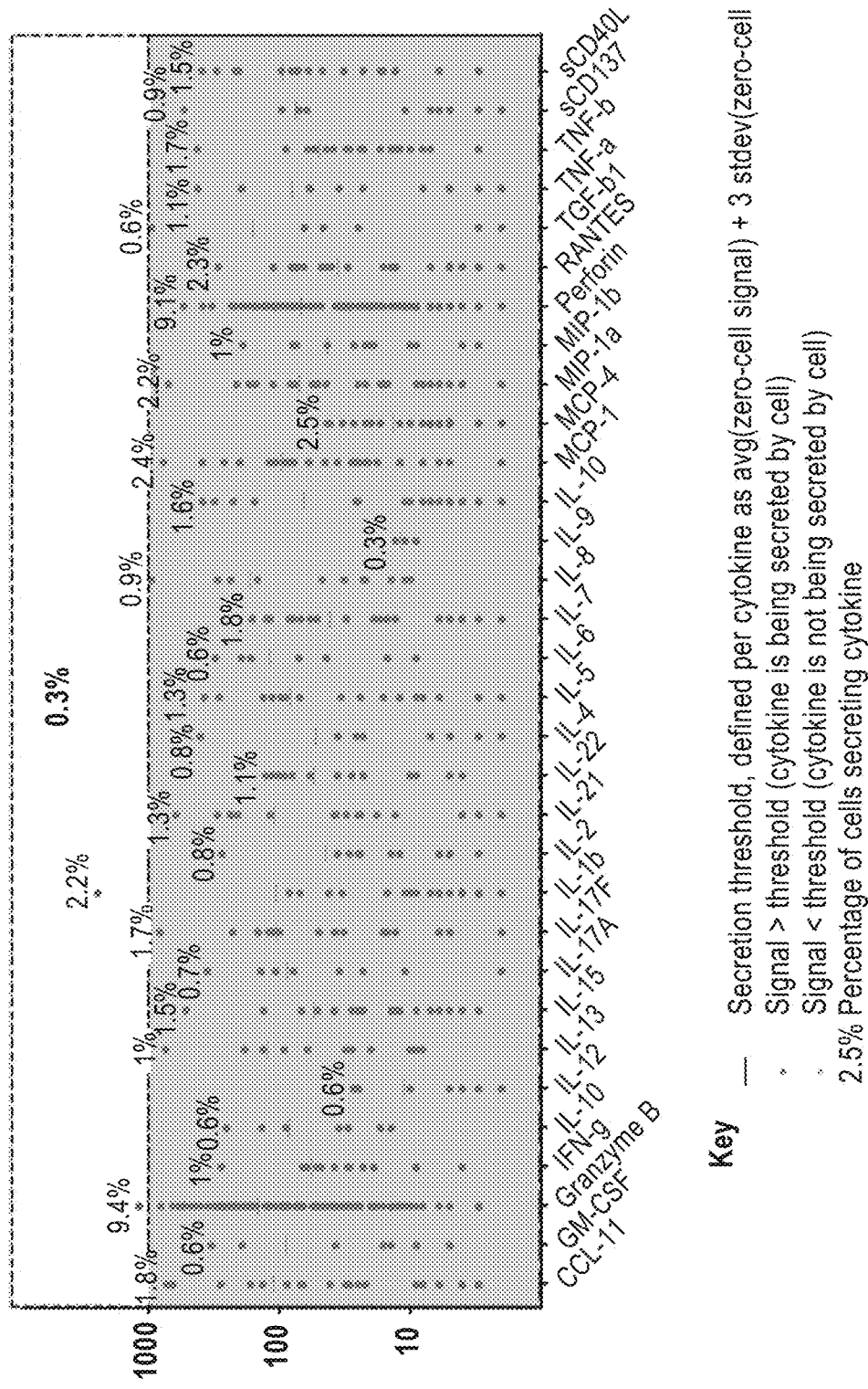
Figure 11F:
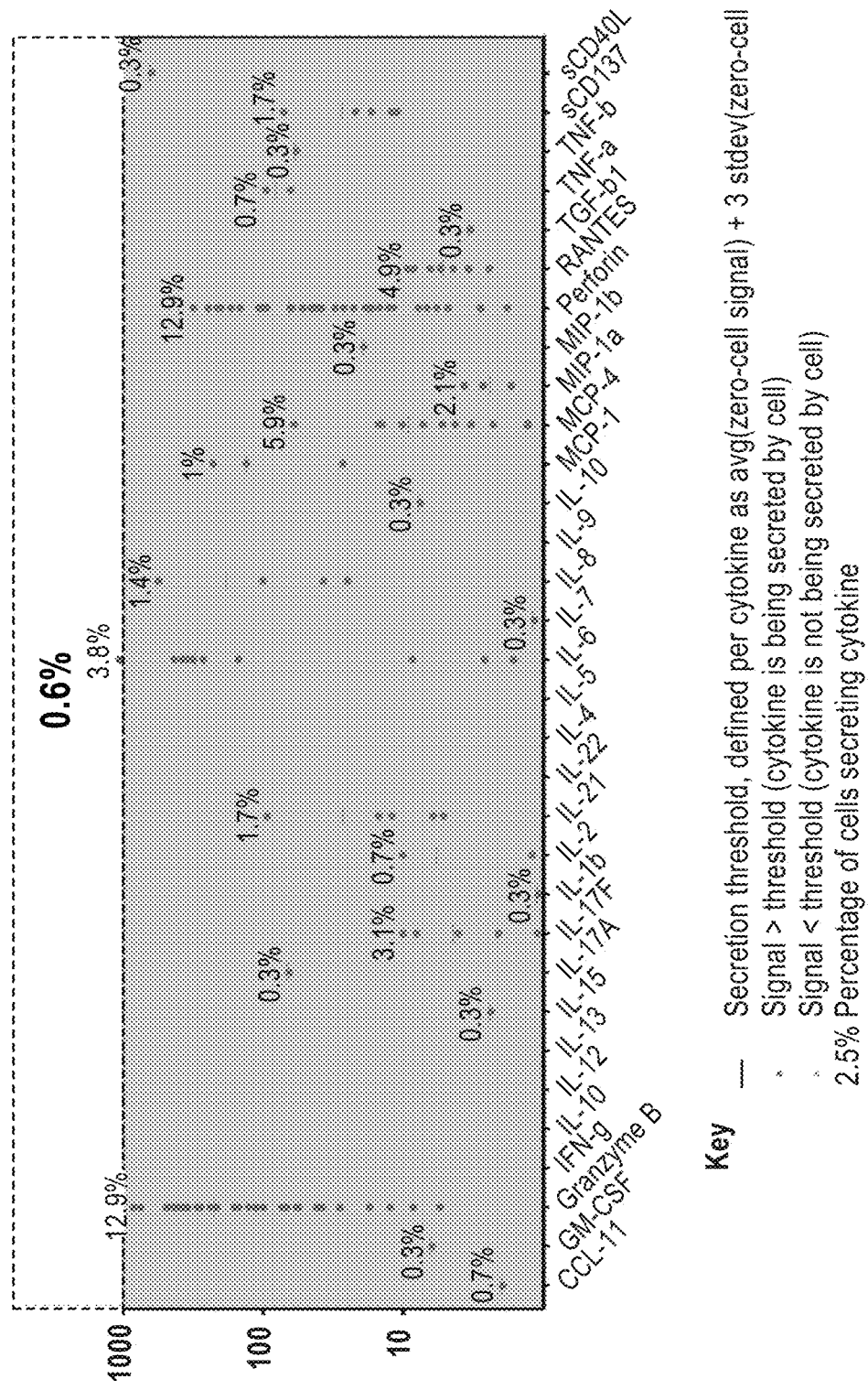
Figure 11F:
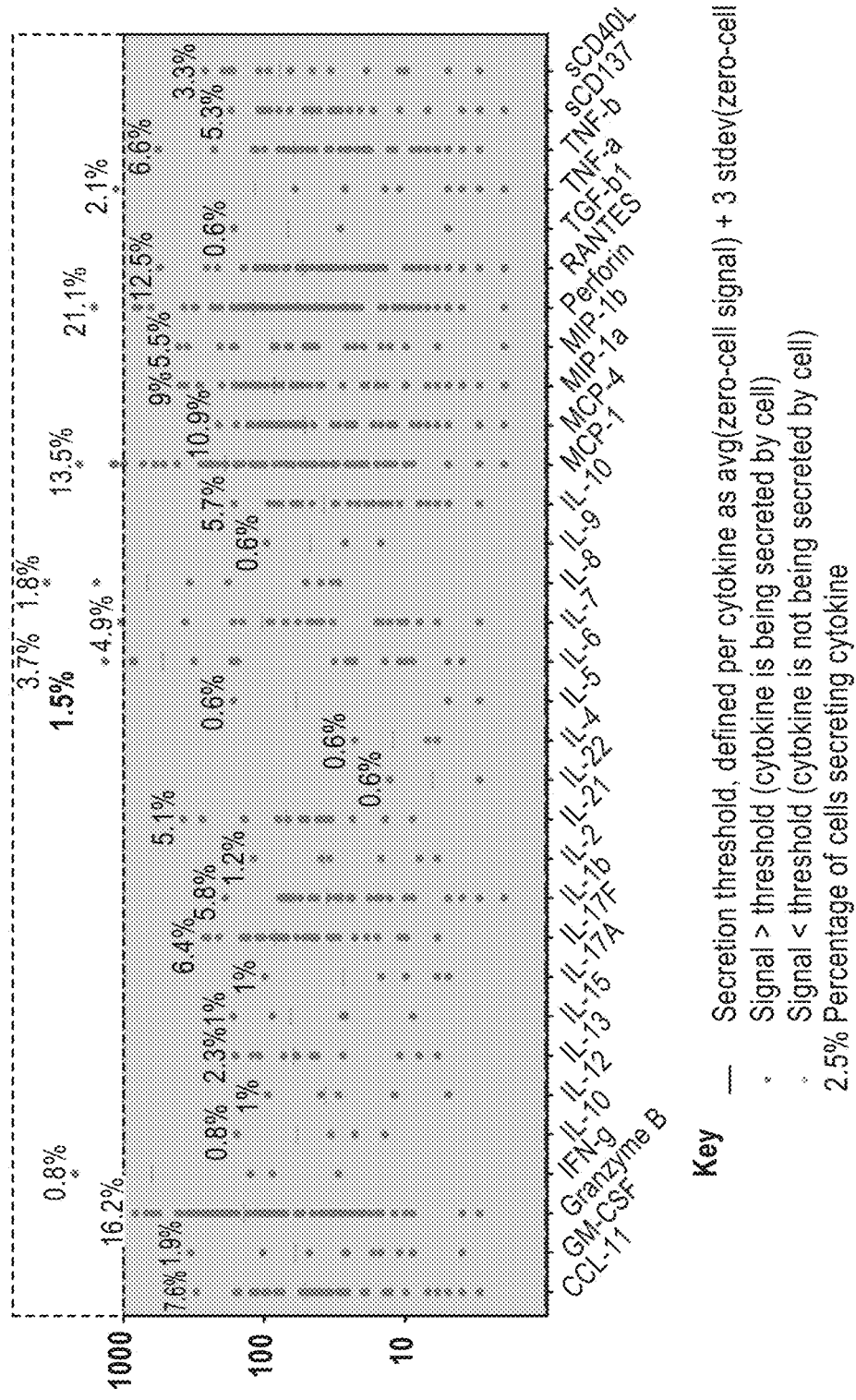
Figure 12A:
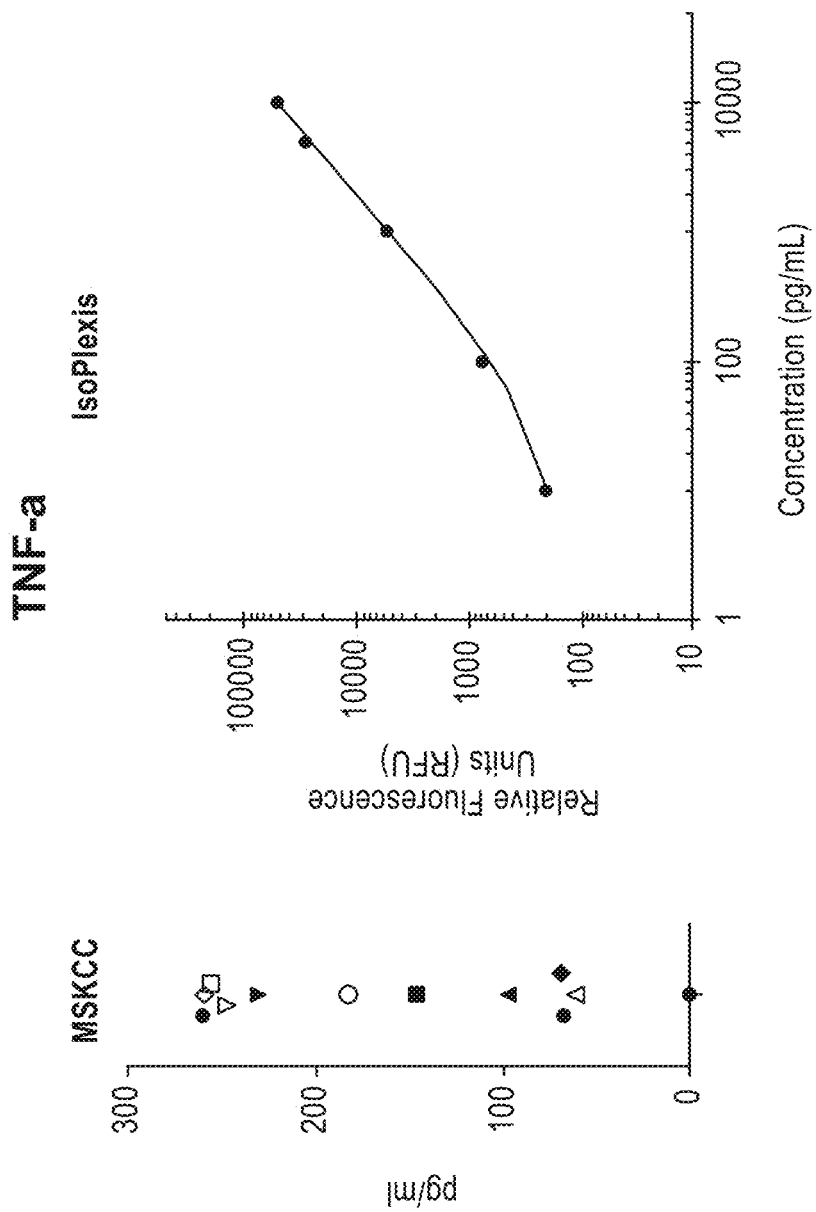
Figure 12B:
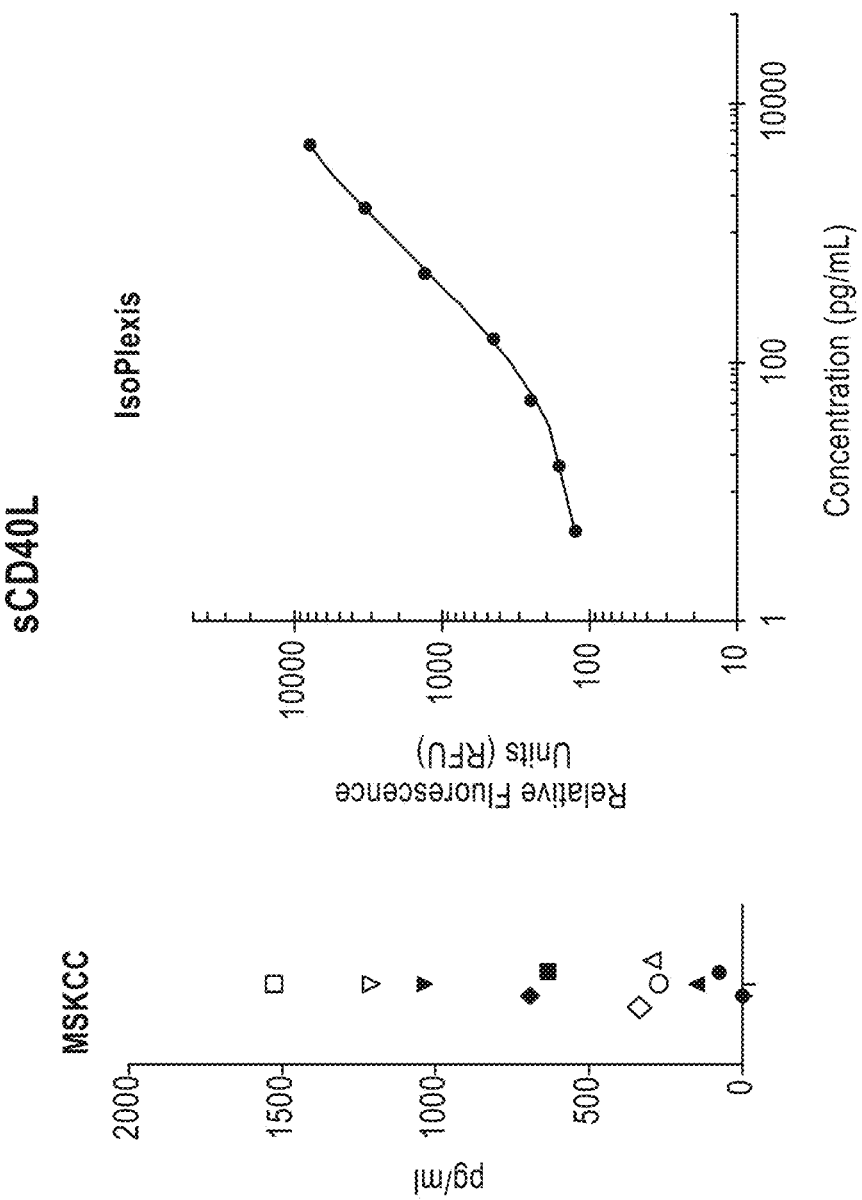
Figure 12D:
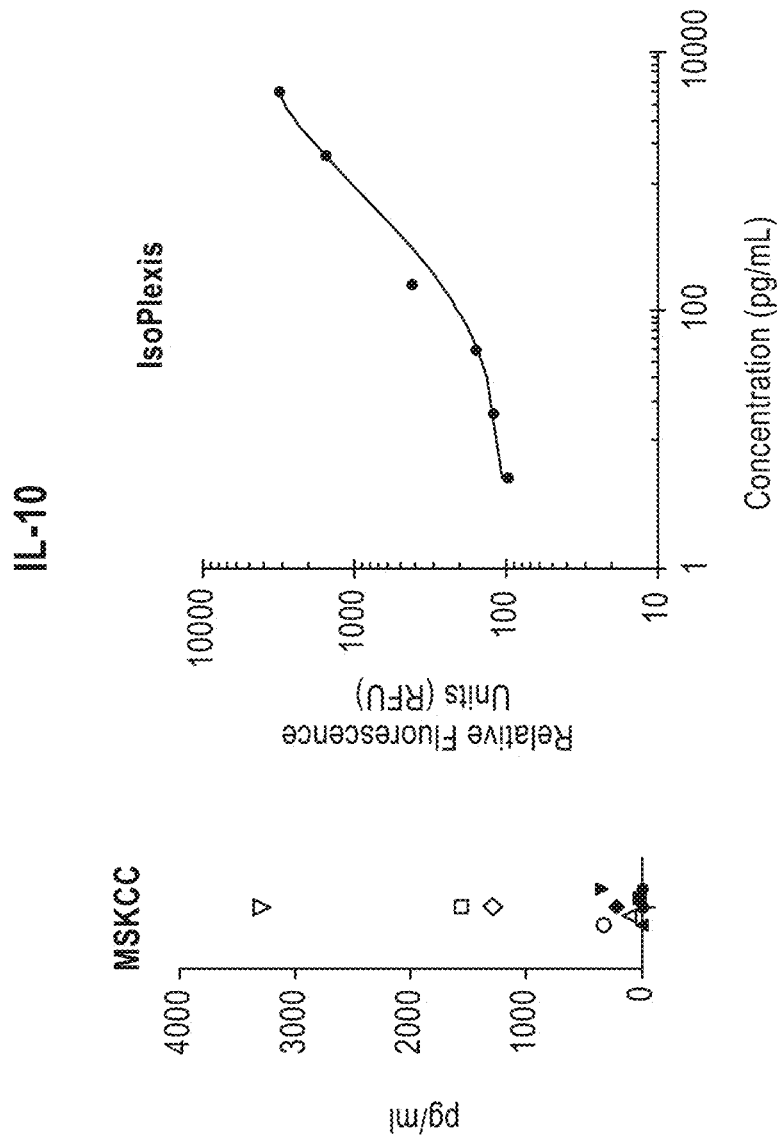
Figure 12E:
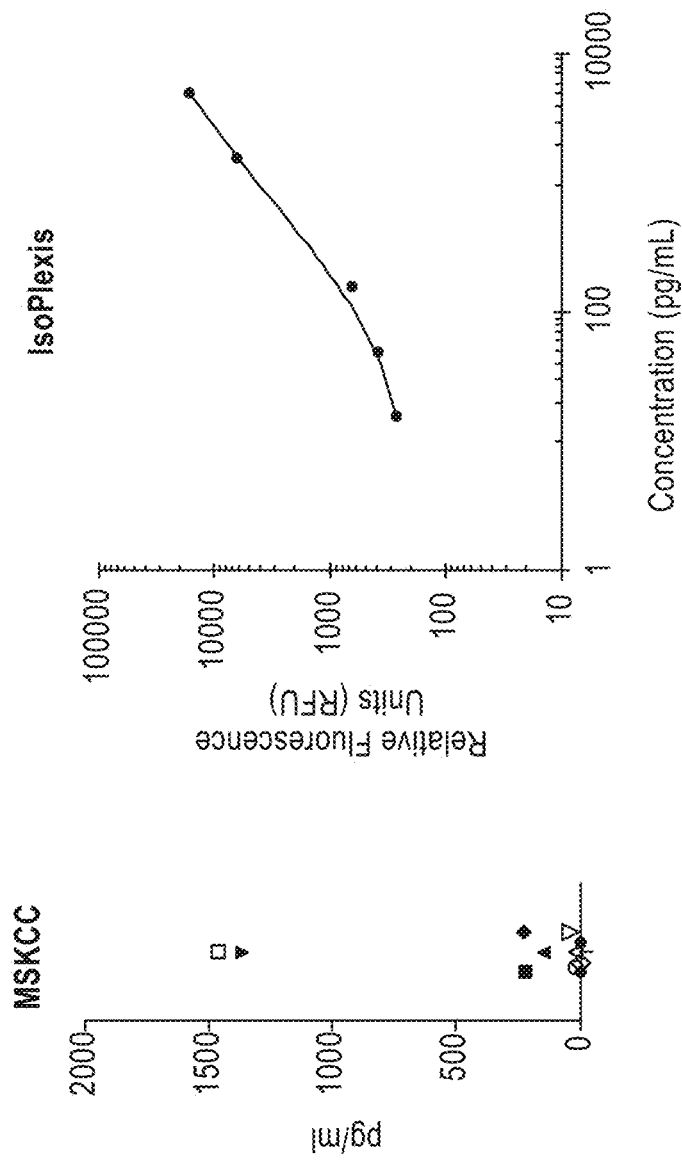
Figure 12F:
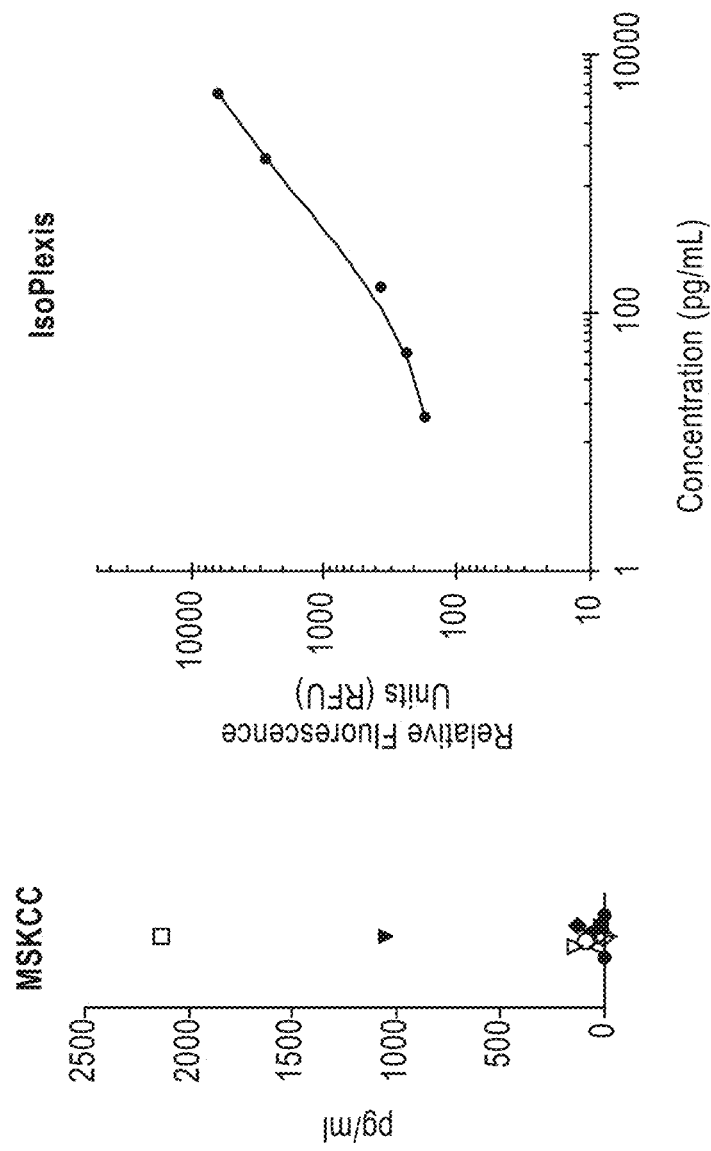
Figure 12G:
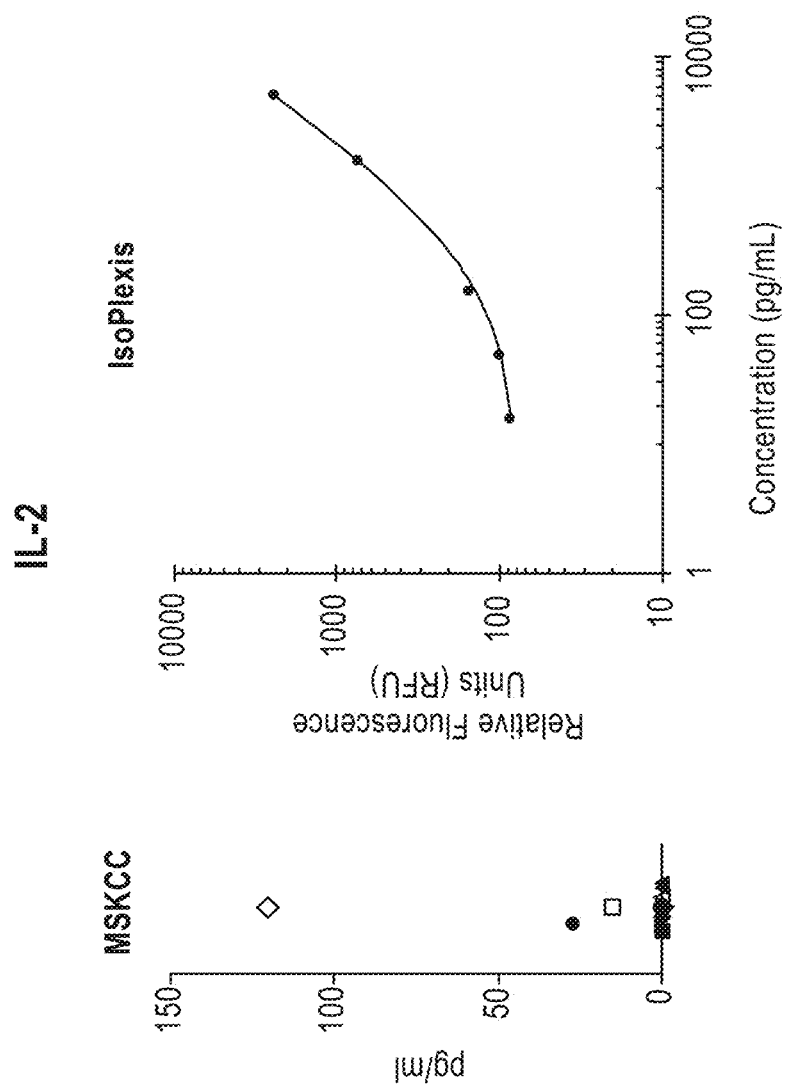
Figure 12I:
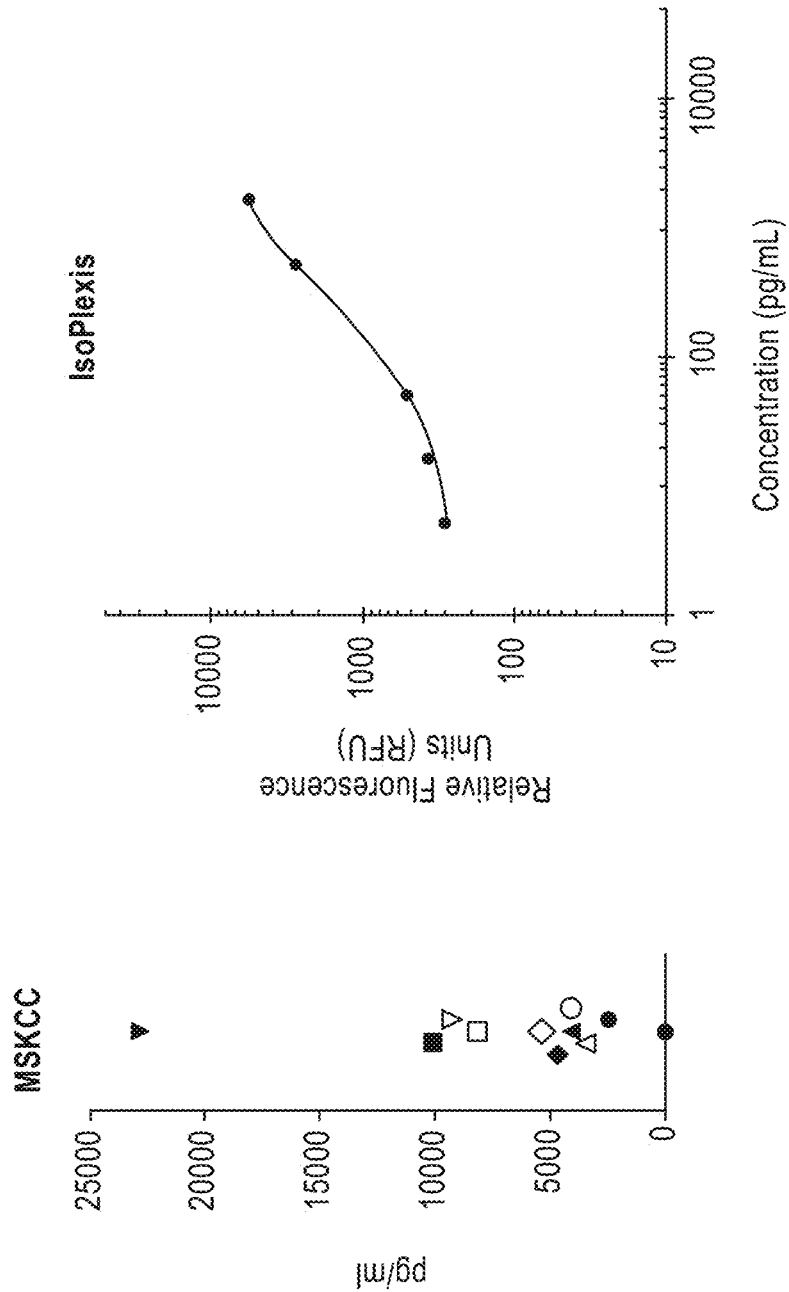
Figure 12J:
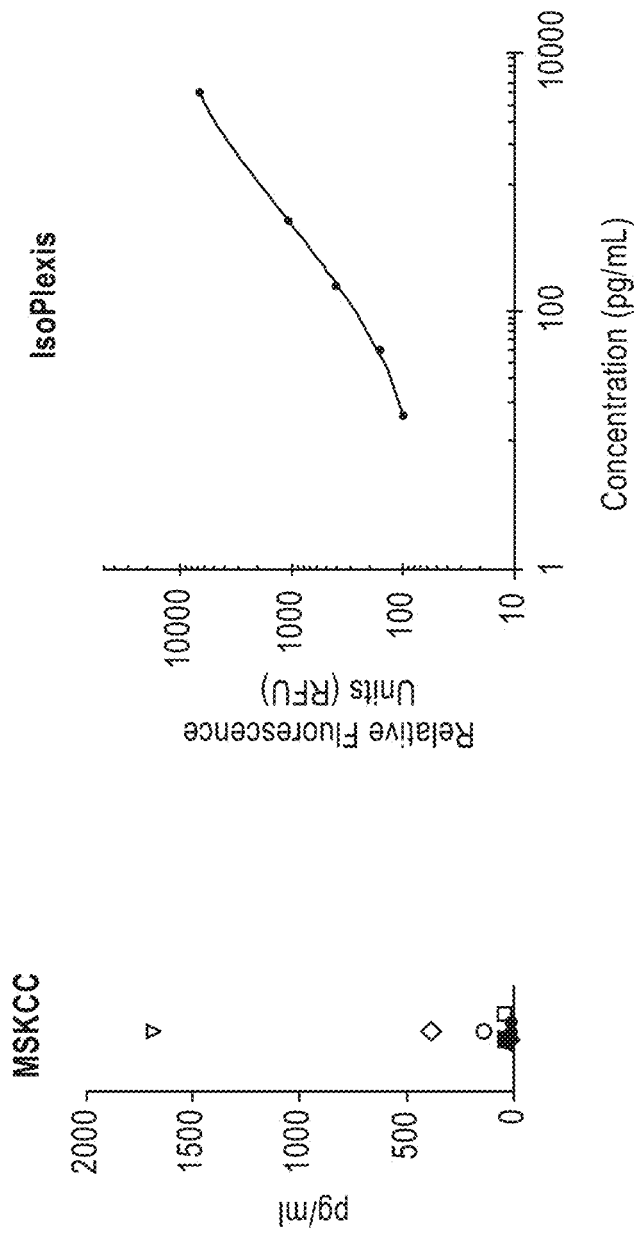
Figure 12K:
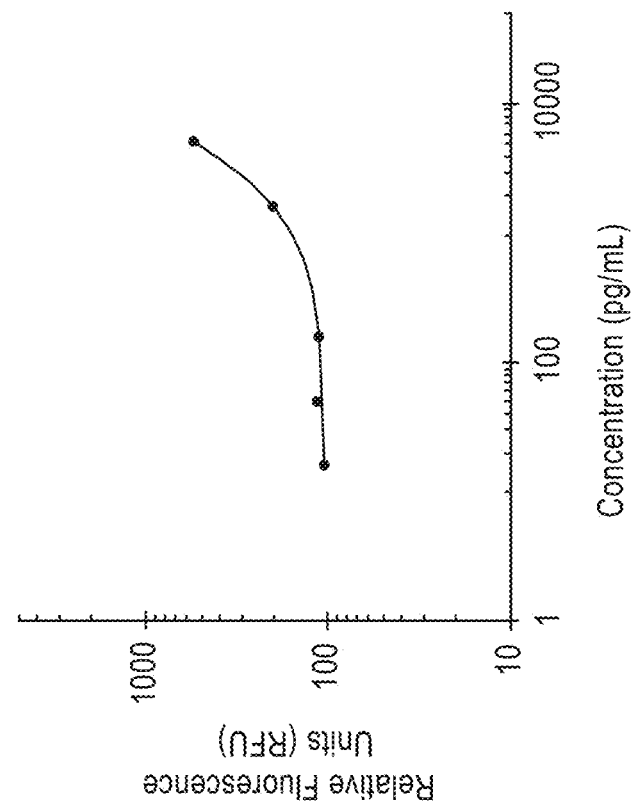
Figure 12K:
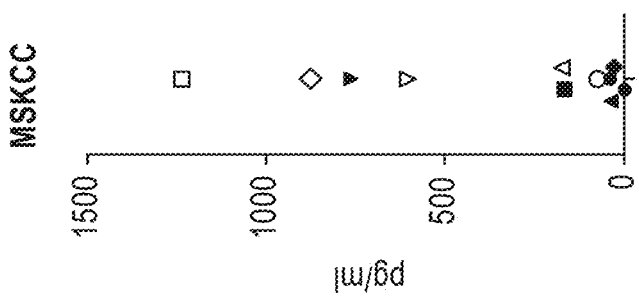
Figure 12L:
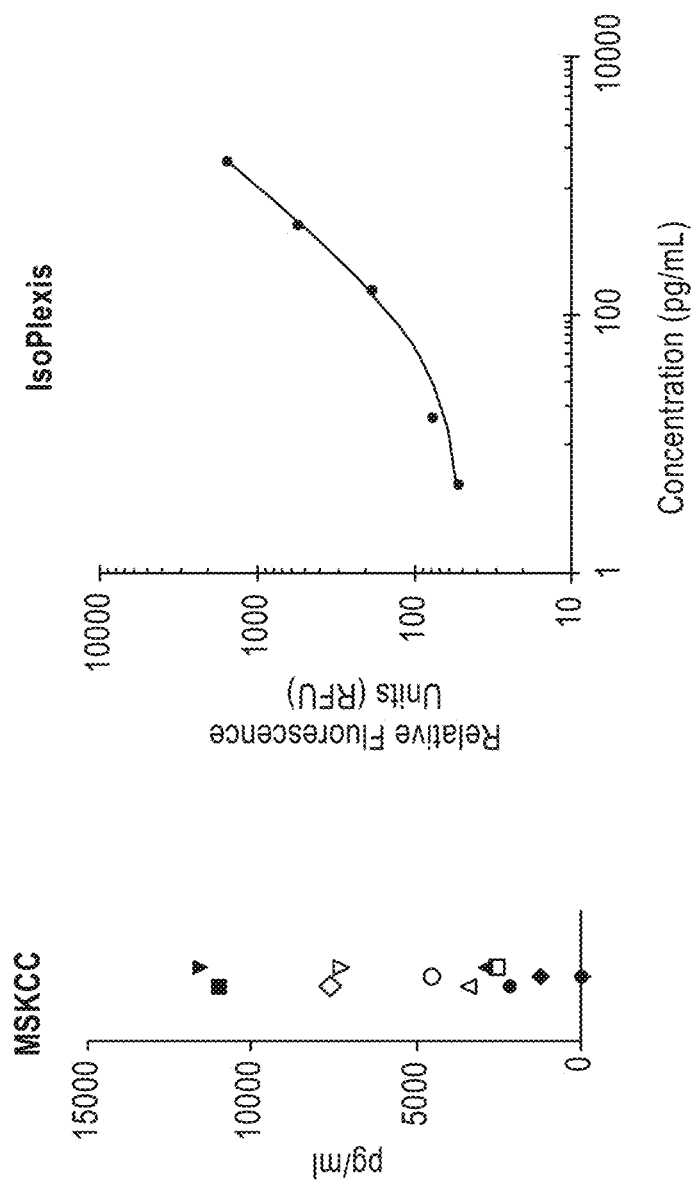
Figure 12M:
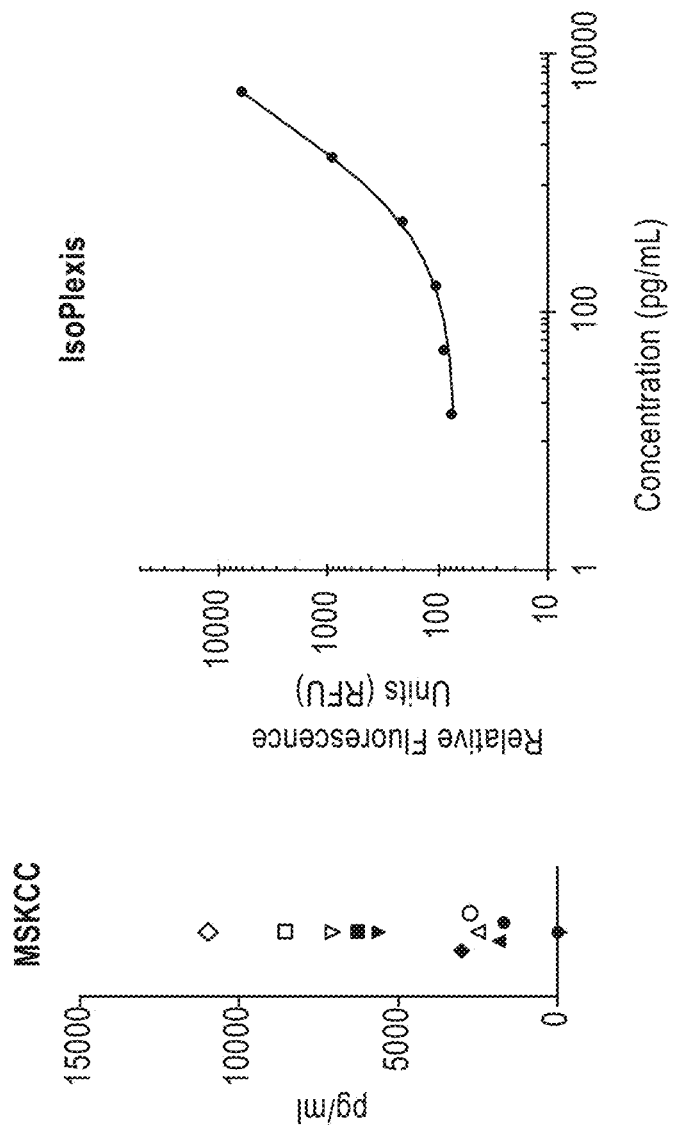

In the right graph of FIG. 11D, we see that there are several cytokines that drive the polyfunctional strength of the sample. The PSI is primarily composed of inflammatory cytokines IL-6 and MCP-1 and effector cytokines Granzyme B and Perforin. Many other cytokines contribute to a lesser degree to the PSI of the sample.

FIGS. 10C and 11C show vertical scatterplots of all the single-cell secretions from the specified population. Each orange dot corresponds to a specific cytokine that was secreted at a particular intensity by a single cell. These are background-subtracted intensities; all intensities shown here are above 0, and thus correspond to single-cell secretions. Data points <0, indicating that a single cell did not secrete a specific cytokine, are not shown.

The units of the intensity levels (y-axis) shown in the graphs are arbitrary, but based on "on-chip" calibration curves ("on chip" may also be referred to as "in situ" with respect to the compositions of the disclosure), these values were converted to approximate pg/mL secretion amounts. The percentage label above each cytokine's vertical scatterplot corresponds to the percentage of single cells in the sample that secreted that cytokine. The larger percentage at the top of the graph indicates how many secretions (as a fraction of all secretions) fell above 1000, to highlight strong secretions (1000 is an arbitrary threshold that may be adjusted and/or made specific to each cytokine).

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A method of identifying a heterogeneous cell population that fails to meet a predetermined safety threshold for use in cell therapy, wherein the heterogeneous cell population comprises subject cells and wherein each subject cell is a T-lymphocyte, the method comprising:
   (a) contacting each subject cell and a target cell or a stimulatory agent under conditions sufficient to permit stimulation of each subject cell;
   (b) introducing each subject cell to a corresponding chamber of a plurality of chambers, wherein the corresponding chamber is in fluid communication with an antibody panel;
   (c) maintaining each subject cell in the corresponding chamber under conditions sufficient to permit
      (i) each subject cell to secrete at least a first cytokine and a second cytokine, and
      (ii) at least one antibody of the antibody panel specific for the first cytokine to bind the first cytokine forming an antibody:first cytokine complex, and at least one antibody of the antibody panel specific for the second cytokine to bind the second cytokine forming an antibody:second cytokine complex;
   (d) imaging at least the first cytokine and the second cytokine of the antibody:first cytokine complex and the antibody:second cytokine complex, thereby identifying a secretome of each subject cell following contact with the target cell or the stimulatory agent;
   (e) calculating a percentage of polyfunctional subject cells in the heterogeneous cell population based on secretomes of each subject cell therein, each subject cell of the heterogeneous cell population being labeled as a polyfunctional cell when a corresponding secretome indicates secretion of at least the first cytokine and the second cytokine;
   (f) calculating (i) a first product of the percentage of polyfunctional subject cells and a measured signal intensity of the first cytokine, and (ii) a second product of the percentage of polyfunctional subject cells and a measured signal intensity of second cytokine, wherein each measured signal intensity is determined by the imaging; and
   (g) identifying the heterogeneous cell population as not safe for use in a cell therapy when at least 50% of the subject cells in the heterogeneous cell population are polyfunctional, the signal intensity of the first cytokine indicates that the concentration of the first cytokine within the chamber is greater that a first predetermined threshold, the signal intensity of the second cytokine indicates that the concentration of the second cytokine within the chamber is greater than a second predetermined threshold.

2. The method of claim 1, wherein the T-lymphocyte expresses a non-naturally occurring antigen receptor.

3. The method of claim 1, wherein the T-lymphocyte expresses a Chimeric Antigen Receptor.

4. The method of claim 1, wherein the target cell is a B-lymphocyte.

5. The method of claim 1, wherein the target cell is a microbe.

6. The method of claim 1, wherein the target cell is a host cell.

7. The method of claim 1, wherein the stimulatory agent is an antibody that specifically binds an epitope of a T cell regulator protein.

8. The method of claim 1, wherein the antibody panel forms a repeating pattern on a surface attached to the plurality of chambers.

9. The method of claim 1, wherein the first cytokine is a regulatory cytokine and the second cytokine is an inflammatory cytokine.

10. The method of claim 9, wherein the regulatory cytokine is selected from the group consisting of IL-10, IL-13, IL-22, IL-4, TGF-β1, sCD137 and sCD40L, and the inflammatory cytokine is selected from the group consisting of IL-17A, IL-17F, IL-1β, IL-6, MCP-1 and MCP-4.

11. The method of claim 1, wherein the first cytokine and the second cytokine are regulatory cytokines.

12. The method of claim 11, wherein the regulatory cytokines are selected from the group consisting of IL-10, IL-13, IL-22, IL-4, TGF-β1, sCD137 and sCD40L.

13. The method of claim 1, wherein the first cytokine and the second cytokine are inflammatory cytokines.

14. The method of claim 13, wherein the inflammatory cytokines are selected from the group consisting of IL-17A, IL-17F, IL-1β, IL-6, MCP-1 and MCP-4.

15. The method of claim 1, wherein the first predetermined threshold is 2 pg/ml.

16. The method of claim 1, wherein the second predetermined threshold is 2 pg/ml.

* * * * *